United States Patent [19]

Anelli et al.

[11] Patent Number: 5,649,537

[45] Date of Patent: Jul. 22, 1997

[54] PARAMAGNETIC METAL ICON CHELATES AND USE THEREOF AS CONTRAST AGENTS IN MAGNETIC RESONANCE IMAGING

[75] Inventors: Pier Lucio Anelli; Christoph De Haen; Luciano Lattuada; Pierfrancesco Morosini; Fulvio Uggeri, all of Milan, Italy

[73] Assignee: Dibra S.p.A., Milan, Italy

[21] Appl. No.: 443,342

[22] Filed: May 17, 1995

[30] Foreign Application Priority Data

May 26, 1994 [IT] Italy .................................. MI94A1074

[51] Int. Cl.$^6$ .................................................. A61B 5/055
[52] U.S. Cl. ........................................ 128/653.4; 424/9.3
[58] Field of Search .................... 128/653.4; 424/9.3, 424/9.32, 9.323, 9.341, 9.351, 9.36, 9.361, 9.364

[56] References Cited

U.S. PATENT DOCUMENTS

| | | | |
|---|---|---|---|
| 5,021,236 | 6/1991 | Gries et al. | 424/9.3 |
| 5,169,944 | 12/1992 | Nelson et al. | 128/653.4 |
| 5,358,704 | 10/1994 | Desreaux et al. | 424/9.3 |
| 5,474,756 | 12/1995 | Tweedle et al. | 128/653.4 |
| 5,527,522 | 6/1996 | Lauffer et al. | 128/653.4 |

*Primary Examiner*—William E. Kamm
*Attorney, Agent, or Firm*—Bucknam and Archer

[57] ABSTRACT

Novel paramagnetic metal ion chelates and their use as contrast agents in the diagnostic technique known as "magnetic resonance imaging" (M.R.I.) of the gastrointestinal tract and particularly of the liver, are described. The novel compounds result from the conjugation of a bile acid with a chelating agent and are capable of chelating the ions of bivalent and trivalent metals. The compounds have formula A-L-B in which A is the residue of a bile acid and derivatives of a bile acid, B is the residue of a chelating agent of a bivalent or trivalent metal ion having an atomic number of 20 to 31, 39, 42, 43, 44, 49, 57 to 83, L is a ligand between A and B.

20 Claims, No Drawings

PARAMAGNETIC METAL ICON CHELATES AND USE THEREOF AS CONTRAST AGENTS IN MAGNETIC RESONANCE IMAGING

FIELD OF THE INVENTION

The present invention relates to novel paramagnetic metal ion chelates and their use as contrast agents in the diagnostic technique known as "magnetic resonance imaging" (M.R.I.). In particular, the present invention relates to bile acid conjugates with molecules endowed with a chelating capacity, as well as their complex chelates with paramagnetic metal ions and/or their salts and the use of these complexes as contrast agents for M.R.I.

BACKGROUND OF THE INVENTION

Complexes formed of chelating agents and suitable specific metals are already used as contrastographic agents in the following diagnostic techniques: X ray imaging, nuclear magnetic resonance imaging (M.R.I.) and scintigraphy.

In particular, medical diagnosis using "magnetic resonance imaging" (M.R.I.), recognized as a powerful diagnostic agent in clinical practice (Stark, D. D., Bradley, W. G. , Jr. , Eds. "Magnetic Resonance Imaging" The C. V. Mosby Company, St. Louis, Mo. (USA), 1988), employs, above all, Paramagnetic pharmaceutical compositions, preferably containing complex chelates of bi-trivalent paramagnetic metal ions with aminopolycarboxylic acids and/or their derivatives or analogues.

Some of them are at present in clinical use as contrast agents for M.R.I. (Gd-DTPA, N-methylglucamine salt of the gadolinium complex with diethylentriaminopentacetic acid, MAGNEVIST®, Schering; Gd-DOTA, N-methylglucamine salt of the gadolinium/1,4,7,10-tetraazacyclododecane-1,4,7,10-tetraacetic acid complex, DOTAREM® Guerbet).

In order to illustrate the state of the art in this field, here follows a list, incomplete, though indicative, of significant patent documents: EP 71564 (Schering), U.S. Pat. No. 4,639,365 (Sherry), U.S. Pat. No. 4,615,879 (Runge), DE-A-3401052 (Schering), EP 130934 (Schering), EP 65728 (Nycomed), EP 230893 (Bracco), U.S. Pat. No. 4,826,673 (Mallinckrodt), U.S. Pat. No. 4,639,365 (Sherry), EP 299795 (Nycomed), EP 258616 (Salutar), WO 8905802 (Bracco).

The contrast agents listed above and on the market are designed for a completely general use. In fact, after administration the MRI contrast agent is distributed in the extracellular spaces in different parts of the body prior to being excreted. In this sense they behave in a similar manner to iodine compounds used in X ray medical diagnosis.

Today, more than ever, the medical profession is in need of contrast agents that are aimed at specific organs, a need which is not adequately met by the products on the market at present. Especially, there is a need for contrast agents for the liver, an organ which is particularly prone to tumoral metastasis and which are almost always carcinomatose metastasis. Agents of this type should be able to provide the following results:

a) to clearly and selectively show the healthy tissue of the liver, thereby permitting the pin-pointing of small lesions such as metastasis (focal liver disease);

b) an indication of hepatic function, whereby a disease as widespread as cirrhosis of the liver may be clearly exposed;

c) a high resolution visualization of the bile ducts and of the gall bladder.

Primary hepatic carcinoma (HCC) is a pathology which has become increasingly and rapidly widespread in the last twenty years, both in the Western World and in Japan (Okuda K., Hepatology, 15, 948,1992). As a result of this, the need for a fast and efficient method of diagnosis for the detection of HCC emerges; for this purpose, Magnetic Resonance takes on a leading rôle, the proviso being the availability of a contrast agent which allows for the differentiation between the healthy hepatocites and those which are affected.

Today, only one product (AMI-HS of Advanced Magnetics, Reimer, P.; Weissleder, R. et al.; Radiology 177, 729, 1990, patent application WO-9001295) seems to possess the necessary prerequisites for the diagnosis of HCC. One is dealing with "ultra-small" particles of iron oxide (average diameter: 12 nm) coated with arabinogalactose which have a particular affinity with the asialoglycoprotein receptors present on the surface of the hepatocites. However, the use of these particles brings about various side effects, especially with regard to the circulatory system. The identification of an ideal hepatospecific contrast agent is, therefore, still far off.

Among the M.R.I. contrast agents under development, both the compound known as Gd-BOPTA (BRACCO, EP 230893), and the Schering product Gd-EOB-DTPA (EP-A-405704) turned out to be particularly suitable for the visualization of hepatic tissue, due to their characteristics of also being excreted via the bile tract.

The transport of both endogenic and xenobiotic substances by means of the hepatocites and the biliary excretion mechanisms have been amply discussed in the literature, only a few basic concepts of which shall be recalled as follows, see, for example, Meier, P. J. in "Biliary Excretion of Drugs and Other Chemicals", Siegers, C. -P. and Watkins III J. B. Eds. Gustav Fischer Verlag, Stuttgart, 1991.

The passage of a molecule in bile from blood through the Disse space takes place in numerous stages that may be schematically summarized as follows:

the molecule enters the hepatocite through the sinusoid membrane following a mechanism that may or may not be specific (mediated by a carrier or a receptor).

inside the hepatocite the molecule may: 1) be carried unaltered and linked to an intracellular protein or inside a vesicle, 2) undergo a conjugation reaction with an enzyme and be excreted in the bile as a conjugate, 3) be enzymatically degraded inside the lisosomes.

the molecule leaves the hepatocite through the bile canaliculus membrane via a mechanism mediated by a carrier or through an exocytosis mechanism (if the molecule is carried inside the vesicle).

If the object is to synthesize a hepatotropic contrast agent which enters the hepatocites, the mechanisms that turn out to be the most interesting are those which are mediated by a receptor or a carrier. Up to now, the following carriers have been identified and partially characterized on the membrane sinusoid:

bile acid carriers a bilirubin carrier a fatty acid carrier a carrier for organic cations The first two types of carrier have been studied more in depth and the knowledge with regard to them is far more advanced.

The HCC cellular lines studied to date turn out to be made up of hepatocites which possess the bilirubin carriers. As both Gd-BOPTA and Gd-EOB-DTPA seem to penetrate the interior of the hepatocites taking advantage of this carrier, both products may not be of any help in the diagnosis of HCC, because they are not capable of differentiating between healthy and affected hepatocites.

It has been shown that in some human HCC lines the hepatocites are free from taurcalcoholic acid carriers (yon Dippe, P; Levy, D.; J. Biol. Chem. 265, 5942, 1990 and cited references). It appears, therefore, that research for a contrast agent that utilizes this carrier for penetrating hepatocites is of great interest.

Patent Application (EP-A-279307, Abbott) claims polyaminocarboxylic chelant conjugates, able to complex metal ions, with different substrates, among which are the bile acids. The only illustrative complex in the case of this Patent Application is a $^{111}$In complex of a conjugate in which a functionalized derivative of EDTA is covalently linked, through an amide link, to the carboxylic function of cholic acid. The possibility of chelating paramagnetic metal ions for the use in MRI is not mentioned.

Another Patent Application (EP-A-417725, Hoechst) generally claims products in which a bile acid is conjugated with pharmacologically active residues such as peptids, antibiotics, antivirals, renin inhibitors and medicaments for the treatment of diabetes. Recently, the results of the use of bile acid conjugates with chlorambucil, an antitumoral agent with cytotoxic action are reported by Kramer, W. et al.; J. Biol. Chem. 267,18598, 1992.

SUMMARY OF THE INVENTION

The present invention covers to novel compounds resulting from the conjugation of a bile acid with a chelating agent and capable of chelating the ions of bi-trivalent metals.

The present invention also covers to the complex chelates of these molecules with the ions of bi-trivalent metals, as well as the salts of the chelates.

These compounds turned out to be excellent MRI contrast agents, particularly for the "imaging" of the hepatobiliary system.

The present invention covers compounds of formula (I):

A-L-B (I), wherein

A is the residue of a bile acid, wherein by bile acid the group of the bile acids obtainable by bioconversion from cholesterol is meant, particularly the acids: cholic, deoxycholic, chenodeoxycholic, ursodeoxycholic, lithocholic, and the derivatives thereof, including those with taurine and glycine;

L is a linker between one of the C-3, C-7, C-12 or C-24 positions of the residue of the bile acid and B, corresponding to a group of formula (II)

(II)

in which m is an integer varying from 1 to 10, wherein for values above 1,

Y can have different meanings,

Y corresponds to the following succession of groups,

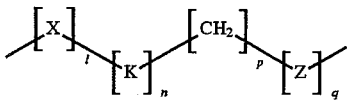

n, l and q can be 0 or 1, p can vary from 0 to 10,

X is an O atom, a S atom, or a —NR group, in which

R is a H atom, or a ($C_1$–$C_5$) alkyl group,

K is benzene ring, substituted or not, or a —$CHR_1$ group, wherein $R_1$ is an hydrogen atom, or a —COOH group, or a —$SO_3H$ group, Z is an O atom or a S atom, or one of the —CO— or —CS— groups, B is the residue of a chelating agent of bi-trivalent metal ions having an atomic number varying from 20 to 31, 39, 42, 43, 44, 49, or from 57 to 83, wherein this residue can in its turn be conjugated or not, by a second chain L of formula (II), to another residue A as defined above, with the proviso that at least one of l, n, q, p is different from 0 and, when X and Z are both O or S atoms, q or n is equal to 1.

An object of the invention also are the complex chelates of the compounds of formula (I) with the bi-trivalent ions of metal elements having an atomic number varying from 20 to 31, 39, 42, 43, 44, 49, or from 57 to 83, as well as the salts thereof with physiologically compatible organic bases selected from primary, secondary, tertiary amines or basic amino acids, or with inorganic bases the cations of which are sodium, potassium, magnesium, calcium or mixtures thereof, or with anions of physiologically acceptable organic acids, for example selected from acetate, succinate, citrate, fumarate, maleate, oxalate, or with anions of inorganic acids such as the ions of the halohydric acids, i.e. chlorides, bromides, iodides.

The compounds of the present invention can optionally be conjugated chemically to suitable macromolecules or inglobated into suitable carriers.

An object of the invention is also the preparation of the products of general formula (I) and of the complex salts thereof, the uses thereof and the related pharmaceutical compositions for diagnostic use.

Particularly preferred compounds of the present invention are those in which the spacing chains L have the following general formulae (III), (IV), (V), (VI)

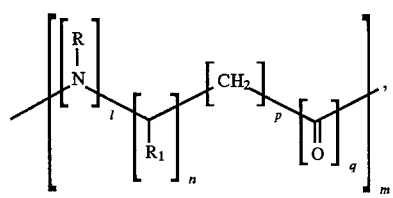
(III)
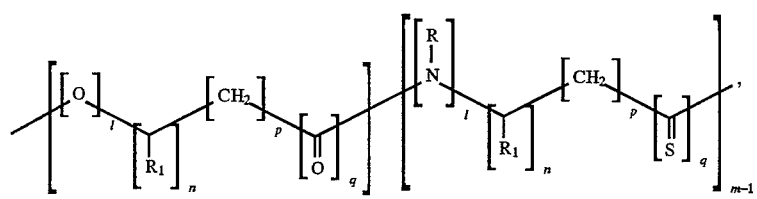
(IV)
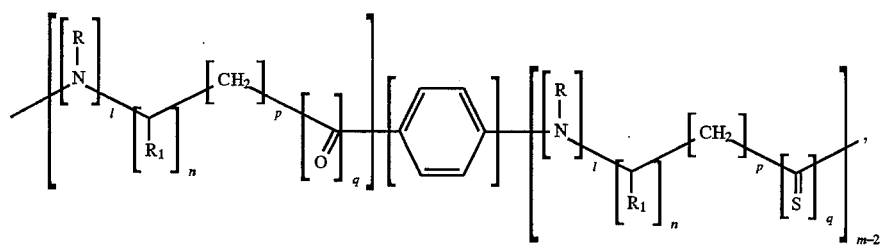
(V)
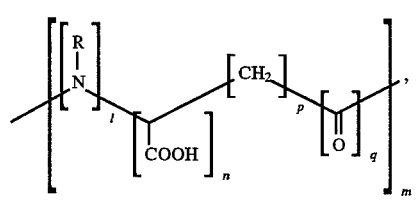
(VI)
Moreover, particularly preferred are the structures in which A is a residue deriving from the following bile acids or form their derivatives with taurine and glycine:
Bile acids
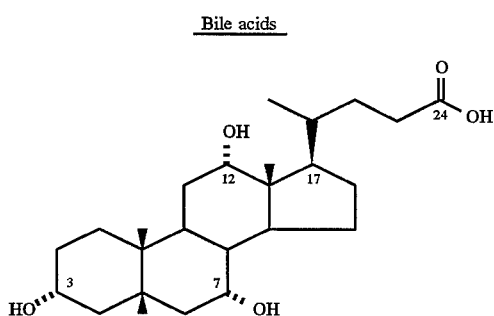
Cholic acid
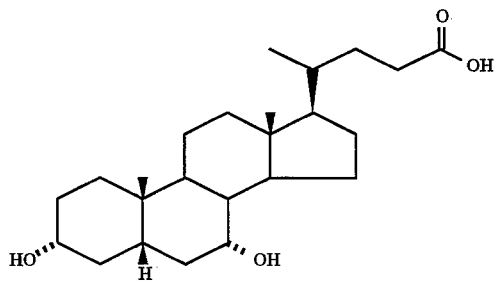
Chenodeoxycholic acid
-continued
Bile acids
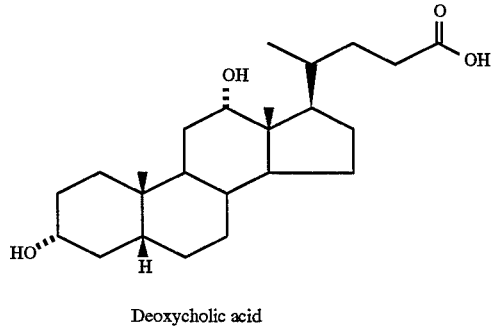
Deoxycholic acid
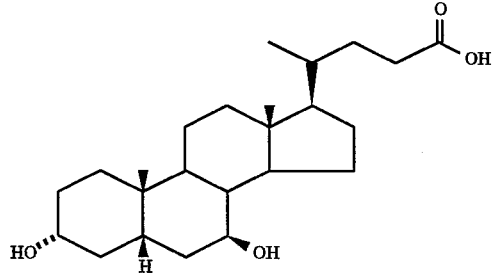
Ursodeoxycholic acid

Bile acids

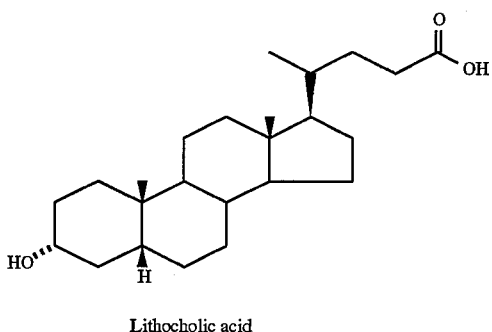

Lithocholic acid

The bond between A and L is obtained making use either of the acidic function at the 24- position, or by functionalizing the hydroxy groups at the 3-, 7-, 12- positions, independently from the stereochemistry of the final products.

B is preferably the residue of a polyaminopolycarboxylic acidic linker and derivatives thereof, particularly diethylenetriamino pentaacetic acid (DTPA), 1,4,7,10-tetraazacyclododecane-1,4,7,10-tetraacetic acid (DOTA), 1,4,7,10-tetraazacyclododecane-1,4,7-triacetic acid (DO3A), [10-(2-hydroxypropyl)1,4,7,10-tetraazacyclododecane-1,4,7-triacetic acid (HPDO3A), 4-carboxy-5,8,11-tris(carboxymethyl)-1-phenyl-2-oxa-5,8,11-triazatridecan-13-oic acid (BOPTA), N-[2-[bis(carboxymethyl)amino]-3-(4-ethoxyphenyl)propyl]-N-[2-[bis(carboxymethyl)amino]ethylglycine (EOB-DTPA), N,N-bis[2-[(carboxymethyl)[(methylcarbamoyl)methyl]amino]ethyl]glycine (DTPA-BMA), 2-methyl-1,4,7,10-tetraazacyclododecane-1,4,7,10-tetraacetic acid (MCTA), ($\alpha,\alpha',\alpha'',\alpha'''$)-tetramethyl-1,4,7,10-tetraazacyclododecane-1,4,7,10-tetracetic acid (DOTMA); or B is the residue of a polyaminophosphate acidic linker or of the derivatives thereof, particularly N,N'-bis-(pyridoxal-5-phosphate) ethylendiamino-N,N'-diacetic acid (DPDP) and ethylenedinitrilotetrakis(methylphosphonic) acid (EDTP); or B is the residue of a polyaminophosphonic acid linker and the derivatives thereof, or polyaminophosphinic acid and the derivatives thereof, particularly 1,4,7,10-tetraazacyclododecane-1,4,7,10-tetrakis[methylen(methylphosphonic)] acid and 1,4,7,10-tetraazacyclododecane-1,4,7,10-tetrakis[methylen(methyphosphinic)] acid; or B is the residue of macrocyclic chelating agents such as texaphyrins, porphyrins and phthalocyanines.

The link to the spacing chain can be obtained by means of the acidic groups of the linker or by a suitable reactive group present in the starting linker, for example an amino group, or a functional group present on a phenyl, etc.

Particularly preferred reactive groups are selected from the group consisting of —NH$_2$, —NCS, —NHCSNHNH$_2$, —NHCSNH(CH$_2$)$_2$NH$_2$, —NCO, —NHNH$_2$, —NHCONHNH$_2$, —CHO.

Particularly preferred are the structures in which A is a residue of cholic acid, B is a residue of the linker BOPTA, of DTPA or of DOTA.

Metal ions suitable to form complex salts with the chelating agents of general formula (I) are mainly the bivalent or trivalent ions of the elements having atomic numbers varying from 20 to 31, 39, 42, 43, 44, 49, or from 57 to 83; particularly preferred are Fe$^{(2+)}$, Fe$^{(3+)}$, Cu$^{(2+)}$, Cr$^{(3+)}$, Gd$^{(3+)}$, Eu$^{(3+)}$, Dy$^{(3+)}$, La$^{(3+)}$, Yb$^{(3+)}$ or Mn$^{(2+)}$ or also radioisotops such as $^{51}$Cr, $^{67}$Ga, $^{68}$Ga, $^{111}$In, $^{99m}$Tc, $^{140}$La, $^{175}$Yb, $^{153}$Sm, $^{166}$Ho, $^{90}$Y, $^{149}$Pm, $^{177}$Lu, $^{47}$Sc, $^{142}$Pr, $^{159}$Gd, $^{212}$Bi.

The compounds of General formula (I) can be prepared with synthesis methods conventionally known in industrial technology. Particularly, MRI contrast agents conjugated with bile acids can be prepared by means of a convergent synthesis which comprises:

1) synthesis of a functionalized ligand i.e. of a ligand capable of coordinating one paramagnetic metal ion and at the same time of binding stably to the bile acid by means of a suitable functional group;

2) synthesis of a functionalized bile acid;

3) coupling reaction between two different syntons;

4) cleavage of any protective groups;

5) complexation of the paramagnetic metal ion.

In the following Scheme 1, some of the functional groups most easily obtainable respectively on cholic acid and on the ligand, as well as the mutual possibilities to react to give stable bonds are reported by way of example.

Scheme 1

Functional groups

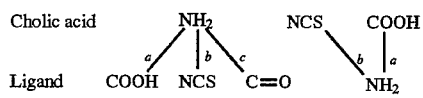

As it can be observed, the conjugation of the two syntons is carried out through three different known binding methods, widely used in synthesis (see Brinkley, M., Bioconjugate Chem. 1992, 3, 2), which involve formation of an amide (path a), of a thiourea (path b) or, through reduction of the intermediate imine, of an amine (path c).

The functional groups of the two syntons of Scheme 1 are moreover liable to further modifications before the binding reaction, for example by reaction with suitable bifunctional spacers.

An example of ligands corresponding to point 1) described above is represented by the molecules in Scheme 2.

Scheme 2

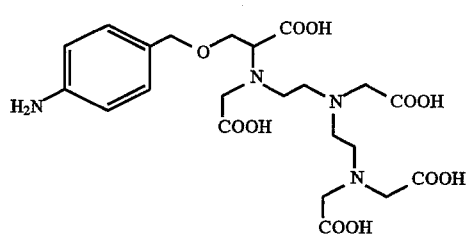

C

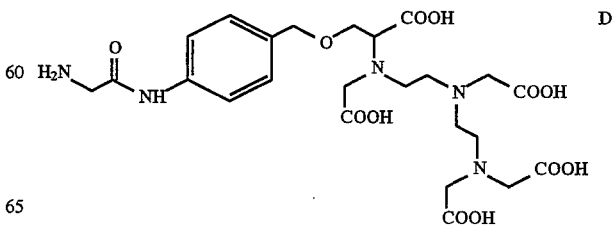

D

-continued
Scheme 2

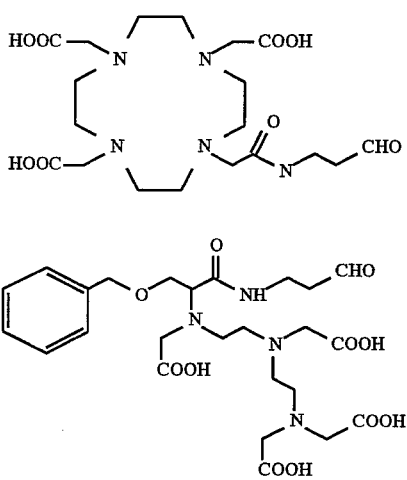

By way of non-limiting example, the synthesis of ligands C and D, the latter being the glycine derivative (Scheme 3), can be cited herein. The synthesis of t-butyl 2-bromo-3-[(4-nitrophenyl)methoxy]propionate was performed according to the procedure described by P. L. Rings et al., Synth. Commun., 23, 2639, 1993. In a similar way, starting from t-butyl 2-bromo-4-[(4-nitrophenyl)]butanoate (prepared according to the procedure described in Kruper W. J.; Rudolf P. R.; Langhoff C. A. J. Org. Chem., 58, 3869, 1993), a ligand which involves no benzyloxy groups can be prepared.

In Scheme 3 the t-butyl esters are shown, but they can easily be substituted by other alkyl groups.

The synthesis continues with the condensation of the α-bromopropionic intermediate with diethylenetriamine and the subsequent carboxymethylation with t-butyl α-bromoacetate under the usual conditions known in literature.

The reduction of the nitro group is performed by means of hydrogen using 10% Pd/C as the catalyst. At this point, the key synton is available for binding through the amino group present on an aromatic ring of the ligand with the acidic groups of the bile acids or with derivatives thereof in which carboxylic groups are present.

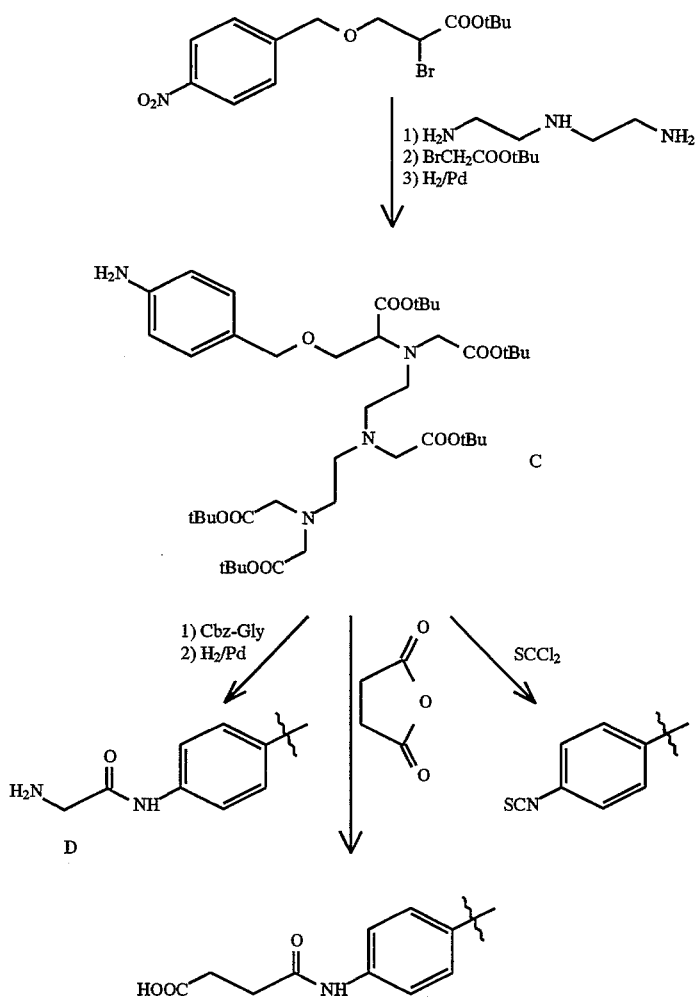

An example of functionalization of the steroid can be represented by the synthesis of cholic acid 3β-amino derivative according to Scheme 4, using in an original way the Mitsunobu reaction (Review, Synthesis, 1, 1981) which allows the selective transformation of the 3α hydroxyl group into the corresponding 3β azido group.

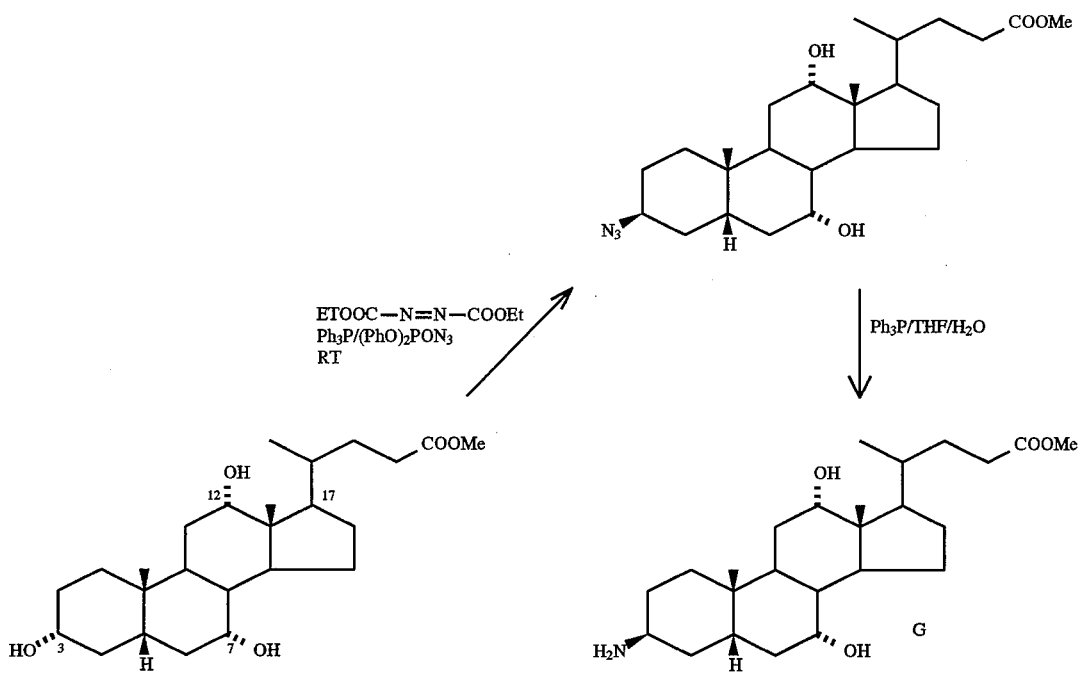

Intermediate G can be used as such or it can easily be changed into other intermediates as much interesting, as evidenced in Scheme 5.

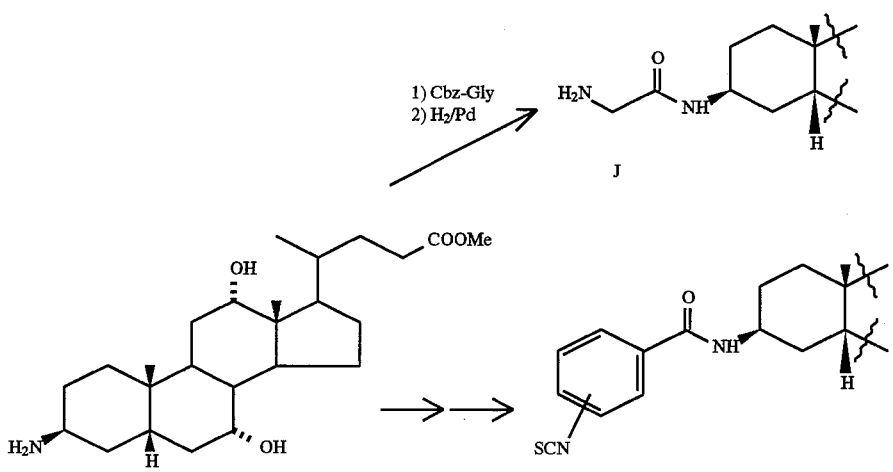

-continued
Scheme 5

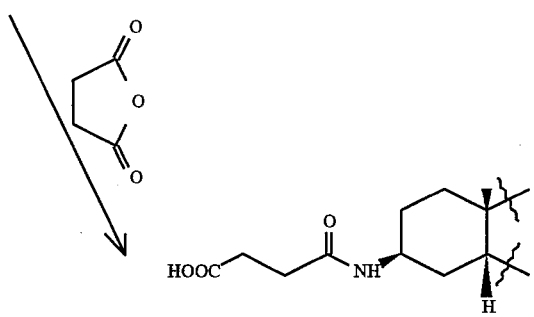

An example of binding reaction between the components A and B of general formula (I) of the compounds of the present invention, is the formation of the amido bond between the steroid carboxylic group at the 24-position and the amino group present in the ligand, for example C and D of Scheme 2.

The reaction is preferably activated by the addition of diethoxyphosphoryl cyanide (DEPC), according to the procedure described for the peptide synthesis (Shioiri, T. et al., Tetrahedron, 32, 2211, 1976). The reaction with DEPC takes place preferably in a dipolar aprotic solvent, such as dimethylformamide (DMF) or dimethylacetamide (DMA) or in a mixture thereof, at a temperature varying from −5° C. to 40° C., preferably from 0° C. to 25° C.

A further example of binding reaction makes use of the formation of a Schiff base between the ligands of type E and F and a suitable steroid derivative, for example the derivative J obtained from 3β-aminocholic derivative according to Scheme 5.

The aldehyde group of the ligand reacts with the amino group present on the steroid and subsequently the amino derivative is reduced with $NaBH_3CN$, according to a well-known procedure of the literature (C. F. Lane, Synthesis, 135, 1975).

The choice of diversifying the ester groups present in both components of the binding reaction, allows for the modulation of the hydrolysis thereof in different synthesis steps.

The conversion of the ester groups of t-butyl type into acidic groups takes place in acid solution. The resulting solution is adjusted to controlled pH thus allowing the simultaneous formation of the desired complex by addition of the stoichiometric amount of metal, in the form of oxide or salt.

The hydrolysis reaction of the ester groups of methyl type takes place preferably in the presence of a suitable organic or inorganic base such as sodium hydroxide, potassium hydroxide, potassium carbonate or, for example, lithium hydroxide at a pH value varying from 8 to 12, preferably between 0° C. and 100° C., more preferably between 0° C. and 50° C.

The possible conjugation with the amino acids taurine and glycine takes place according to the procedure described in Tserng, K.-Y.; Hachey, D. L.; Klein, P. D. J. Lipid Res. 1977, 18, 404.

Finally, the formation of the metal complex salt is preferably carried out in water or in a suitable water-alcohol mixture, while the temperature can vary from 25° C. to 100° C., preferably from 40° C. to 80° C.

The choice of the metal ion and of any neutralizing ions is strictly related to the use of the complex to be prepared.

The novel compounds of the present invention proved to have a good tolerability; moreover their water solubility and the low osmolality of the solutions are another important feature making them particularly suited for the use in nuclear magnetic resonance.

The in vitro relaxivity data evidenced for the compounds of the present invention turned out to be quite good. By way of non-limiting example, the $r_1$ and $r_2$ values found for two of the preferred compounds of the invention, i.e. the 4-carboxy-5,8,11-tris(carboxymethyl)-1-[4-[[[[(3α,5β,7α, 12α)-3,7,12-trihydroxy-24-oxocholan-24-yl]amino]acetyl] amino]phenyl]-2-oxa-5,8,11-triazatridecan-13-oic acid gadolinium complex salified with 1-deoxy-1-(methylamino) -D-glucitol (1:2), and [[10-[2-Oxo-2-[[3-[[2-[[(3α,5β,7α, 12α)-3,7,12-trihydroxy-24-oxocholan-24-yl]amino]ethyl] amino]propyl]amino]ethyl]-1,4,7,10-tetraazacyclododecan-1,4,7-triacetoate(3⁻)]gadolinate(0)] hydrogen compound with HCl (1:1), are reported in EXAMPLE 19, compared with the data available for paramagnetic compounds marketed under the trade marks MAGNEVIST® (Schering) and DOTAREM® (Guerbet), or with the data related to Gd-BOPTA and to the $Gd^{3+}$ ion as such.

Both soluble and less soluble compounds are suited for the oral or enteral administrations and, therefore, particularly for the gastrointestinal tract imaging.

For the parenteral administration, they are preferably formulated as sterile aqueous solutions or suspensions, whose pH can range, for example, from 6.0 to 8.5.

These aqueous solutions or suspensions can be administered in concentrations varying from 0.002 to 1.0 Mol.

These formulations can be freeze-dried and provided as such for the extemporary use. For the gastrointestinal use or for the injection in body cavities, these agents can be formulated as solutions or suspensions containing appropriate additives suitable, for example, to control viscosity.

For the oral administration, they can be formulated according to preparation methods conventionally used in pharmaceutical technique, possibly also as coated formulations to obtain an additional protection against the stomach acidic pH, thus preventing the chelated metal ion from release, which takes place particularly at the pH values typical of gastric juices.

Other excipients, such as sweeteners and/or flavouring agents, can also be added, according to known techniques of pharmaceutical formulations.

As far as the diagnostical use of the chelates of the present invention is concerned, they can also be used as both contrast media and therapeutical agents, in nuclear medicine.

In this case, however, the metal ion which is chelated is a radioisotope, for example $^{51}Cr$, $^{67}Ga$, $^{68}Ga$, $^{111}In$, $^{99m}Tc$, $^{140}La$, $^{175}Yb$, $^{153}Sm$, $^{166}Ho$, $^{90}Y$, $^{149}Pm$, $^{177}Lu$, $^{47}Sc$, $^{142}Pr$, $^{159}Gd$ and $^{212}Bi$.

Preferred inorganic base cations possibly suitable to salify the complex chelates of the present invention comprise particularly the alkali or alkaline-earth metal ions such as potassium, sodium, calcium, magnesium, and mixtures thereof.

Preferred organic base cations suitable for the above mentioned purpose comprise, inter alia, those of primary, secondary and tertiary amine, such as ethanolamine, diethanolamine, morpholine, glucamine, N-methylglucamine, N,N-dimethylglucamine.

Preferred inorganic acid anions possibly suitable to salify the complex chelates of the present invention comprise, particularly, the halohydric acid ions, such as chlorides, bromides, iodides or other ions such as sulfate.

Preferred organic acid anions for the above mentioned purpose comprise those of acids conventionally used in pharmaceutical techniques for the salification of alkali substances, such as acetate, succinate, citrate, fumarate, maleate.

Preferred amino acid cations and anions comprise, for example, those of taurine, glycine, lysine, arginine or ornithine or of the aspartic and glutamic acids.

The complex chelates conjugated with the bile acids, object of the present invention, can also be inglobated into liposomes or be components of their chemical structure and be used as mono- or multilamellar vescicles.

A non-limiting list of preferred compounds of the invention described in the experimental part is reported in the following to illustrate further the present invention.

COMPOUND 1 (EXAMPLE 1)

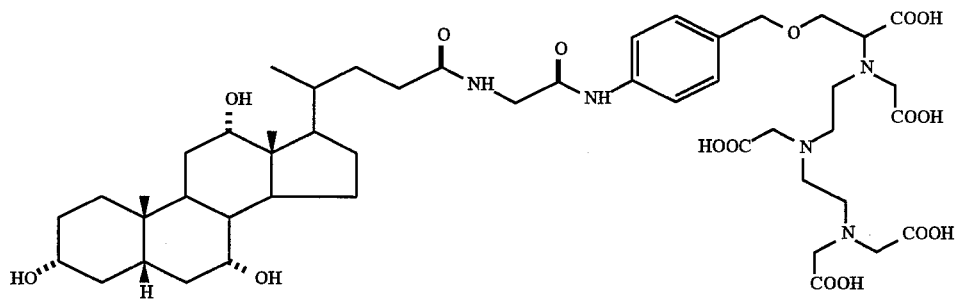

[[4-carboxy-5,8,11-tris(carboxymethyl)-1-[4-
[[[[(3α,5β,7α,12α)-3,7,12-trihydroxy-24-oxocholan-24-
amino]acetyl]amino]phenyl]-2-oxa-5,8,11-triazatridecan-
13-oic acid

COMPOUND 2 (EXAMPLE 2)

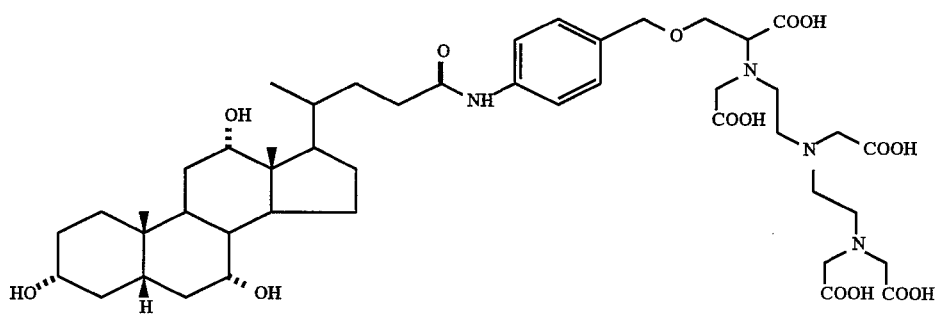

[[4-carboxy-5,8,11-tris(carboxymethyl)-1-[4-
[[(3α,5β,7α,12α)-3,7,12-trihydroxy-24-oxocholan-24-
yl]amino]phenyl]-2-oxa-5,8,11-triazatridecan-13-oic acid

COMPOUND 3 (EXAMPLE 3)

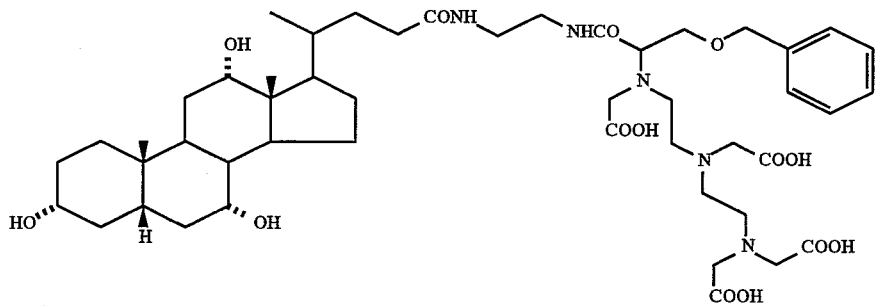

[[3,6,9,tris(carboxymethyl)-10-(phenylmethoxy)methyl-
11-oxo-14-[[3α,5β,7α,12α)-3,7,12-trihydroxy-24-oxocho-
lan-24-yl]amino]-3,6,9,12-tetraazatetradecanoic acid

COMPOUND 4 (EXAMPLE 4)

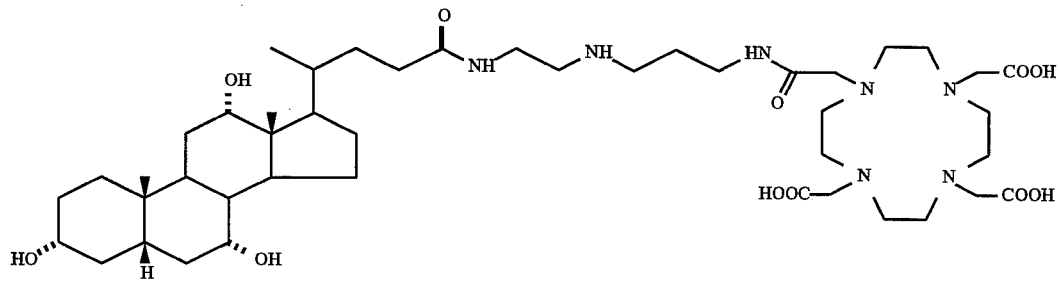

[[10-[2-oxo-2-[[3-[[2-[[(3α,5β,7α,12α)-3,7,12-trihy-
droxy-24-oxocholan-24-yl]amino]ethyl]amino]propyl]-
amino]ethyl]-1,4,7,10-tetraazacyclododecan-1,4,7-tri-
acetic acid

COMPOUND 5 (EXAMPLE 5)

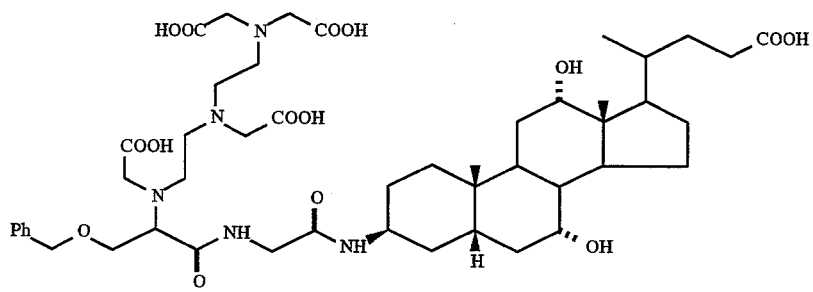

[[(3β,5β,7α,12α)-3-[[13-carboxy-6,9,12-tris (carboxyme-
thyl)-1,4-dioxo-5-[(phenylmethoxy)methyl]-3,6,9,12-te-
traazatridecyl]amino]-7,12-dihydroxy-cholan-24-oic acid

COMPOUND 6 (EXAMPLE 6)

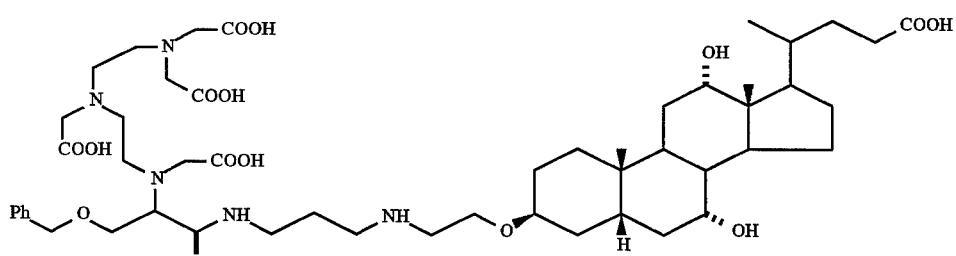

[[(3β,5β,7α,12α)-3-[[17-carboxy-10,13,16-tris(carboxy-
methyl)-8-oxo-9-[(phenylmethoxy)methyl]-3,7,10,13,16-
pentaazaheptadecyl]oxy]-7,12-dihydroxy-cholan-24-oic
acid

COMPOUND 7 (EXAMPLE 7)

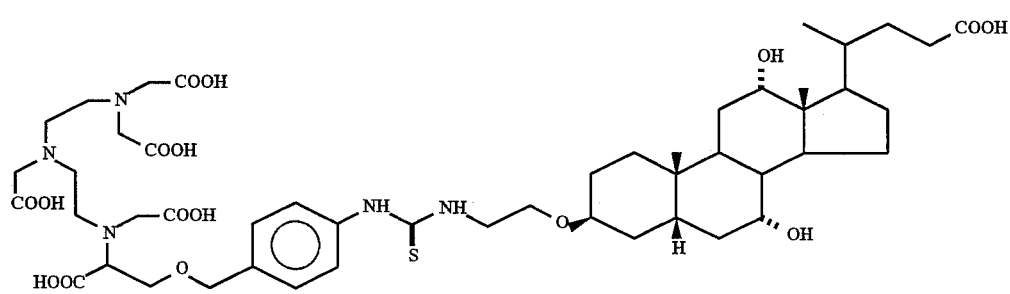

[[(3β,5β,7α,12α)-7,12-dihydroxy-3-[2-[[[[4-[4,12-
bis(carboxy)-5,8,11-tris(carboxymethyl)-2-oxa-5,8,11-
triazadodecyl]phenyl]amino]thioxomethyl]amino]ethoxy]-
cholan-24-oic acid

COMPOUND 8 (EXAMPLE 4)

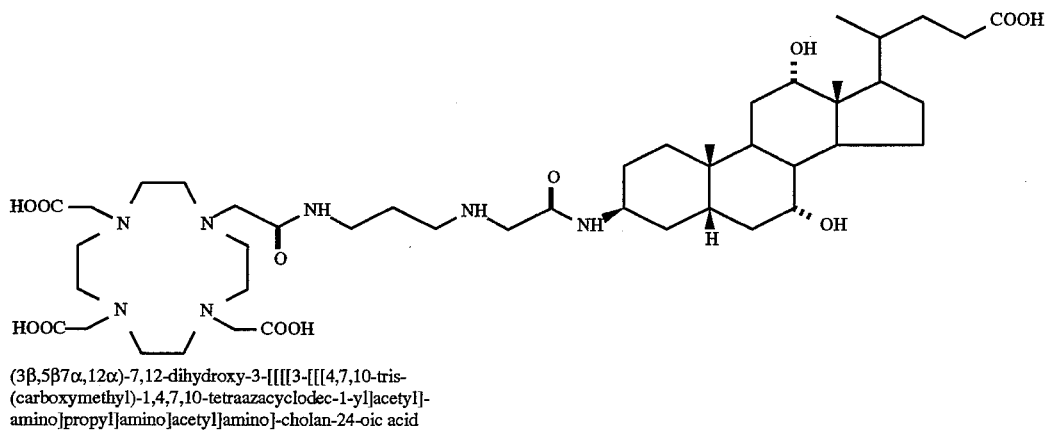

(3β,5β7α,12α)-7,12-dihydroxy-3-[[[[3-[[[4,7,10-tris-
(carboxymethyl)-1,4,7,10-tetraazacyclodec-1-yl]acetyl]-
amino]propyl]amino]acetyl]amino]-cholan-24-oic acid

COMPOUND 9 (EXAMPLE 8)

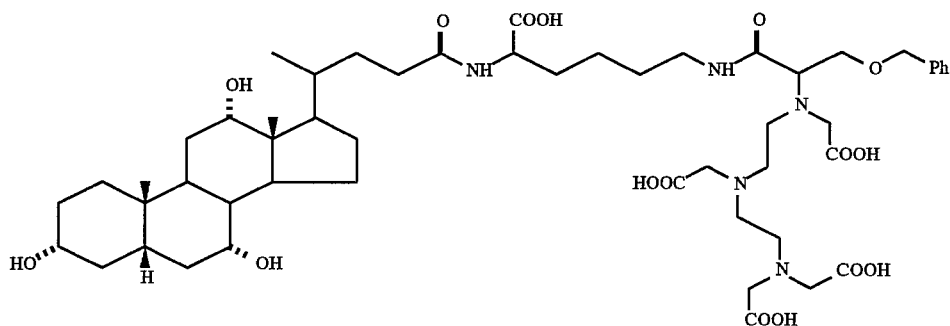

[[3,6,9-tris(carboxymethyl)-10-[(phenylmethoxy)methyl]-
11-oxo-17-[[(3α,5β,7α,12α)-3,7,12-trihydroxy-24-oxocho-
lan-24-yl]amino]-3,6,9,12-tetraazaoctadecanedioic acid

COMPOUND 10 (EXAMPLE 9)

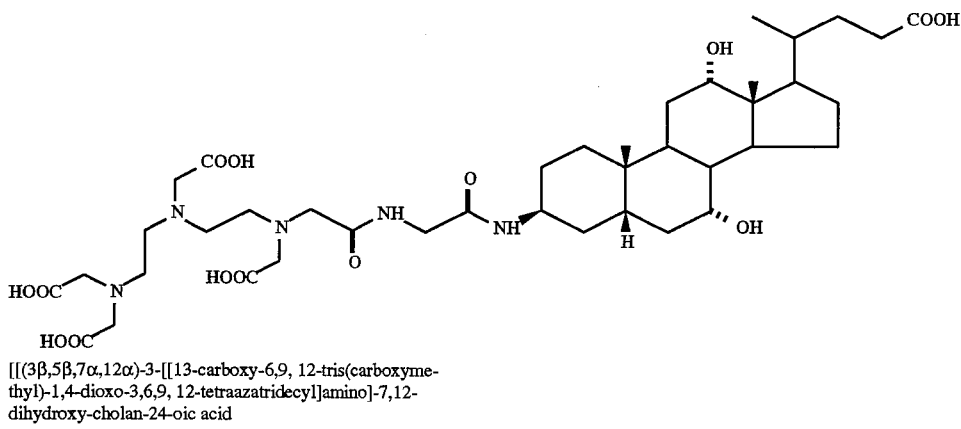

[[(3β,5β,7α,12α)-3-[[13-carboxy-6,9, 12-tris(carboxyme-
thyl)-1,4-dioxo-3,6,9, 12-tetraazatridecyl]amino]-7,12-
dihydroxy-cholan-24-oic acid

COMPOUND 11 (EXAMPLE 10)

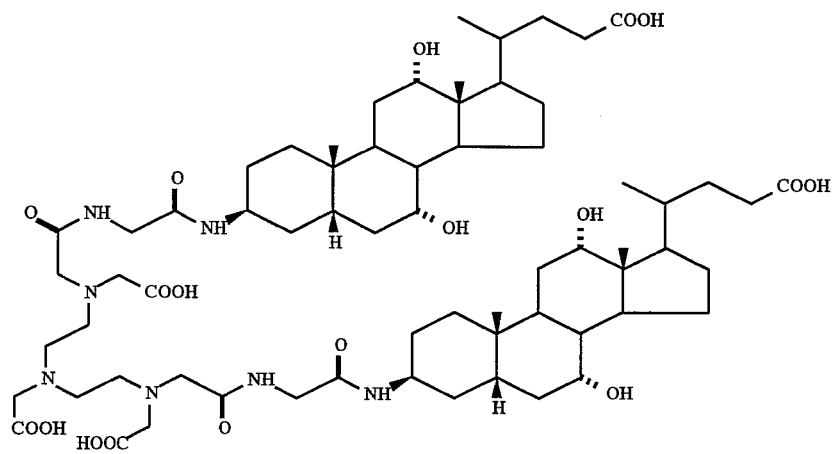

[(3β,5β,7α,12α)-(3'β,5'β,7'α,12'α)-3,3'-[[6,9,12-tris-(carboxymethyl)-1,4,14,17-tetraoxo-3,6,9,12,15-penta-azaheptadecan-1,17-diyl]bisimino]bis[7,12-dihydroxycholan-24-oic acid

COMPOUND 12 (EXAMPLE 11)

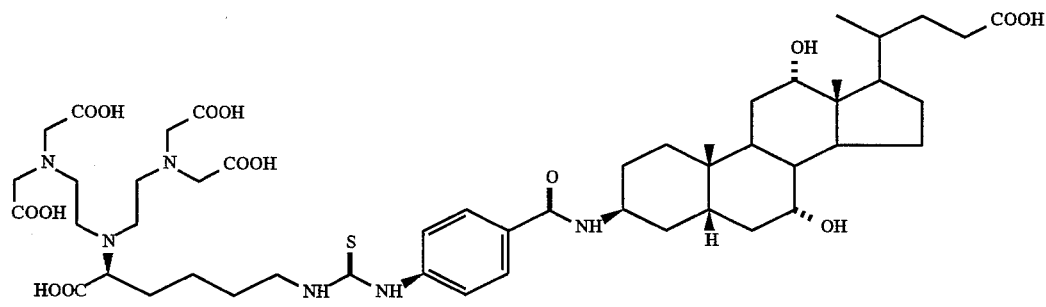

[[[3β(S),5β,7α,12a]-7,12-dihydroxy-3-[[4-[[[[5-[bis[2-[bis(carboxymethyl)amino]ethyl]amino]-5-carboxypentyl]-amino]thioxomethyl]amino]benzoyl]amino]-cholan-24-oic acid

COMPOUND 13 (EXAMPLE 12)

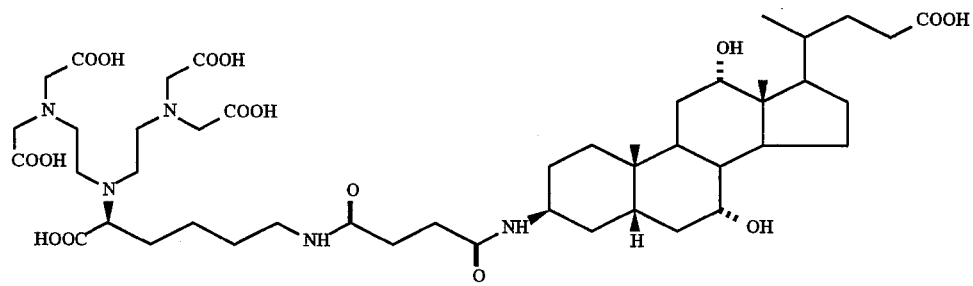

[[[3β(S),5β,7α,12a]-7,12-dihydroxy-3-[[4-[5-[bis[2-[bis(carboxymethyl)amino]ethyl]amino]-5-carboxypentyl]amino]-1,4-dioxobutyl]amino]-cholan-24-oic acid

COMPOUND 14 (EXAMPLE 13)

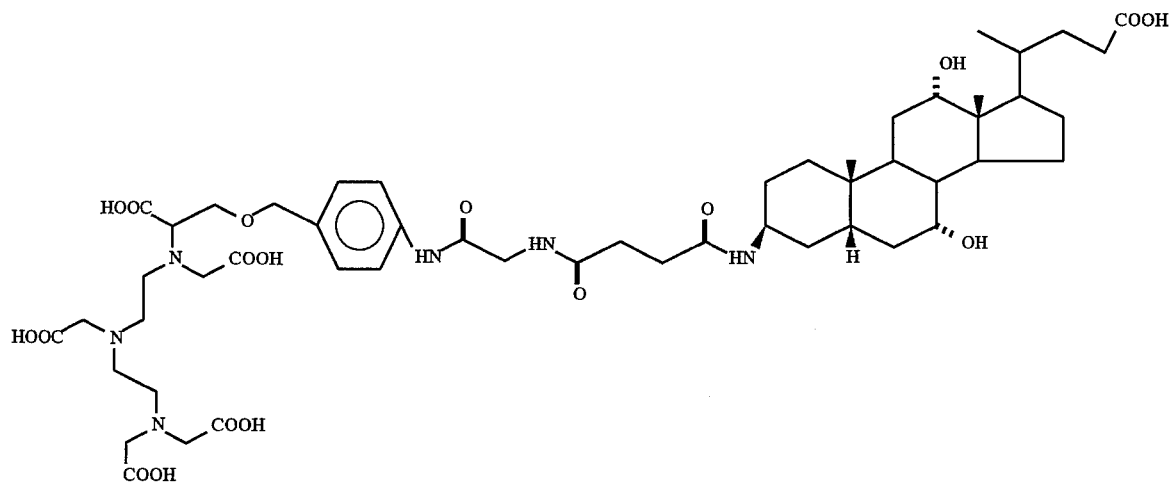

[[(3β,5β,7α,12α)-7,12-dihydroxy-3-[[4-[[2-[[4-[4,12-bis(carboxy)-5,8,11-tris(carboxymethyl)-2-oxa-5,8,11-triazadodecyl]phenyl]amino]-2-oxoethyl]amino]-1,4-dioxobutyl]amino]-cholan-24-oic acid;

COMPOUND 15 (EXAMPLE 5)

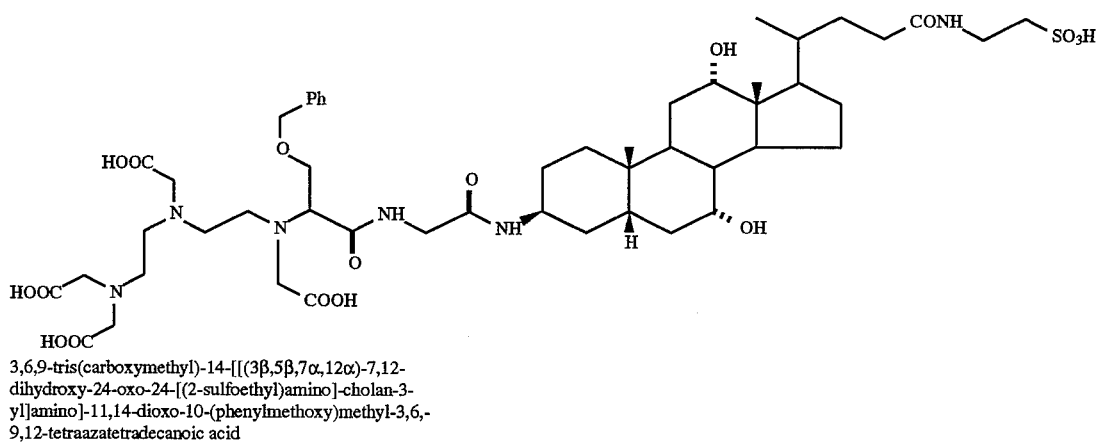

3,6,9-tris(carboxymethyl)-14-[[(3β,5β,7α,12α)-7,12-dihydroxy-24-oxo-24-[(2-sulfoethyl)amino]-cholan-3-yl]amino]-11,14-dioxo-10-(phenylmethoxy)methyl-3,6,9,12-tetraazatetradecanoic acid

COMPOUND 16 (EXAMPLE 5)

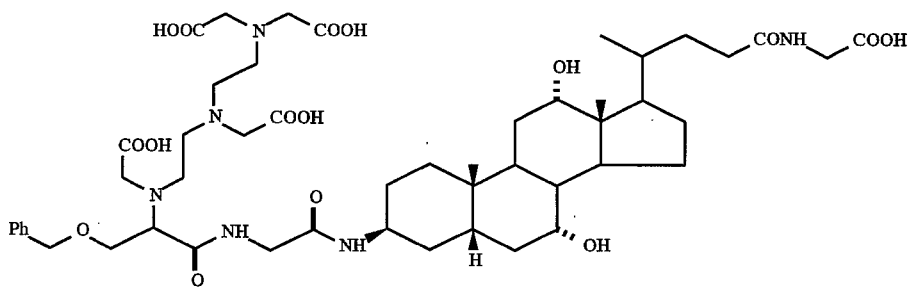

N-[(3β,5β,7α,12α)-3-[[13-carboxy-6,9,12-tris (carboxymethyl)-1,4-dioxo-5-[(phenylmethoxy)methyl]-3,6,9,12-tetraazatridecyl]amino]-7,12-dihydroxy-24-oxocholan-24-yl]glycine -continued

COMPOUND 17 (EXAMPLE 5)

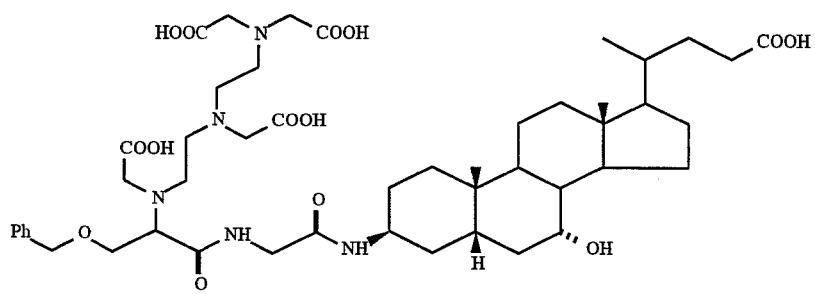

(3β,5β,7α)-3-[[13-carboxy-6,9,12-tris (carboxymethyl)-
1,4-dioxo-5-[(phenylmethoxy)methyl]-3,6,9,12-tetraaza-
tridecyl]amino]-7-hydroxy-cholan-24-oic acid

COMPOUND 18 (EXAMPLE 5)

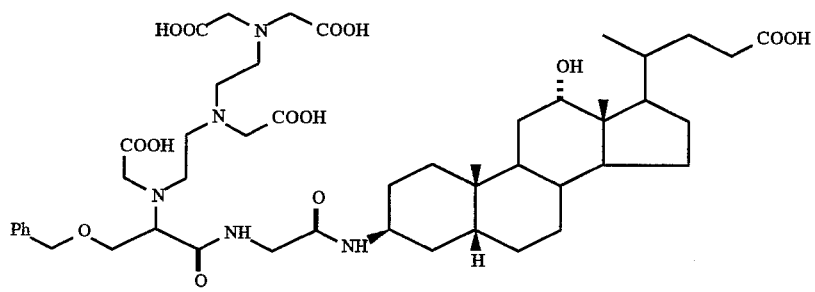

(3β,5β,12α)-3-[[13-carboxy-6,9,12-tris (carboxymethyl)-
1,4-dioxo-5-[(phenylmethoxy)methyl]-3,6,9,12-tetraaza-
tridecyl]amino]-12-hydroxy-cholan-24-oic acid

COMPOUND 19 (EXAMPLE 5)

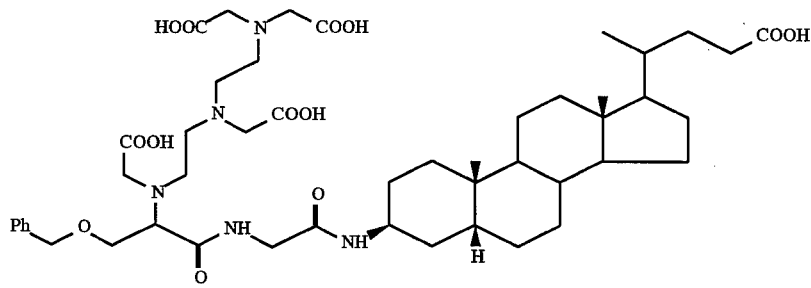

(3β,5β)-3-[[13-carboxy-6,9,12-tris(carboxymethyl)-1,4-
dioxo-5-[(phenylmethoxy)methyl]-3,6,9,12-tetraazatride-
cyl]amino]-cholan-24-oic acid

COMPOUND 20 (EXAMPLE 5)

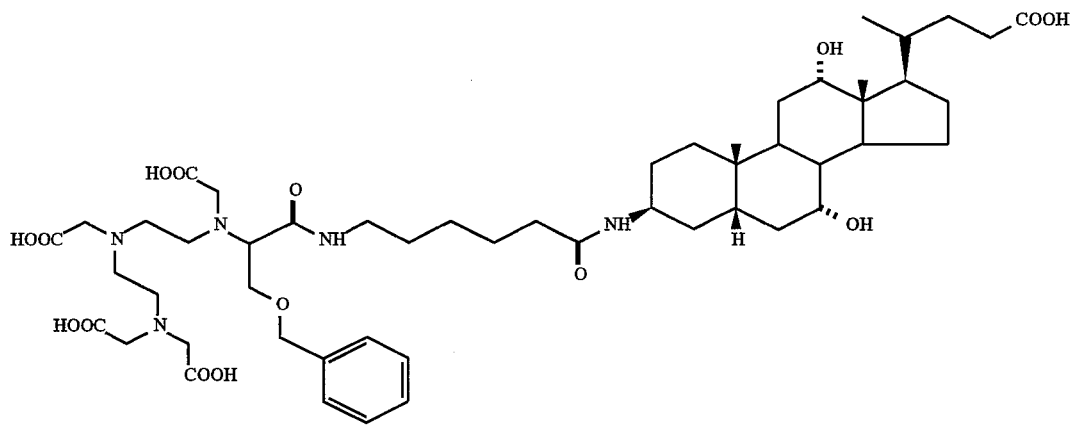

(3β,5β,7α,12α)-3-[[17-carboxy-10,13,16-tris (carboxymethyl)-1,8-dioxo-9-[(phenylmethoxy)methyl]-7,10, 13,16-tetraazaheptadecyl]amino]-7,12-dihydroxy-cholan-24-oic acid

COMPOUND 21 (EXAMPLE 4)

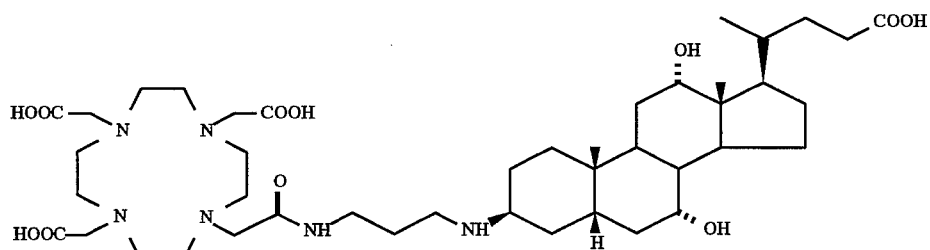

(3β,5β,7α,12α)-7,12-dihydroxy-3-[[3-[[[4,7,10-tris(carboxymethyl)-1,4,7,10-tetraazacyclododec-1-yl]acetyl]-amino]propyl]amino]-cholan-24-oic acid

COMPOUND 22 (EXAMPLE 9)

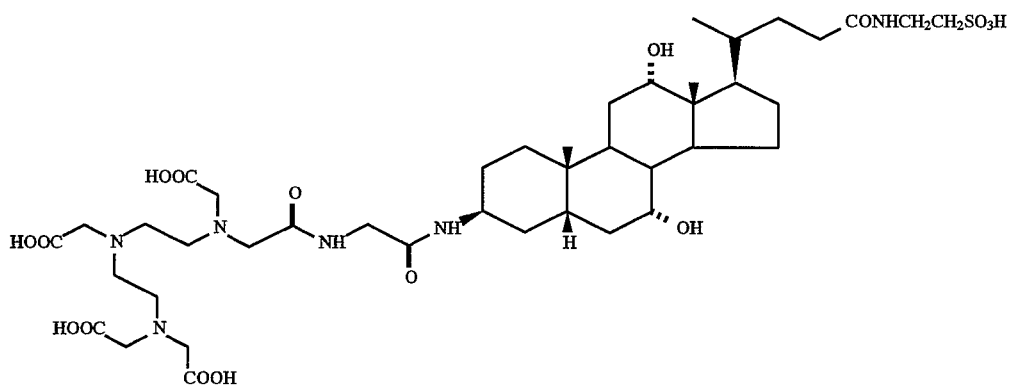

3,6,9-tris(carboxymethyl)-14-[[(3β,5β,7α,12α)-7,12-dihydroxy-24-oxo-24-[(2-sulfoethyl)amino]-cholan-3-yl]-amino]-11,14-dioxo-3,6,9,12-tetraazatetradecanoic acid -continued
COMPOUND 23 (EXAMPLE 9)
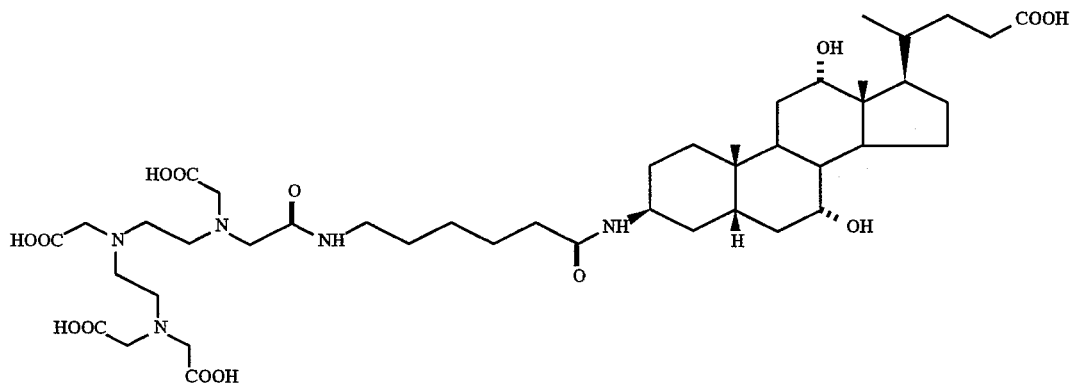
[(3β,5β,7α,12a)-3-[[17-carboxy-10,13,16-tris (carboxymethyl)-1,8-dioxo-7,10,13,16-tetraazaheptadecyl]amino]-7,12-dihydroxy-cholan-24-oic acid
COMPOUND 24 (EXAMPLE 9)
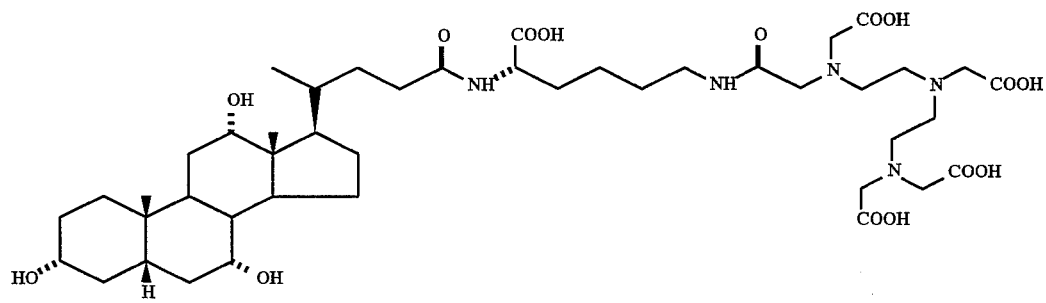
(17S)-3,6,9-tris(carboxymethyl)-11-oxo-17-[[(3β,5β,-7α,12a)-3,7,12-trihydroxy-24-oxocholan-24-yl]amino]-3,6,9,12-tetraazaoctadecanedioic acid
COMPOUND 25 (EXAMPLE 14)
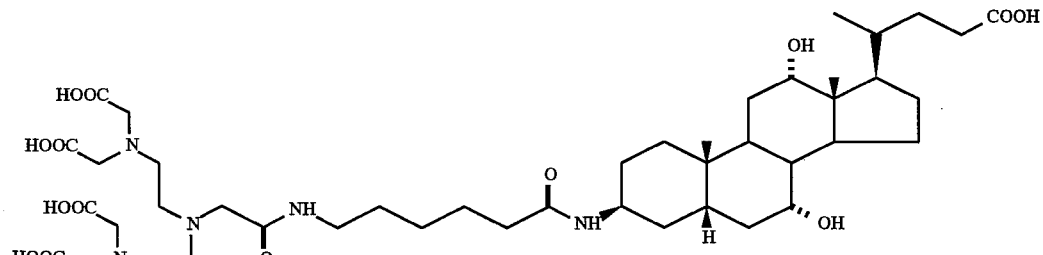
[[(3β,5β,7α,12a)-3-[[6-[[[bis[2-[bis (carboxymethyl) amino]ethyl]amino]acetyl]amino]-1-oxohexyl]amino]-7,12-dihydroxy-cholan-24-oic acid -continued

COMPOUND 26 (EXAMPLE 14)

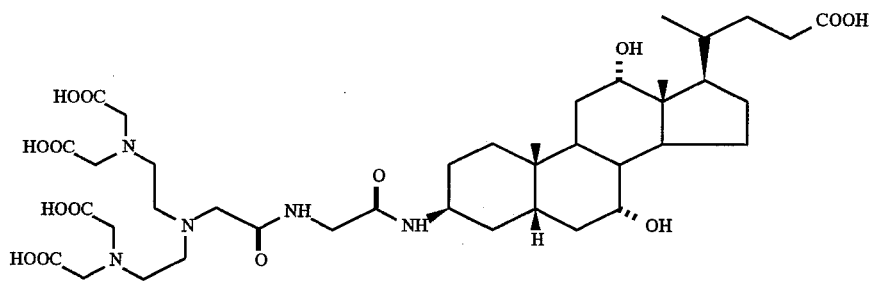

(3β,5β,7α,12a)-3-[[[[[bis[2-[bis(carboxymethyl) amino]-ethyl]amino]acetyl]amino]acetyl]amino]-7,12-dihydroxy-cholan-24-oic acid

COMPOUND 27 (EXAMPLE 14)

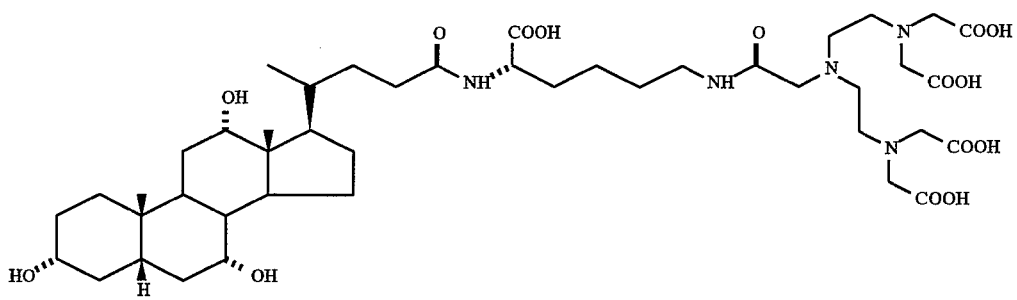

$N^6$-[[bis[2-[bis(carboxymethyl) amino]ethyl]amino]acetyl]-$N^2$-[(3α,5β,7α,12a)-3,7,12-trihydroxy-24-oxocholan-24-yl]-L-lysine

COMPOUND 28 (EXAMPLE 15)

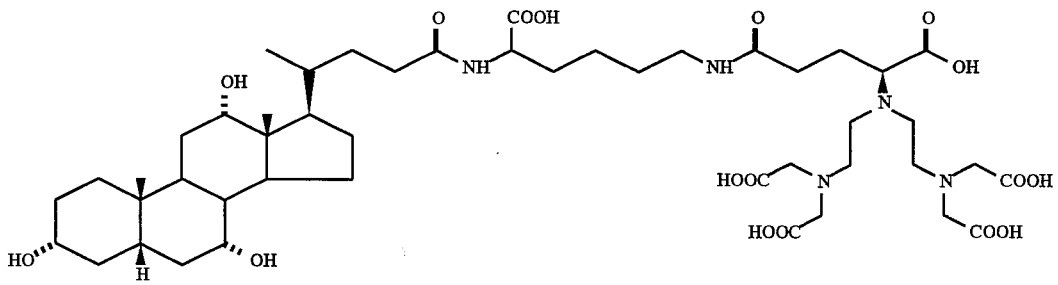

[[$N^6$-[(4S)[4-[bis[2-[bis(carboxymethyl) amino]ethyl]amino]-4-carboxy]-1-oxobutyl]-$N^2$-[(3α,5β,7α,12a)-3,7,12-trihydroxy-24-oxocholan-24-yl]-L-lysine

COMPOUND 29 (EXAMPLE 15)

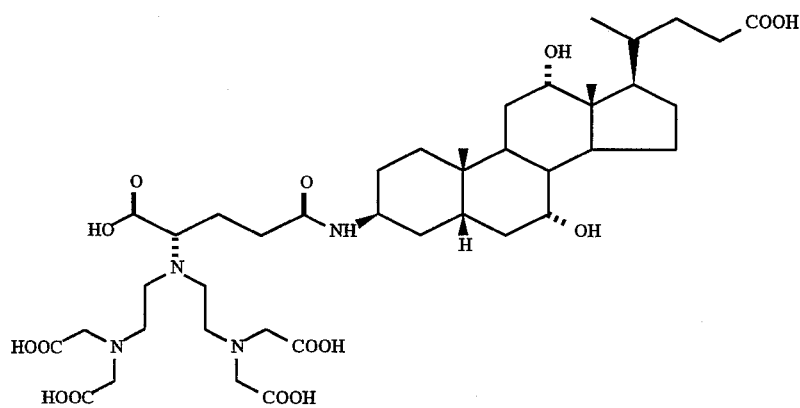

[3β(S),5β,7α,12a]-3-[4-carboxy-4-[bis[2-[bis (carboxymethyl)amino]ethyl]amino]-1-oxobutyl]amino]-7,12-dihydroxy-cholan-24-oic acid

COMPOUND 30 (EXAMPLE 16)

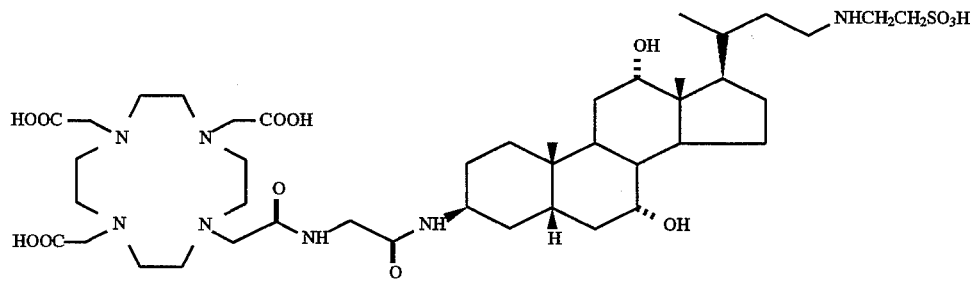

[[10-[2-[[2-[[(3β,5β,7α,12a)-7,12-dihydroxy-24-oxo-24-[(2-sulfoethyl)amino]cholan-3-yl]amino]-2-oxoethyl]amino]-2-oxoethyl]-1,4,7,10-tetraazacyclododecane-1,4,7-triacetic acid

COMPOUND 31 (EXAMPLE 16)

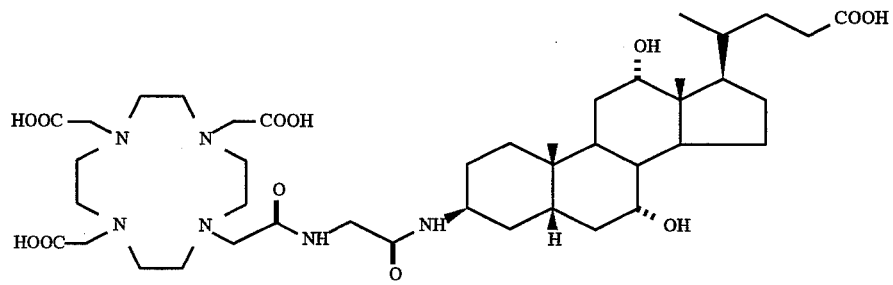

(3β,5β,7α,12a)-3-[[[[[4,7,10-tris (carboxymethyl)-1,4,7,10-tetraazacyclododecyl]acetyl]amino]acetyl]amino]-7,12-dihydroxy-cholan-24-oic acid

COMPOUND 32 (EXAMPLE 16)
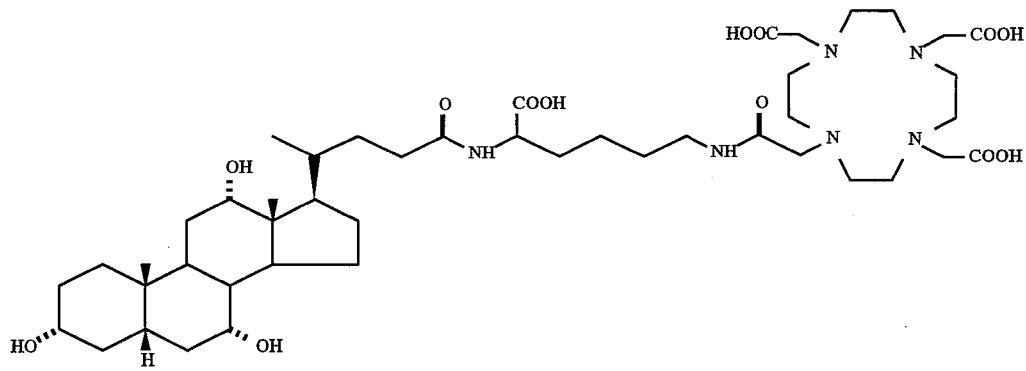
N²-[(3α,5β,7α,12a)-3,7,12-trihydroxy-24-oxocholan-24-yl]-N⁶-[[4,7,10-tris(carboxymethyl)-1,4,7,10-tetraaza-cyclododecyl]acetyl]-L-lysine
COMPOUND 33 (EXAMPLE 16)
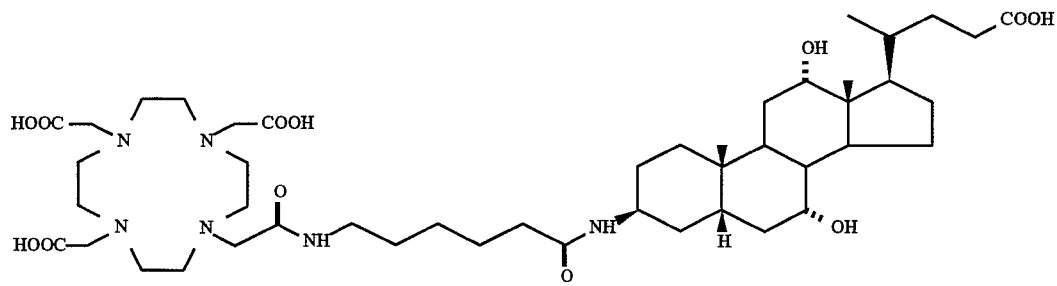
(3β,5β,7α,12a)-3-[[6-[[[4,7,10-tris (carboxymethyl)-1,4,7,10-tetraazacyclododecyl]acetyl]amino]-1-oxohexyl]amino]-7,12-dihydroxy-cholan-24-oic acid
COMPOUND 34 (EXAMPLE 17)
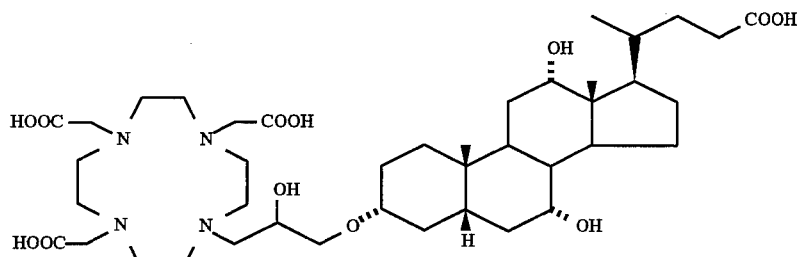
[[(3α,5β,7α,12a)-3-[[3-[4,7,10-tris (carboxymethyl)-1,4,7,10-tetraazacyclododecyl]-2-hydroxypropyl]oxy]-7,12-dihydroxy-cholan-24-oic acid -continued
COMPOUND 35 (EXAMPLE 18)

[[(3β,5β,7α,12a)-3-[[5-[4,7,10-tris (carboxymethyl)-
1,4,7,10-tetraazacyclododecyl]-4-hydroxy-1-oxopentyl]-
amino]-7,12-dihydroxy-cholan-24-oic acid It is intended that all the matter contained in the following section shall be interpreted as illustrative and not in a limiting sense.

EXAMPLE 1

[[4-Carboxy-5,8,11-tris(carboxymethyl)-1-[4-[[[[(3α,5β, 7α,12α)-3,7,12-trihydroxy-24-oxocholan-24-yl]amino] acetyl]amino]phenyl]-2-oxa-5,8,11-triazatridecan-13-oate (5⁻)]gadolinate(2⁻)] hydrogen compound with 1-deoxy-1-(methylamino)-D-glucitol (1:2)

A) N-[2-[(2-aminoethyl)amino]ethyl]-O-(4-nitrophenyl) methyl-D,L-serine t-butyl ester A solution of 14 g of t-butyl 2-bromo-3-[(4-nitrophenyl) methoxy]propanoate (prepared according to the procedure described by P. L. Rings et al., Synth. Commun., 1993, 23, 2639) (0.0389 mol), in 30 ml of acetonitrile was added to a solution of 20 g of diethylenetriamine (0.19 mol) in 20 ml of acetonitrile kept at 0°–5° C. and under inert atmosphere. The solution was then heated to 35° C. for 4 h. The solvent was evaporated under vacuum and 100 ml of a NaCl saturated solution were added to the residue. The solution was extracted with $Et_2O$; the organic phase was washed with $H_2O$, dried and concentrated under vacuum to obtain 12 g of the desired product (0.031 mol).

Yield: 80%

TLC: Carrier: silica gel plates 60 $F_{254}$ Merck

Eluent: $CHCl_3$: $CH_3OH$ : 25% $NH_4OH$ (w/w)=10:2:0.5 (v/v/v)

Detector: 0.5% $KMnO_4$ in 0.1N NaOH $R_f$=0.5

The $^1H$-NMR, $^{13}C$-NMR, IR and MS spectra are consistent with the indicated structure.

B) 4-[(1,1-dimethylethoxy)carbonyl]-5,8,11-tris[2-(1,1-dimethylethoxy)-2-oxoethyl]-1-(4-nitrophenyl)-2-oxa-5,8, 11-triazatridecan-13-oic acid 1,1-dimethylethyl ester A solution of 11 g of compound A) (0.029 mol) and 31.17 g of diisopropylethylamine (0.29 mol) in 50 ml of 1,2-dichloroethane, kept at 0°–5° C. and under inert atmosphere, was added to 28.28 g of t-butyl bromoacetate (0.145 mol). The reaction mixture was kept under stirring at room temperature for 16 h. After cooling to 0° C., the solution was filtered and the solvent was evaporated under reduced pressure. The residue was taken up into AcOEt and $H_2O$. After evaporation of the solvent, the residue was purified by column chromatography, to obtain 14.8 g of the desired product (0.018 mol).

Yield: 62%

TLC: Carrier: silica gel plates 60 $F_{254}$ Merck

Eluent: n-hexane: EtOAc=7:3 (v/v)

Detector: 0.5% $KMnO_4$ in 0.1N NaOH $R_f$=0.5

The $^1H$-NMR, $^{13}C$-NMR, IR and MS spectra are consistent with the indicated structure.

C) 4-[(1,1-dimethylethoxy)carbonyl]-5,8,11-tris[2-(1,1-dimethylethoxy)-2-oxoethyl]-1-(4-aminophenyl)-2-oxa-5,8, 11-triazatridecan-13-oic acid 1,1-dimethylethyl ester A solution of 13.7 g of compound B) (0.0163 mol) in 200 ml EtOH was added to 1.37 g of 10% palladium carbon and the mixture was hydrogenated at room temperature and normal pressure for 1 h. The suspension was filtered from the catalyst through Millipore® (0.5 µm) and the solvent was evaporated under reduced pressure. The residue was purified by flash chromatography to obtain 10.7 g of the desired product (0.0132 mol).

Yield: 81%

HPLC titre: 99% (% area)

Stationary phase: column E. Merck Lichrosorb Select B 5 µm; 250×4 mm

| Mobile phase: gradient elution | | |
|---|---|---|
| min | % A | % B |
| 0 | 95 | 5 |
| 30 | 20 | 80 |
| 35 | 95 | 5 |

A = aqueous solution 0.01 M $KH_2PO_4$ and 0.017 M $H_3PO_4$
B = $CH_3CN$

Flow rate: 1 ml min⁻¹

Temperature: 45° C.

Detector (UV): 245 nm

TLC: Carrier: silica gel plates 60 $F_{254}$ Merck

Eluent: n-hexane: $Et_2O$: i-PrOH=70:25:5 (v/v/v)

Detector: UV lamp (254 nm) $R_f$=0.15

The $^1H$-NMR, $^{13}C$-NMR, IR and MS spectra are consistent with the indicated structure.

D) 4-[(1,1-dimethylethoxy)carbonyl]-5,8,11-tris[2-(1,1-dimethylethoxy)-2-oxoethyl]-1-[4-[[[[(1,1-dimethylethoxy) carbonyl]amino]acetyl]amino]phenyl]-2-oxa-5,8,11-triazatridecan-13-oic acid 1,1-dimethylethyl ester A solution of 4.95 g of compound C) (0.0061 mol), and 2.13 g of N-(t-butoxycarbonyl)glycine (marketed product) (0.0122 mol) and 1.35 g of triethylamine (0.0134 mol) in 50 ml of DMF, kept under stirring at 0° C., was added drop by drop to 2.18 g of diethoxyphosphoryl cyanide (0.0134 mol), under are inert atmosphere, in 15 minutes. When the addition was over, the mixture was left to warm to room temperature. After 120 h the mixture was diluted with AcOEt and washed with a NaCl saturated solution. The organic phase was then washed with a 10-$^{5N}$ HCl solution, with $H_2O$ and evaporated under reduced pressure. The residue was purified by flash chromatography to obtain 3.02 g of the desired product (0.0031 mol).

Yield: 51%

HPLC titre: 98% (in % area)

Stationary phase: column E. Merck Lichrosorb Select B, 5 μm; 250×4 mm

| Mobile phase: gradient elution | | |
|---|---|---|
| min | % A | % B |
| 0 | 95 | 5 |
| 30 | 20 | 80 |
| 45 | 20 | 80 |

A = aqueous solution 0.01 M $KH_2PO_4$ and 0.017 M $H_3PO_4$
B = $CH_3CN$

Flow rate: 1 ml min$^{-1}$

Temperature: 45° C.

Detector (UV): 245 nm

TLC: Carrier: silica gel plates 60 $F_{254}$ Merck

Eluent: n-hexane: $Et_2O$: i-PrOH=70:25:5 (v/v/v)

Detector: UV lamp (254 nm) $R_f$=0.15

The $^1$H-NMR, $^{13}$C-NMR, IR and MS spectra are consistent with the indicated structure.

E) 4-Carboxy-5,8,11-tris(carboxymethyl)-1-[4-[[[[-(3α, 5β,7α,12α)-3,7,12-trihydroxy-24-oxocholan-24-yl]amino]acetyl]amino]phenyl]-2-oxa-5,8,11-triazatridecan-13-oic acid A solution of 35.09 g of compound D) (0.036 mol) and 270 ml of anisole in 340 ml of $CH_2Cl_2$ was added drop by drop, at 0° C., to 167 ml of trifluoroacetic acid in a period of 2 h. When the addition was over the mixture was left to warm to room temperature reacting for a 3 day total time. The reaction mixture was evaporated under reduced pressure. The residue was taken up into $CH_2Cl_2$. The residue was then suspended in $H_2O$, neutralized at 0° C. with 25% $NH_4OH$ (w/w) and extracted with ethyl ether. The aqueous phase was evaporated under reduced pressure to obtain a residue that was purified by flash chromatography. The resulting solid was dissolved at room temperature in a $H_2O$/DMF mixture (5:8=v/v) and reacted with 21.85 g of cholic acid N-succinimidyl ester (prepared according to the procedure described by Okahata, Y; Ando, R.; Kunitake, T., Bull. Chem. Soc. Jpn., 1979, 52, 3647–3653) (0.043 mol) added in small portions to the solution. After 30 h the reaction mixture was evaporated under reduced pressure and the residue was purified by flash chromatography. The product was dissolved in 1N HCl and eluted through an Amberlite® XAD-16 polystyrene resin, to obtain 10.08 g of the desired product (0.010 mol).

Yield: 29% m.p.: 154°–156° C. (dec.)

K.F. titre: 1.79% (w/w)

HPLC titre: 98% (in % area)

Stationary phase: column E. Merck Lichrosorb Select B, 5 μm; 250×4 mm

| Mobile phase: gradient elution | | |
|---|---|---|
| min | % A | % B |
| 0 | 95 | 5 |
| 30 | 20 | 80 |
| 45 | 20 | 80 |

A = aqueous solution 0.01 M $KH_2PO_4$ and 0.017 M $H_3PO_4$
B = $CH_3CN$

Flow rate: 1 ml min$^{-1}$

Temperature: 45° C.

Detector (UV): 245 nm

| Elemental analysis | C | H | N |
|---|---|---|---|
| % calc.: | 59.06 | 7.54 | 7.18 |
| % found: | 58.22 | 7.78 | 7.13 |

TLC: Carrier: silica gel plates 60 $F_{254}$ Merck

Eluent: $CH_2Cl_2$: MeOH: 25% $NH_4OH$ (w/w)=6:3:0.7 (v/v/v)

Detector: UV lamp (254 nm) or AcOH: conc. $H_2SO_4$: p-anisaldehyde $R_f$=0.21

The $^1$H-NMR, $^{13}$C-NMR, IR and MS spectra are consistent with the indicated structure.

F) Title compound 9.04 g of compound E) (8.9 mmol) were suspended in 200 ml of $H_2O$ and pH was adjusted to 6.5 with 21.9 ml of 1N meglumine (21.9 mmol) to obtain a complete dissolution. Then a solution of 3.29 g of $GdCl_3.6H_2O$ (8.9 mmol) in 40 ml of $H_2O$ was dropped therein, maintaining at the solution pH 6.5 by addition of 1N meglumine (43.7 ml total; 43.7 mmol); when pH remained constant without addition of meglumine, the mixture was filtered through a Millipore HA filter (0.45 μm) and subjected to nanofiltration. The pH of the retentate was adjusted to 7 with meglumine and the solution was concentrated to dryness. The vitreous residue was ground and dried to obtain 13 g of the desired product (8.5 mmol).

Yield: 96% m.p.: 178°–180° C. (dec.)

K.F. titre: 6.84% (w/w)

HPLC titre: 98% (in % area)

Stationary phase: Column E. Merck Superspher RP 18; 5 μm; 250×4 mm

| Mobile phase: gradient elution | | |
|---|---|---|
| min | % A | % B |
| 0 | 70 | 30 |
| 15 | 70 | 30 |
| 30 | 55 | 50 |

A = 0.05 M $KH_2PO_4$ aqueous solution adjusted to pH 3.5 with $H_3PO_4$
B = $CH_3CN$ Flow rate: 1 ml min$^{-1}$ Temperature: 40° C.

Detector (UV): 245 nm

| Elemental analysis | C | H | Gd | N | Cl |
|---|---|---|---|---|---|
| % calc.: | 48.96 | 6.89 | 10.34 | 6.45 | |
| % found: | 45.88 | 7.12 | 9.70 | 6.06 | <0.1 |

The IR and MS spectra are consistent with the indicated structure.

EXAMPLE 2

[[4-Carboxy-5,8,11-tris(carboxymethyl)-1-[4-[[(3α,5β,7α, 12α)-3,7,12-trihydroxy-24-oxocholan-24-yl]amino]phenyl] -2-oxa-5,8,11-triazatridecan-13-oate(5$^-$)]gadolinate(2$^-$)] hydrogen compound with 1-deoxy-1-(methylamino)-D-glucitol (1:2)

A) 4-[(1,1-dimethylethoxy)carbonyl]-5,8,11-tris[2-(1,1-dimethylethoxy)-2-oxoethyl]-1-[4-[[(3α,5β,7α,12α)-3,7, 12-trihydroxy-24-oxocholan-24yl]amino]phenyl]-2-oxa-5, 8,11-triazatridecan-13-oic acid 1,1-dimethylethyl ester A solution of 8.4 g of cholic acid (marketed product) (20.6 mmol) in 20 ml of DMF at 10° C., was added to 2.25 g of triethylamine (22.2 mmol) and 13.9 g of 4-[(1,1-dimethylethoxy)carbonyl]-5,8,11-tris[2-(1,1-dimethylethoxy)-2-oxoethyl-1-(4-aminophenyl)-2-oxa-5,8, 11-triazatridecan-13-oic acid 1,1-dimethylethyl ester (prepared according to the procedure described in EXAMPLE 1) (17.2 mmol) dissolved in 40 ml of DMF, to obtain a kind of gel. Then 4.19 g of diethoxyphosphoryl cyanide (23.9 mmol) in 5 ml of DMF were dropped therein, at 7° C. and in 10 min. When the addition was over, the solution was homogeneous again. After 2 h at 7° C. and 2 h at room temperature, the reaction mixture was poured into $H_2O$ and extracted with $Et_2O$. The organic phase was washed with a 5% $NaHCO_3$ solution, then with a NaCl saturated solution, dried and evaporated under reduced pressure. The residue was purified by flash chromatography to obtain 9.5 g of the desired product (7.9 mmol).

Yield: 46%

HPLC titre: 92% (in % area)

Stationary phase: Column E. Merck Lichrosorb Select B; 5 μm; 250×4 mm

| Mobile phase: gradient elution | | |
|---|---|---|
| min | % A | % B |
| 0 | 95 | 5 |
| 30 | 20 | 80 |
| 45 | 20 | 80 |

A = 0.01 M $KH_2PO_4$ and 0.017 M $H_3PO_4$ aqueous solution
B = $CH_3CN$

Flow rate: 1 ml min$^{-1}$
Temperature: 30° C.
Detector (UV): 245 nm
TLC: Carrier: silica gel plates 60 $F_{254}$ Merck
Eluent: AcOEt: i-PrOH=95:5 (v/v)
Detector: UV lamp (254 nm) $R_f$=0.42

The $^1$H-NMR, $^{13}$C-NMR, IR and MS spectra are consistent with the indicated structure.

B) 4-Carboxy-5,8,11-tris(carboxymethyl)-1-[4-[[(3α,5β, 7α,12α)-3,7,12-trihydroxy-24-oxocholan-24-yl]amino] phenyl]-2-oxa-5,8,11-triazatridecan-13-oic acid 6.05 g of compound A) (5 mmol) were dissolved in 40 ml of $CH_2Cl_2$, the solution was cooled to 0° C. and 20 ml of $CF_3COOH$ were dropped slowly (1 h). The reaction mixture was left under stirring at room temperature for 24 h, the solvent was evaporated off under reduced pressure and the residue, taken up into $CH_2Cl_2$, was evaporated again to remove completely $CF_3COOH$. The resulting residue was taken up into $CH_2Cl_2$ and purified by flash chromatography. The product was dissolved in 1N HCl and eluted through an Amberlite® XAD-16 polystyrene resin, to obtain 2.9 g of the desired product (3.15 mmol).

Yield: 60%

| Elemental analysis | C | H | N | |
|---|---|---|---|---|
| % calc.: | 60.11 | 7.68 | 6.09 | |
| % found: | 58.65 | 7.43 | 5.99 | $H_2O$ 2.20 |

TLC: Carrier: silica gel plates 60 $F_{254}$ Merck
Eluent: $CH_2Cl_2$: MeOH: 25% $NH_4OH$ (w/w)=6:3:0.7 (v/v/v)
Detector: UV lamp (254 nm) or AcOH: $H_2SO_4$ conc.: p-anisaldehyde $R_f$=0.24

The $^1$H-NMR, $^{13}$C-NMR, IR and MS spectra are consistent with the indicated structure.

C) Title compound

According to the procedure described in EXAMPLE 1, 2 g of compound B) (2.17 mmol) in 45 ml of $H_2O$, were reacted with 0.80 g of $GdCl_3.6H_2O$ (2.17 mmol), maintaining the solution at pH 6.5 by addition of 10.74 ml of 1N meglumine. 3.08 g of the desired product (2.1 mmol) were obtained.

Yield: 97%

| Elemental analysis | C | H | Gd | N | Cl |
|---|---|---|---|---|---|
| % calc.: | 49.23 | 6.88 | 10.74 | 5.74 | |
| % found: | 46.84 | 6.47 | 10.15 | 5.43 | <0.1 |

The IR and MS spectra are consistent with the indicated structure.

EXAMPLE 3

[[3,6,9-Tris(carboxymethyl)-10-(phenylmethoxy)methyl-11-oxo-14-[[(3α,5β,7α,12α)-3,7,12-trihydroxy-24-oxocholan-24-yl]amino]-3,6,9,12-tetraazatetradecanoate(4$^-$)]gadolinate(1$^-$)] hydrogen compound with 1-deoxy-1-(methylamino)-D-glucitol (1:1)

A) O-Phenylmethyl-N-[2-methoxy-2-oxoethyl]-N-[2-[[2-[bis(2-methoxy-2-oxoethyl)amino]ethyl](2-methoxy-2-oxoethyl)amino]ethyl]-D,L-serine A suspension of 40 g of 4-carboxy-5,8,11-tris (carboxymethyl)-1-phenyl-2-oxa-5,8,11-triazatridecan-13-oic acid (prepared as described in EP-A-230893) (0.07789 mol) in 400 ml of anhydrous MeOH, kept at 0° C., was added to 150 ml of thionyl chloride, in 2 h. The clear solution, heated to 25° C., was left under magnetic stirring for 30 h. The solution was evaporated to dryness and the resulting white solid, cooled in brine (−15° C.), was added to 400 ml of $Et_2O$ and, slowly and under stirring, to 500 ml of a $NaHCO_3$ saturated solution (pH 10). After separation, the aqueous phase, kept at 0° C., was acidified to pH 6.5 with 6N HCl and then extracted with EtOAc. The organic phase was evaporated to dryness. 23.4 g of the desired product (0.0411 mol) were obtained.

Yield: 53%
HPLC titre: 98% (in % area)
Stationary phase: Column E. Merck Lichrosorb Select B, 5 μm; 250×4 mm;

| Mobile phase: gradient elution | | |
|---|---|---|
| min | % A | % B |
| 0 | 95 | 5 |
| 30 | 20 | 80 |
| 45 | 20 | 80 |

A = 0.01 M $KH_2PO_4$ and 0.017 M $H_3PO_4$ aqueous solution
B = $CH_3CN$

Flow rate: 1 ml min$^{-1}$;
Temperature: 45° C.;
Detector (UV): 210 nm, 254 nm and 280 nm.
TLC: Carrier: silica gel plates 60 $F_{254}$ Merck
Eluent: $CH_2Cl_2$: MeOH=8:2 (v:v)
Detector: 0.5% $KMnO_4$ in 0.1N NaOH $R_f$=0.5
The $^1$H-NMR, $^{13}$C-NMR, IR and MS spectra are consistent with the indicated structure.

B) Methyl 3,6,9-tris(2-methoxy-2-oxoethyl)-10-(phenylmethoxy)methyl-11-oxo-14-[[(3α,5β,7α,12α)-3,7,12-trihydroxy-24-oxocholan-24-yl]amino]-3,6,9,12-tetraazatetradecanoate A solution of 39.2 g of compound A) (0.0688 mol), 33.1 g of (3α,5β,7α,12α)-N-(2-aminoethyl)-3,7,12-trihydroxycholan-24-amide (prepared according to the procedure described by Hilton, M. L.; Jones, A. S.; Westwood, J. R. B. J. Chem. Soc., 3449–3453, 1955) (0.0734 mol) and 13.33 g of diethoxyphosphoryl cyanide (0.076 mol) in 400 ml of DMF was added drop by drop, at 0° C. and in 10 minutes, to 7.69 g of triethylamine (0.076 mol). After 4 h at 0° C. and 16 h at room temperature, the reaction mixture was concentrated and poured into a $NaHCO_3$ saturated solution and extracted with AcOEt. The organic phases were combined, washed with a NaCl saturated solution, with $H_2O$, dried over $Na_2SO_4$ and evaporated under reduced pressure. The solid residue was purified by flash chromatography to obtain 25.2 g of the desired product (0.0251 mol).

Yield: 36%
HPLC titre: 91% (in % area)
Stationary phase: Column E. Merck Lichrosorb Select B, 5 μm; 250×4 mm

| Mobile phase: gradient elution | | |
|---|---|---|
| min | % A | % B |
| 0 | 95 | 5 |
| 30 | 20 | 80 |
| 45 | 20 | 80 |

A = 0.01 M $KH_2PO_4$ and 0.017 M $H_3PO_4$ aqueous solution
B = $CH_3CN$

Flow rate: 1 ml min$^{-1}$
Temperature: 30° C.
Detector (UV): 210 nm
TLC: Carrier: silica gel plates 60 $F_{254}$ Merck
Eluent: $CH_2Cl_2$: MeOH: 25% $NH_4OH$ (w/w)=9:1:0.1 (v/v/v)
Detector: AcOH: Conc. $H_2SO_4$: p-anisaldehyde=100:2:1 (v/v/v) $R_f$=0.34

The $^1$H-NMR, $^{13}$C-NMR, IR and MS spectra are consistent with the indicated structure.

C) Title compound 11.5 g of compound B) (11.4 mmol) were dissolved in 1:1 MeOH/$H_2O$ (300 ml) and 2N NaOH (5 ml) was added until pH 12 was reached. The reaction mixture was stirred for 48 h at room temperature maintaining a pH of 12 by addition of 1N NaOH (35 ml) through a pH-stat apparatus. The reaction was monitored by HPLC. The resulting solution was adjusted to pH 7 with 2N HCl and evaporated. The residue was dissolved With 3:7 MeOH/$H_2O$ (500 ml), acidified with 6N HCl (15 ml) and the solution was loaded onto an Amberlite® XAD-16 resin column and eluted with a MeOH/$H_2O$ gradient. Removal of the solvent from the fractions containing the product gave a solid that was further purified by reverse-phase preparative HPLC to give 2.13 g of 3,6,9-tris(carboxymethyl)-10-(phenylmethoxy)methyl-11-oxo-14-[[(3α,5β,7α,12α)-3,7,12-trihydroxy-24-oxocholan-24-yl]amino]-3,6,9,12-tetraazatetradecanoic acid (2.25 mmol) as a white solid. The acid was suspended in $H_2O$ (100 ml) and MeOH (20 ml) and 1N meglumine (5.6 ml; 5.6 mmol) was added until a complete dissolution (pH 6.8). A solution of $GdCl_3$ $6H_2O$ (0.83 g; 2.23 mmol) in $H_2O$ (20 mL) was added drop by drop to the reaction mixture, maintained at pH of 6.8 by addition of 1N meglumine (8.4 ml; 8.4 mmol). After 16 h the cloudy solution was filtered, loaded onto an Amberlite® XAD-16 resin column and eluted with a MeOH/$H_2O$ gradient. The fractions containing the chelate were concentrated to dryness under reduced pressure to give the desired product (2.0 g; 1.5 mmol).

Yield 13% m.p.=>300
K.F. titre: 4.56% (w/w)
HPLC titre: 98% (in % area)
Stationary phase: Column E. Merck Superspher RP-18; 250×4 mm

| Mobile phase: gradient elution | | |
|---|---|---|
| min | % A | % B |
| 0 | 70 | 30 |
| 30 | 50 | 50 |

A = aq. 0.05 M $KH_2PO_4$
B = $CH_3CN$

Flow rate: 1 ml min$^{-1}$
Temperature: 40° C.
Detector (UV): 210 nm

| Elemental analysis | | | | | |
|---|---|---|---|---|---|
| | C | H | N | Gd | |
| % calc.: | 50.99 | 6.92 | 6.48 | 12.14 | |
| % found: | 49.26 | 7.26 | 6.20 | 11.57 | $H_2O$ < 0.1 |

The IR and MS spectra are consistent with the structure.

EXAMPLE 4

[[10-[2-Oxo-2-[[3-[[2-[[(3α,5β,7α,12α)-3,7,12-trihydroxy-24-oxocholan-24-yl]amino]ethyl]amino]propyl]amino]ethyl]-1,4,7,10-tetraazacyclododecan-1,4,7-triacetoate-(3$^-$)] gadolinate(0)] hydrogen compound with HCl (1:1)

A) 2-(2-Aminoethyl)-1,3-dioxolane

A suspension of 50 g of 2-(2-bromoethyl)-1,3-dioxolane (product known in literature, CAS RN=575435-8) (0.27 mL, 32.5 mol), 62.5 g of potassium phthalimide (0.34 mol), 9.16 g of $Bu_4N^+HSO_4^-$ (0.027 mol) in 150 ml of toluene was heated to 100° C. and under $N_2$ stream for 3 h. After cooling to room temperature, the mixture was filtered and evaporated to dryness. By crystallization of the residue from abs. EtOH the phthalimido derivative was obtained. A solution of 58.5 g of $NH_2NH_2.H_2O$ (1.17 ml; 56.8 mol), 64.36 g of phthalimido derivative (0.26 mol) in 2 l of abs. EtOH was heated to reflux under $N_2$ stream for 2.5 h. After cooling to 0° C., the precipitated phthalhydrazide was filtered through a sintered funnel. By evaporation of the filtrate to dryness, 23.26 g of the desired product (0.198 mol) were obtained.

Yield: 73%

| Elemental analysis | C | H | N |
| --- | --- | --- | --- |
| % calc.: | 51.25 | 9.48 | 11.94 |
| % found: | 49.27 | 9.77 | 10.53 |

The $^1$H-NMR, $^{13}$C-NMR, IR and MS spectra are consistent with the indicated structure.

B) 2-[2-[(2-chloro-1-oxoethyl)amino]ethyl]-1,3-dioxolane

A solution of 23.0 g of compound A) (0.196 mol) and 19.8 g of $Et_3N$ (0.196 mol; 27.16 ml) in 90 ml of $CHCl_3$ under $N_2$ stream was added to a solution of 22.17 g of chloroacetyl chloride (0.196 mol; 15.6 ml) in 60 ml of $CHCl_3$ keeping the temperature at 0°–10° C. When the reaction was completed, the reaction mixture was washed with $H_2O$ and the aqueous phase was extracted with $CHCl_3$. The combined organic phases were dried and evaporated to dryness. By crystallization of the residue from $Et_2O$, 30.6 g of the desired product (0.158 mol) were obtained.

Yield: 81% m.p.: 62°–63° C. (dec.)

| Elemental analysis | C | H | Cl | N |
| --- | --- | --- | --- | --- |
| % calc.: | 43.40 | 6.25 | 18.30 | 7.23 |
| % found: | 43.13 | 6.22 | 18.28 | 7.20 |

The $^1$H-NMR, $^{13}$C-NMR, IR and MS spectra are consistent with the indicated structure.

C) N-[2-(1,3-dioxolan-2-yl)ethyl]-1,4,7,10-tetraazacyclododecane-1-acetamide

A solution of 203.3 g of 1,4,7,10-tetraazacyclododecane (marketed product) (1.18 mol) in 2 l $CH_3CN$ was added at 80° C. and under $N_2$ stream to a solution of 23 g of compound B) (0.118 mol) in 500 ml of $CH_3CN$ in 2 h. When the reaction was over, the reaction mixture was concentrated and the precipitate (1,4,7,10-tetraazacyclododecane excess) was filtered off. The residue was evaporated to dryness and purified by column chromatography to obtain 36 g of the desired product (0.109 mol).

Yield: 93%

| Elemental analysis | C | H | N |
| --- | --- | --- | --- |
| % calc.: | 54.67 | 9.50 | 21.26 |
| % found: | 54.18 | 9.49 | 20.91 |

TLC: Carrier: silica gel plates 60 $F_{254}$ Merck
Eluent: $CHCl_3$: MeOH: $NH_4OH$=4:4:2
Detector: UV lamp (254 nm) or $KMnO_4$ in NaOH $R_f$=0.3
The $^1$H-NMR, $^{13}$C-NMR, IR and MS spectra are consistent with the indicated structure.

D) 10-[2-oxo-2-[(3-oxopropyl)amino]ethyl]-1,4,7,10-tetraazacyclododecane-1,4,7-triacetic acid 48.6 g of bromoacetic acid (0.35 mol) were dissolved in 40 ml of $H_2O$ and, keeping the temperature <10° C., the pH of the solution was adjusted to 5 by addition of 175 ml of 2N NaOH. The solution, after addition of 35 g of compound C) (0.106 mol), was heated to 50° C. for 5 h, maintaining the solution at pH 10 by addition of 160 ml of 2N NaOH (0.32 mol). The reaction mixture was added to 30 ml of 37% HCl to pH 2 and the solution was heated for 2 h at 50° C. The reaction mixture was salted off by electrodialysis and after evaporating the aqueous solution and drying the residue, 40 g of the desired product (0.087 mol) were obtained.

Yield: 82% m.p.: 115°–120° C.

K.F. titre: 8.81% (w/w)

| Elemental analysis | C | H | N |
| --- | --- | --- | --- |
| % calc.: | 49.66 | 7.25 | 15.24 |
| % found: | 45.30 | 8.09 | 13.38 |

The $^1$H-NMR, $^{13}$C-NMR, IR and MS spectra are consistent with the indicated structure.

E) 10-[2-Oxo-2-[[3-[[2-[[(3α,5β,7α,12α)-3,7,12-trihydroxy-24-oxocholan-24-yl]amino]ethyl]amino]propyl]amino]ethyl]-1,4,7,10-tetraazacyclododecan-1,4,7-triacetic acid A solution of 80 g of N-(2-aminoethyl)-(3α,5β,7α,12α)-3,7,12-trihydroxycholan-24-amide (prepared according to the procedure described by Hilton, M. L.; Jones, A. S.; Westwood, J. R. B., J. Chem. Soc. 1955, 3449–3453) (178 mmol) in 800 ml of anhydrous MeOH was added to 16.31 g of compound (D) (36 mmol), 35 ml of 1N HCl (35 mmol) and 1.49 g of $NaBH_3CN$ (24 mmol). The solution was kept under nitrogen and magnetic stirring and in the presence of molecular sieves (0.4 nm). After 50 h the solvent was evaporated off under reduced pressure to obtain a crude product that was purified by flash chromatography. The product was dissolved in 1N HCl and eluted through an Amberlite® XAD-16 polystyrene resin, to obtain 8.79 g of the desired product (9.8 mmol).

Yield: 28% m.p.: 154° C.

K.F. titre: 10.64% (w/w)

HPLC titre: 98.9% (in % area)

Stationary phase: Column E. Merck Lichrosorb Select B; 5 μm; 250×4 mm

| Mobile phase: gradient elution | | |
| --- | --- | --- |
| min | % A | % B |
| 0 | 95 | 5 |
| 30 | 20 | 80 |
| 45 | 20 | 80 |

A = 0.01 M $KH_2PO_4$ and 0.017 M $H_3PO_4$ aqueous solution
B = $CH_3CN$

Flow rate: 1 ml min$^{-1}$

Temperature: 45° C.

Detector (UV): 210 nm

| Elemental analysis | C | H | N |
|---|---|---|---|
| % calc.: | 60.44 | 8.91 | 10.97 |
| % found: | 53.72 | 9.49 | 9.51 |

TLC: Carrier: silica gel plates 60 $F_{254}$ Merck

Eluent: $CH_2Cl_2$: MeOH: 25% $NH_4OH$ (w/w)=7:3:1 (v/v/v)

Detector: AcOH: Conc. $H_2SO_4$: p-anisaldehyde=100:2:1 (v/v/v) $R_f$=0.26

The $^1$H-NMR, $^{13}$C-NMR, IR and MS spectra are consistent with the indicated structure.

F) Title compound

A solution of 6.40 g of compound (E) (7.2 mmol) in 60 ml of $H_2O$, kept at 50° C. with stirring and under nitrogen atmosphere, was added to 1.18 g of $GdO_3$ (3.3 mmol). The pH before the addition of the oxide was 6.65. After that, 1N HCl (7.2 ml) was added and pH was lowered to 2.75. The solution was filtered through a Millipore filter (HAS 0.45 μm) and the solvent was evaporated off under reduced pressure, to obtain 6.90 g of the desired product (6.36 mmol).

Yield: 88.34% m.p.: 294° C. (dec.)

| Elemental analysis | C | H | N | Gd | Cl | |
|---|---|---|---|---|---|---|
| % calc.: | 49.82 | 7.15 | 9.04 | 14.50 | 3.27 | |
| % found: | 47.37 | 7.78 | 8.45 | 13.53 | 3.09 | $H_2O$ 6.44 |

TLC: Carrier: silica gel plates 60 $F_{254}$ Merck

Eluent: $CHCl_3$: MeOH: $H_2O$: $Et_3N$=8:2:0.1:0.1

Detector: AcOH: Conc. $H_2SO_4$: p-anisaldehyde=100:2:1 (v/v/v) $R_f$=0.13

The IR and MS spectra are consistent with the indicated structure.

In the same way, the gadolinium complexes of the following ligands were prepared:

(3β,5β,7α,12α)-7,12-dihydroxy-3-[[[[3-[[[4,7,10-tris(carboxymethyl)-1,4,7,10-tetraazacyclodec-1-yl]acetyl]amino]propyl]amino]acetyl]amino]-cholan-24-oic acid (Compound 8);

(3β,5β,7α,12α)-7,12-dihydroxy-3-[[3-[[[4,7,10-tris(carboxymethyl)-1,4,7,10-tetraazacyclododec-1-yl]acetyl]amino]propyl]amino]-cholan-24-oic acid (Compound 21).

EXAMPLE 5

[[(3β,5β,7α,12α)-3-[[13-carboxy-6,9,12-tris(carboxymethyl)-1,4-dioxo-5-[(phenylmethoxy)methyl]-3,6,9,12-tetraazatridecyl]amino]-7,12-dihydroxy-cholan-24-oate(5⁻)]gadolinate(2⁻)] hydrogen compound with 1-deoxy-1-(methylamino)-D-glucitol (1:2)

A) (3β,5β,7α,12α)-3-azido-7,12-dihydroxy-cholan-24-oic acid methyl ester

A solution of 2.06 g of cholic acid methyl ester (marketed product) (4.87 mmol), 1.28 g of triphenylphosphine (4.88 mmol) and 1.70 g of diethylazadicarboxylate (0.76 mL, 4.88 mmol) in 50 ml of THF, at room temperature and under inert atmosphere, was added to a solution of 1.4 g of diphenylphosphorylazide (1.1 mL, 5.11 mmol) in 5 ml of THF during 15 minutes. After 24 hours at room temperature, 1 equivalent of diethylazadicarboxylate (0.76 mL, 4.88 mmol) and 1 equivalent of triphenylphosphine (1.28 g, 4.88 mmol) were added. After a further 24 hours the solvent was evaporated off under reduced pressure and the resulting crude was purified by flash chromatography. 1.6 g of the desired product (3.57 mmol) was obtained.

Yield: 73%

| Elemental analysis | C | H | N | |
|---|---|---|---|---|
| % calc.: | 67.08 | 9.23 | 9.38 | |
| % found: | 66.86 | 9.30 | 9.15 | $H_2O$ 0.74 |

TLC: Carrier: silica gel plates 60 $F_{254}$ Merck

Eluent: AcOEt: hexane=1:1

Detector: AcOH: Conc. $H_2SO_4$: p-anisaldehyde=100:2:1 (v/v/v) $R_f$=0.56

The $^1$H-NMR, $^{13}$C-NMR, IR and MS spectra are consistent with the indicated structure.

B) (3β,5β,7α,12α)-3-amino-7,12-dihydroxy-cholan-24-oic acid methyl ester

A solution of 28.28 g of compound A) ester methyl (0.063 mol) in 100 ml of THF was added to 5 ml of $H_2O$ and 16.59 g of triphenylphosphine (0.063 mol). After 96 h at room temperature, the reaction mixture was evaporated under reduced pressure and the residue was purified by flash chromatography, to obtain 23.21 g of the desired product (0.055 mol).

Yield 87%.

| Elemental analysis | C | H | N | |
|---|---|---|---|---|
| % calc.: | 71.29 | 10.39 | 3.32 | |
| % found: | 70.06 | 10.57 | 3.41 | $H_2O$ 0.26 |

TLC: Carrier: silica gel plates 60 $F_{254}$ Merck

Eluent: MeOH: $Et_3N$=95:5

Detector: AcOH: Conc. $H_2SO_4$: p-anisaldehyde=100:2:1 (v/v/v) $R_f$=0.36

The $^1$H-NMR, $^{13}$C-NMR, IR and MS spectra are consistent with the indicated structure.

C) (3β,5β,7α,12α)-3-[[[[(phenylmethoxy)carbonyl]amino]acetyl]amino]-7,12-dihydroxy-cholan-24-oic acid methyl ester A solution of 12.25 g of carbobenzyloxyglycine (marketed product) (58.5 mmol) and 6 g of N-methylmorpholine (59.3 mmol) in 400 ml of THF was added drop by drop, under nitrogen and at −4° C., to 8 g of isobutyl chloroformate (58.4 mmol) and subsequently 21.8 g of compound B) (51.7 mmol) dissolved in 100 ml of THF. After 30 min at −4° C. the reaction mixture was filtered and evaporated under reduced pressure. The residue was taken up into $Et_2O$ and $H_2O$; the organic phase was separated, washed with $H_2O$, dried over $Na_2SO_4$ and evaporated under reduced pressure. The solid residue was purified by flash chromatography, to obtain 27.9 g of the desired product (45.5 mmol).

Yield: 88%.

| Elemental analysis | C | H | N | |
|---|---|---|---|---|
| % calc.: | 68.59 | 8.55 | 4.57 | |
| % found: | 68.27 | 8.74 | 4.52 | $H_2O$ 0.25 |

TLC: Carrier: silica gel plates 60 $F_{254}$ Merck

Eluent: MeOH: $Et_3N$=95:5

Detector: AcOH: Conc. $H_2SO_4$: p-anisaldehyde=100:2:1 (v/v/v) $R_f$=0.85

The $^1$H-NMR, $^{13}$C-NMR, IR and MS spectra are consistent with the indicated structure.

D) (3β,5β,7α,12α)-3-(aminoacetyl)amino-7,12-dihydroxy-cholan-24-oic acid methyl ester A solution of compound C) methyl ester in MeOH was added to 10% Pd/C and the mixture was hydrogenated at room temperature and pressure, to obtain the desired product.

E) (3β,5β,7α,12α)-3-[[13-carboxy-6,9,12-tris (carboxymethyl)-1,4-dioxo-5-[(phenylmethoxy)methyl]-3,6,9,12-tetraaazatridecyl]amino]-7,12-diidroxycholan-24-oic acid According to the procedure described in EXAMPLE 3, O-Phenylmethyl-N-[2-methoxy-2-oxoethyl]-N-[2-[[2-[bis-(2-methoxy-2-oxoethyl)amino]ethyl](2-methoxy-2-oxoethyl)amino]ethyl]-D,L-serine and compound D) were condensed, in DMF and triethylamine, with diethoxyphosphoryl cyanide. When the reaction was over, the reaction mixture was poured into a $NaHCO_3$ saturated solution and extracted with AcOEt. The organic phases were combined and evaporated under reduced pressure. The residue was dissolved in MeOH and hydrolysed with a LiOH monohydrate aqueous solution. The reaction mixture was evaporated to dryness, the solid residue was dissolved in 1N HCl and eluted through an Amberlite® XAD-16 polystyrene resin, to obtain the desired product.

The $^1$H-NMR, $^{13}$C-NMR, IR and MS spectra are consistent with the indicated structure.

F) Title compound

According to the procedure described in EXAMPLE 1, maintaining at pH 6.5 by addition of 1N meglumine. The desired product was obtained.

The IR and MS spectra are consistent with the indicated structure.

In the same way, the gadolinium complexes of the following ligands were prepared:

3,6,9-Tris(carboxymethyl)-14-[[(3β,5β,7α,12α)-7,12-dihydroxy-24-oxo-24-[(2-sulfoethyl)amino]cholan-3-yl]amino]-11,14-dioxo-10-(phenylmethoxy)methyl-3,6,9,12-tetraazatetradecanoic acid (COMPOUND 15);

N-[(3β,5β,7α,12α)-3-[[13-carboxy-6,9,12-tris (carboxymethyl)-1,4-dioxo-5-[(phenylmethoxy) methyl]-3,6,9,12-tetraazatridecyl]amino]-7,12-dihydroxy-24-oxocholan-24-yl]glycine (COMPOUND 16);

(3β,5β,7α)-3-[[13-carboxy-6,9,12-tris(carboxymethyl)-1,4-dioxo-5-[(phenylmethoxy)methyl]-3,6,9,12-tetraazatridecyl]amino]-7-hydroxy-cholan-24-oic acid (COMPOUND 17);

(3β,5β,12α)-3-[[13-carboxy-6,9,12-tris(carboxymethyl)-1,4-dioxo-5-[(phenylmethoxy)methyl]-3,6,9,12-tetraazatridecyl]amino]-12-hydroxy-cholan-24-oic acid (COMPOUND 18);

(3β,5β)-3-[[13-carboxy-6,9,12-tris(carboxymethyl)-1,4-dioxo- 5-[(phenylmethoxy)methyl]-3,6,9,12-tetraazatridecyl]amino]-cholan-24-oic acid (COMPOUND 19);

(3β,5β,7α,12α)-3-[[17-carboxy-10,13,16-tris (carboxymethyl)-1,8-dioxo-9-[(phenylmethoxy) methyl]-7,10,13,16-tetraazaheptadecyl]amino]-7,12-dihydroxy-cholan-24-oic acid (COMPOUND 20).

EXAMPLE 6

[[(3β,5β,7α,12α)-3-[[17-carboxy-10,13,16-tris (carboxymethyl)-8-oxo-9-[(phenylmethoxy)methyl]-3,7,10,13,16-pentaazaheptadecyl]oxy]-7,12-dihydroxy-cholan-24-oate(5$^-$)]gadolinate(2$^-$)] hydrogen compound with 1-deoxy-1-(methylamino)-D-glucitol(1:2)

A) 2-Chloro-N-[2-(1,3-dioxolan-2-yl)ethyl]-3-phenylmethoxypropanamide

A solution of 69.63 g of 2-chloro-3-(phenylmethoxy) propanoyl chloride (prepared according to the procedure described in Inorg. Chem., 31, 2422, 1992) (0.299 mol) in 90 ml of $CHCl_3$ was added to a solution of 35.49 g of 2-(2-aminoethyl)-1,3-dioxolane (prepared according to the procedure described in EXAMPLE 4) (0.303 mol) and 60.3 g of triethylamine (83 ml; 0.596 mol) in 100 ml of $CHCl_3$ under inert atmosphere, keeping the temperature at 0°–5° C. The reaction mixture was stirred for 5 h at 25° C., then was washed with $H_2O$. The organic phase was dried and evaporated to dryness, the residue was purified by flash chromatography. 61.68 g of the desired product (0.197 mol) were obtained.

Yield: 66%

TLC: Carrier: silica gel plates 60 $F_{254}$ Merck

Eluent: AcOEt: n-hexane=1:1 (v/v)

Detector: 0.5% $KMnO_4$ in 0.1N NaOH $R_f$=0.34

The $^1$H-NMR, $^{13}$C-NMR, IR and MS spectra are consistent with the indicated structure.

B) 5,8,11-tris[2-(1,1-dimethylethoxy)-2-oxoethyl]-1-phenyl-4-[[2-(1,3-dioxolan-2-yl)ethyl]amino]carbonyl-2-oxa-5,8,11-triazatridecan-13-oic acid (1,1-dimethylethyl) ester 30.97 g of diethylenetriamine (0.300 mol) were added to a solution of 20.94 g of compound A) (0.067 mol) in 100 ml of MeCN under inert atmosphere and the mixture was kept at 50° C. for 72 h and at 80° C. for 8 h. After cooling to 0° C., the precipitate (diethylenetriamine hydrochloride) was filtered and washed with 50 ml of MeCN. After evaporating the solvent under reduced pressure, the diethylenetriamine excess was distilled off under vacuum. The crude product was taken up into 80 ml of AcOEt, filtered and evaporated to dryness to obtain a residue, that was purified by column chromatography [silica gel; eluent $CHCl_3$: MeOH: $NH_3$ 25% (w/w)=20:4:0.4 (v/v/v). 12.61 g of 2-[[2-[(2-aminoethyl)amino]ethyl]-3-(phenylmethoxy)-N-[2-(1,3-dioxolan-2-yl)ethyl]propanamide (0.03 mol) were obtained, that was used directly in the subsequent step (46% yield).

A solution of 7.50 g of 2-[[2-[(2-aminoethyl)amino]ethyl] amino]-3-(phenylmethoxy)-N-[2-(1,3-dioxolan-2-yl)ethyl] propanamide in 30 ml of 1,2-dichloroethane was added, under inert atmosphere, to 20.64 g of diisopropylethylamine (0.160 mol) and, keeping the temperature from 0° to 5° C., with 15.58 g of t-butyl bromoacetate (0.080 mol). The solution was kept at 15° C. for 24 h, added to further t-butyl bromoacetate (4.25 g; 0.022 mol) and kept for 72 h at 15° C. The solution was cooled to 0° C. and filtered. The filtrate was concentrated, taken up into $H_2O$ and extracted with AcOEt. The organic phase was washed with $H_2O$, dried and evaporated to dryness to obtain a crude that was purified by column chromatography [silica gel 935 g; eluent: AcOEt: n-hexane 1:1 (v/v)]. The fractions of similar purity were combined and evaporated to dryness to obtain the desired product (5.18 g; 0.062 mmol).

Yield: 34%.

Yield: 16% on two steps

TLC: Carrier: silica gel plates 60 $F_{254}$ Merck

Eluent: AcOEt: n-hexane=1:1

Detector: 0.5% $KMnO_4$ in 0.1N NaOH $R_f$=0.21

The $^1$H-NMR, $^{13}$C-NMR, IR and MS spectra are consistent with the indicated structure.

C) 5,8,11-tris(carboxymethyl)-1-phenyl-4-[(3-oxopropyl)amino]carbonyl-2-oxa-5,8,11-triazatridecan-13-oic acid 67 ml of 1N HCl (0.067 mol) were added to a solution of 14 g of compound B) (0.017 mol) in 280 ml of dioxane. The solution was diluted with 215 ml of $H_2O$, stirred at 35° C. for 54 h, then at 4° C. for 48 h. After evaporation of the dioxane, the aqueous solution was extracted with AcOEt. The organic phase was washed with $H_2O$, then dried and evaporated to dryness. The residue was taken up into $CH_2Cl_2$ and the solution was evaporated to dryness. The residue was taken up into $CH_2Cl_2$ and the solution was added, in about 1 h, to 82 g of trifluoroacetic acid (55.7 ml; 0.719 mol). The solution was kept at 5° C. for 24 h under inert atmosphere, then was evaporated to dryness. The residue was taken up into $CH_2Cl_2$ and evaporated to dryness, repeating the procedure several times. The crude product was taken up into $CH_2Cl_2$ and extracted with $H_2O$. The aqueous phase was separated, evaporated to small volume and chromatographed by HPLC. 1.5 g of the desired product (2.64 mmol) were obtained.

Yield: 16% m.p.: 100°–102° C. (dec.)

K.F. titre: 2.27% (w/w)

HPLC titre: 97% (in % area)

Stationary phase: Column E. Merck Lichrosorb RP-Select B 5 μm; 250×4 mm;

| Mobile phase: Gradient elution; A = 0.01 M $KH_2PO_4$ and 0.017 M $H_3PO_4$ aqueous solution B = A/$CH_3CN$ = 3:7 | | |
|---|---|---|
| min | % A | % B |
| 0 | 90 | 10 |
| 30 | 10 | 90 |
| 40 | 10 | 90 |

Flow rate: 1.5 ml min$^{-1}$;
Temperature: 35° C.;
Detector (UV): 210 nm.

| Elemental analysis | C | H | N | Na | Cl | $H_2O$ |
|---|---|---|---|---|---|---|
| % calc.: | 52.81 | 6.38 | 9.85 | | | |
| % found: | 51.82 | 6.34 | 9.62 | <0.10 | <0.10 | 2.27 |

The $^1$H-NMR, $^{13}$C-NMR, IR and MS spectra are consistent with the indicated structure.

D) (3β,5β,7α,12α)-3-[[17-carboxy-10,13,16-tris(carboxymethyl)-8-oxo-9-[(phenylmethoxy)methyl]-3,7,10,13,16-pentaazaheptadecyl]oxy]-7,12-dihydroxycholan-24-oic acid According to the procedure described in EXAMPLE 4, compound C) and (3β,5β,7α,12α)-3-[2-(amino)ethoxy]-7,12-dihydroxycholan-24-oic acid (prepared according to the procedure described in EP-A-417725), were reacted, in anhydrous MeOH and HCl, with $NaBH_3CN$, under inert atmosphere. The desired product was obtained.

The $^1$H-NMR, $^{13}$C-NMR, IR and MS spectra are consistent with the indicated structure.

E) Title compound

According to the procedure described in EXAMPLE 1, compound D) was reacted with $GdCl_3.6H_2O$ in $H_2O$, maintaining at pH 6.5 by addition of 1N meglumine. The desired product was obtained.

The IR and MS spectra are consistent with the indicated structure.

EXAMPLE 7

[[(3β,5β,7α,12α)-7,12-dihydroxy-3-[2-[[[[4-[4,12-bis(carboxy)-5,8,11-tris(carboxymethyl)-2-oxa-5,8,11-triazadodecyl]phenyl]amino]thioxomethyl]amino]ethoxy]-cholan-24-oate(6$^-$)]gadolinate(3$^-$)] hydrogen compound with 1-deoxy-1-(methylamino)-D-glucitol (1:3)

A) (3β,5β,7α,12α)-7,12-dihydroxy-3-[2-[[[[4-[4,12-bis(carboxy)-5,8,11-tris(carboxymethyl)-2-oxa-5,8,11-triazadodecyl]phenyl]amino]thioxomethyl]amino]ethoxy]-cholan-24-oic acid A solution of 4-[(1,1-dimethylethoxy)carbonyl]-5,8,11-tris[2-(1,1-dimethylethoxy)-2-oxoethyl]-1-(4-aminophenyl)-2-oxa-5,8,11-triazatridecan-13-oic acid 1,1-dimethylethyl ester (prepared according to the procedure described in EXAMPLE 1) in $CHCl_3$ was added to 1,1'-thiocarbonyl diimidazole (marketed product) and subsequently to (3β,5β,7α,12α)-3-[2-(amino)ethoxy]-7,12-dihydroxy-cholan-24-oic acid (prepared according to the procedure described in EP-A-417725). The reaction mixture was then evaporated and the residue dissolved in $CH_2Cl_2$ and hydrolysed with $CF_3COOH$ to give the desired product.

The $^1$H-NMR, $^{13}$C-NMR, IR and MS spectra are consistent with the indicated structure.

B) Title compound

According to the procedure described in EXAMPLE 1, compound A) was reacted with $GdCl_3.6H_2O$ in $H_2O$, maintaining a pH of 6.5 by addition of 1N meglumine. The desired product was obtained.

The IR and MS spectra are consistent with the indicated structure.

EXAMPLE 8

[[3,6,9-Tris(carboxymethyl)-10-[(phenylmethoxy)methyl]-11-oxo-17-[[(3α,5β,7α,12α)-3,7,12-trihydroxy-24-oxocholan-24-yl]amino]-3,6,9,12-tetraazaoctadecanedioate (5$^-$)]gadolinate(2$^-$)] dihydrogen compound with 1-deoxy-1-(methylamino)-D-glucitol (1:2)

A) $N^6$-(phenylmethoxy)carbonyl-$N^2$-[(3α,5β,7α,12α)-3,7,12-trihydroxy-24-oxocholan-24-yl]-L-lysine methyl ester A suspension of cholic acid (16.3 g; 40 mmol) and triethylamine (4.86 g; 48 mmol) in THF (350 ml), kept at 0° C. under nitrogen atmosphere, was added drop by drop with isobutyl chloroformate (6.56 g; 48 mmol) in 10 min. After 30 min a solution of $N^6$-(phenylmethoxy)carbonyl-L-lysine (marketed product) (11.2 g; 40 mmol) in 0.67N NaOH (60 ml) was dropped therein during 20 min. The reaction mixture was kept at 0° C. for one more hour and then at room temperature for 5 h. A 2N HCl aqueous solution was added to the mixture until acid pH, then the organic solvent was evaporated off under reduced pressure. The residual aqueous suspension was diluted with a NaCl saturated solution and extracted with AcOEt. The organic phases were combined, dried and evaporated to dryness, recovering a solid that was powdered and dried over $P_2O_5$ under reduced pressure. The resulting crude product was subjected to the subsequent reaction, without further purification procedures.

A solution of $N^6$-(phenylmethoxy)carbonyl-$N^2$-[(3α,5β,7α,12α)-3,7,12-trihydroxy-24-oxocholan-24-yl]-L-lysine 27.5 g) in MeOH (600 ml), kept at room temperature and under nitrogen atmosphere, was added to p-toluenesulfonic acid monohydrate (1.56 g; 8.2 mmol). After 20 h the reaction mixture was added to $Et_3N$ (0.832 g; 8.2 mmol). The mixture was evaporated under reduced pressure and the resulting crude was purified by flash chromatography to obtain the desired product (24.1 g; 35.2 mmol).

Yield: 88% m.p.: 80°–83° C.

K.F. titre: 1.37% (w/w)

HPLC titre: 99.5% (in % area)

Stationary phase: Column E. Merck Lichrosorb Select B; 5 μm; 250×4 mm

| Mobile phase: Gradient elution A = 0.01 M $KH_2PO_4$ and 0.017 M $H_3PO_4$ aqueous solution B = $CH_3CN$ | | |
|---|---|---|
| min | % A | % B |
| 0 | 95 | 5 |
| 30 | 20 | 80 |
| 45 | 20 | 80 |

Flow rate: 1 ml min$^{-1}$

Temperature: 45° C.

Detector (UV): 210 nm $[α]^{20}_D$:+16.2° (c 2.1; MeOH)

| Elemental analysis | C | H | N |
|---|---|---|---|
| % calc.: | 68.39 | 8.83 | 4.09 |
| % found: | 66.82 | 9.01 | 3.73 |

TLC: Carrier silica gel plates 60 $F_{254}$ Merck

Eluent: AcOEt: i-PrOH=9:1 (v/v)

Detector: AcOH: Conc. $H_2SO_4$: p-anisaldehyde=100:2:1 (v/v/v) $R_f$=0.22

The $^1$H-NMR, $^{13}$C-NMR, IR and MS spectra are consistent with the indicated structure.

B) $N^2$-[(3α,5β,7α,12α)-3,7,12-trihydroxy-24-oxocholan-24-yl]-L-lysine methyl ester monohydrochloride A solution of 15.0 g of compound A) (21.9 mmol) in MeOH (150 ml) was added to Pd/C (1.5 g). The mixture was hydrogenated at room temperature and pressure. The transformation was monitored by TLC and HPLC. After 1.5 h the reaction mixture was filtered through paper filter and the filtrate was cooled to 0° C. in a $H_2O$/ice bath and added to a HC solution in MeOH (20.5 ml; 23.2 mmol). The solution was evaporated under reduced pressure and the residue was powdered and dried under reduced pressure to obtain the desired product (12.4 g; 21.1 mmol).

Yield: 96% m.p.: 108°–110° C.

K.F. titre: 2.20% (w/w)

HPLC titre: 92.4% (in % area)

Stationary phase: Column E. Merck Lichrosorb Select B; 5 μm; 250×4 mm

| Mobile phase: Gradient elution A = 0.01 M $KH_2PO_4$ and 0.017 M $H_3PO_4$ aqueous solution B = $CH_3CN$ | | |
|---|---|---|
| min | % A | % B |
| 0 | 95 | 5 |
| 30 | 20 | 80 |
| 45 | 20 | 80 |

Flow rate: 1 ml min$^{-1}$

Temperature: 45° C.

Detector (UV): 210 nm $[α]^D_{20}$=+14.4° (c 2.16, MeOH)

| Elemental analysis | C | H | N | Cl |
|---|---|---|---|---|
| % calc.: | 63.40 | 9.44 | 4.77 | 6.04 |
| % found: | 62.01 | 9.89 | 4.59 | 5.93 |

TLC: Carrier: silica gel plates 60 $F_{254}$ Merck

Eluent: MeOH: $Et_3N$=95:5 (v/v)

Detector: AcOH: Conc. $H_2SO_4$: p-anisaldehyde=100:2:1 (v/v/v) $R_f$=0.33

The $^1$H-NMR, $^{13}$C-NMR, IR and MS spectra are consistent with the indicated structure.

C) 3,6,9-Tris(carboxymethyl)-10-[(phenylmethoxy)methyl]-11-oxo-17-[[(3α,5β,7α,12α)-3,7,12-trihydroxy-24-oxocholan-24-yl]amino]-3,6,9,12-tetraazoctadecanedioic acid 9.35 g of compound B) (14.3 mmol), O-phenylmethyl-N-(2-methoxy-2-oxoethyl)-N-[2-[[2-[bis(2-methoxy-2-oxoethyl)amino]ethyl](2-methoxy-2-oxoethyl)amino]ethyl]-D,L-serine (prepared as described in Example 3) (9.28 g; 14.3 mmol) and BOP-reagent (marketed product) (6.32 g; 14.3 mmol) were dissolved in DMF (140 ml) at room temperature. N,N-Diisopropylethylamine (8.51 ml; 50.1 mmol) was added to this stirred solution in 15 min. The reaction was monitored by HPLC. After 6 h the reaction mixture was evaporated under reduced pressure and the residue was dissolved in EtOAc. The solution was successively washed with saturated aqueous $NH_4Cl$, $H_2O$ up to neutral pH, dried and evaporated under reduced pressure. The solid residue was purified by flash chromatography to obtain a yellow-brown solid that was dissolved in 2:1 MeOH/$H_2O$ and 1N NaOH (1.5 ml) was added until pH 12 was reached. The reaction mixture was stirred for 21 h at room temperature maintaining a pH of 12 by addition of 1N NaOH (35.5 ml) through a pH-stat apparatus. The reaction was monitored by HPLC. The resulting solution was adjusted to pH 6.5 with 1N HCl and evaporated under reduced pressure. The residue was dissolved in 7:3 1N HCl/MeOH and the solution was loaded onto an Amberlite® XAD-16.00 resin column and eluted with a MeOH/$H_2O$ gradient. The fractions containing the ligand were concentrated to dryness under reduced pressure giving the desired product (4.51 g; 4.37 mmol).

Yield: 31% m.p.: 158°–160° C.

K.F.: 4.13% (w/w)

HPLC: 97% (area %)

Stationary phase: Column E. Merck Lichrosorb Select B; 5 μm; 250×4 mm

| Mobile phase: Gradient elution<br>A = aqueous solution 0.01 M in KH$_2$PO$_4$ and 0.017 M in H$_3$PO$_4$<br>B = CH$_3$CN | | |
|---|---|---|
| min | % A | % B |
| 0 | 95 | 5 |
| 30 | 20 | 80 |
| 45 | 20 | 80 |

Flow rate: 1 ml min$^{-1}$
Temperature: 45° C.
Detector (UV): 210 nm

| Elemental analysis | C | H | N | Cl |
|---|---|---|---|---|
| % calc.: | 60.50 | 7.91 | 6.79 | 0.00 |
| % found: | 58.13 | 8.22 | 6.33 | <0.1 |

TLC: Silica gel plates 60 F$_{254}$ (E. Merck art. 5719)
Eluent: 80:30:5:5=CHCl$_3$: MeOH: H$_2$O: Et$_3$N
Detection: AcOH: Conc. H$_2$SO$_4$: p-anisaldehyde=100:2:1 (v/v/v) R$_f$=0.25

The $^1$H-NMR, $^{13}$C-NMR, IR and MS spectra are consistent with the structure.

D) Title compound 3.52 g of compound C) (3.20 mmol) were suspended in 9:1 H$_2$O/MeOH (70 ml) at 50° C. and under nitrogen. Meglumine (1.241 g; 6.357 mmol) was added obtaining complete dissolution. Gd$_2$O$_3$ (0.581 g; 1.60 mmol) was added to the reaction mixture and the resulting suspension was stirred for 21 h at 50° C. The almost clear solution was filtered through Millipore® apparatus (HAS 0.45 µm filter) and the filtrate was adjusted to pH 7 with 1% meglumine solution (0.90 ml; 9.0 mg; 4.6 µmol). The solution was evaporated to dryness under reduced pressure to obtain a solid that was pulverized and dried under reduced pressure giving the desired product (4.90 g; 3.11 mmol).

Yield 94% m.p. 170°–175° C. (160° C., sint.)
K.F. titre: 2.15% (w/w)
HPLC titre: 97% (area %)
Stationary phase: Column E. Merck Superspher RP-18; 250×4 mm
Mobile phase: Isocratic elution: 74:26 A/B
A=0.05M aqueous solution in KH$_2$PO$_4$
B=CH$_3$CN
Flow rate: 1 ml min$^{-1}$
Temperature: 45° C.
Detector (UV): 210 nm

| Elemental analysis | C | H | N | Gd |
|---|---|---|---|---|
| % calc.: | 50.27 | 7.16 | 6.22 | 9.97 |
| % found: | 49.77 | 7.49 | 6.07 | 9.68 |

TLC: Silica gel plates 60 F$_{254}$ (E. Merck art. 5719)
Eluent: 80:30:5:5 CHCl$_3$: MeOH: H$_2$O: Et$_3$N
Detection: AcOH: Conc. H$_2$SO$_4$: p-anisaldehyde=100:2:1 (v/v/v) R$_f$=0.33

The IR and MS spectra are consistent with the structure.

EXAMPLE 9

[[(3β,5β,7α,12α)-3-[[13-carboxy-6,9,12-tris (carboxymethyl)-1,4-dioxo-3,6,9,12-tetraaazatridecyl] amino]-7,12-dihydroxy-cholan-24-oate(5$^-$)]gadolinate (1$^{-1}$)] hydrogen compound with 1-deoxy-1-(methylamino)-D-glucitol (1:2)

A) (3β,5β,7α,12α)-3-[[13-Carboxy-6,9,12-tris (carboxymethyl)-1,4-dioxo-3,6,9,12-tetraaazatridecyl] amino]-7,12-dihydroxy-cholan-24-oic acid A suspension of diethyleneetriaminepentaacetic dianhydride (marketed product) (0.142 mol) in DMF (850 ml) at 80° C., was added drop by drop to a solution of H$_2$O (0.211 mol) and DMF (50 ml). After 1.5 h. a solution of (3β,5β, 7α,12α)-3-(aminoacetyl)amino-7,12-dihydroxy-cholan-24-oic acid methyl ester (prepared according to the procedure of EXAMPLE 5) (0.0356 mol) in DMF (100 ml) was dropped therein. When the addition was over, the mixture was cooled to 20° C. and 2N NaOH (360 ml) was dropped therein. After 24 h the mixture was adjusted to pH 7 with 37% HCl and the solution was evaporated under vacuum. The residue was dissolved with MeOH/H$_2$O=3/7 (500 ml) and with 37% HCl (7 ml). The resulting solution was loaded on an Amberlite® XAD-16 resin and eluted with a MeOH/H$_2$O gradient to obtain the desired product.

The $^1$H-NMR, $^{13}$C-NMR, IR and MS spectra are consistent with the indicated structure.

B) Title compound

According to the procedure described in EXAMPLE 1, compound A) was reacted with GdCl$_3$.6H$_2$O in H$_2$O, maintaining at pH 6.5 by addition of 1N meglumine. The desired product was obtained.

The IR and MS spectra are consistent with the indicated structure.

In the same way, the gadolinium complexes of the following ligands were prepared: p1 3,6,9-Tris(carboxymethyl) -14-[[(3β,5β,7α,12α)-7,12-dihydroxy-24-oxo-24-[(2-sulfoethyl)amino]-cholan-3-yl]amino]-11,14-dioxo-3,6,9, 12-tetraazatetradecanoic acid (COMPOUND 22);

[(3β,5β,7α,12α)-3-[[17-carboxy-10,13,16-tris (carboxymethyl)- 1,8-dioxo-7,10,13,16-tetraazaheptadecyl]amino]-7,12-dihydroxy-cholan-24-oic acid (COMPOUND 23);

(17S)-3,6,9-Tris(carboxymethyl)-11-oxo-17-[[(3β,5β,7α, 12α)-3,7,12-trihydroxy-24-oxocholan-24-yl]amino]-3, 6,9,12-tetraazaoctadecanedioic acid (COMPOUND 24).

EXAMPLE 10

[(3β,5β,7α,12α)-(3'β,5'β,7'α,12'α)-3,3'-[[6,9,12-tris (carboxymethyl)-1,4,14,17-tetraoxo-3,6,9,12,15-pentaazaheptadecan-1,17-diyl]bisimino]bis[7,12-dihydroxycholan-24-oate(5$^-$)]gadolinate(2$^-$)] hydrogen compound with 1-deoxy-1-(methylamino)-D-glucitol (1:2)

A) (3β,5β,7α,12α)-(3'β,5'β,7'α,12'α)-3,3'-[[6,9,12-tris (carboxymethyl)-1,4,14,17-tetraoxo-3,6,9,12,15-pentaazaheptadecan-1,17-diyl]bisimino]bis[7,12-dihydroxy-cholan-24-oic] acid Diethylenetriamino pentaacetic acid dianhydride (marketed product) was reacted in DMF with two equivalents of (3β,5β,7α,12α)-3-(aminoacetyl)amino-7,12-dihydroxycholan-24-oic acid methyl ester (prepared according to the procedure described in Example 5). The reaction mixture was subsequently treated with a LiOH monohydrate aqueous solution, evaporated and the residue was dissolved in 1N HCl and eluted through an Amberlite® XAD-16 polystyrene resin, to obtain the desired product.

The $^1$H-NMR, $^{13}$C-NMR, IR and MS spectra are consistent with the indicated structure.

B) Title compound

According to the procedure described in EXAMPLE 1, compound A) was reacted with $GdCl_3.6H_2O$ in $H_2O$, maintaining a pH of 6.5 by addition of 1N meglumine. The desired product was obtained. The IR and MS spectra are consistent with the indicated structure.

EXAMPLE 11

[[[3β(S),5β,7α,12α]-7,12-dihydroxy-3-[[4-[[[[5-[bis[2-[bis(carboxymethyl)amino]ethyl]amino]-5-carboxypentyl]amino]thioxomethyl]amino]benzoyl]amino]-cholan-24-oate(6⁻)]gadolinate(3⁻)] hydrogen compound with 1-deoxy-1-(methylamino)-D-glucitol (1:3)

A) $N^2$-Bis[2-[bis(carboxymethyl)amino]ethyl]-L-lysine

This product was synthesized starting from $N^6$-(phenylmethoxy)carbonyl-L-lysine (marketed product) analogously to what described by M. A. Williams and H. Rapoport, J. Org. Chem. 1993, 58, 1151–1158 for the 4-nitro-L-phenylalanine.

The $^1$H-NMR, $^{13}$C-NMR, IR and MS spectra are consistent with the indicated structure.

B) [3β(S),5β,7α,12α]-7,12-dihydroxy-3-[[4-[[[[5-[bis-[2-[bis(carboxymethyl)amino]ethyl]amino]-5-carboxypentyl]amino]thioxomethyl]amino]benzoyl]amino]-cholan-24-oic acid A solution of (3β,5β,7α,12α)-3-amino-7,12-dihydroxycholan-24-oic acid (prepared according to the procedure described in EP-A-417725) in DMF and triethylamine was added with an equimolecular amount of 4-isothiocyanatobenzoyl chloride (prepared according to the procedure described by N. Viswanathan and R. C. Desai, Indian J. Chem., 1981, 20B, 308–310). After (3β,5β,7α,12α)-3-amino-7,12-dihydroxycholan-24-oic acid had been completely converted, compound A) was added to the reaction mixture. When the reaction was over, the solvent was evaporated off and the residue was dissolved in 1N HCl and eluted through an Amberlite® XAD-16 polystyrene resin, to obtain the desired product.

The $^1$H-NMR, $^{13}$C-NMR, IR and MS spectra are consistent with the indicated structure.

C) Title compound

According to the procedure described in EXAMPLE 1, compound B) was reacted with $GdCl_3.6H_2O$ in $H_2O$, maintaining at pH 6.5 by addition of 1N meglumine. The desired product was obtained. The IR and MS spectra are consistent with the indicated structure.

EXAMPLE 12

[[[3β(S),5β,7α,12α]-7,12-dihydroxy-3-[[4-[[5-[bis[2-[bis(carboxymethyl)amino]ethyl]amino]-5-carboxypentyl]amino]-1,4-dioxobutyl]amino]-cholan-24-oate(6⁻)]gadolinate(3⁻)] hydrogen compound with 1-deoxy-1-(methylamino)-D-glucitol (1:3)

A) (3β,5β,7α,1α2)-3-[(3-carboxy-1-oxopropyl)amino]-7,12-dihydroxycholan-24-oic acid methyl ester A solution of 6.15 g of (3β,5β,7α,12α)-3-amino-7,12-dihydroxycholan-24-oic acid methyl ester (prepared according to the procedure described in EXAMPLE 5) (15 mmol) in 85 ml of THF and 17 ml of triethylamine was added to 1.5 g of succinic anhydride (15 mmol). After 4 h at room temperature the reaction mixture was poured into 200 ml of 1N HCl and extracted with AcOEt. The organic phase was washed with $H_2O$, dried and evaporated under reduced pressure. The residue was purified by flash chromatography, to obtain 4.5 g of the desired product (8.6 mmol).

Yield: 57% m.p.: 92°–94° C.

| Elemental analysis | C | H | N | |
|---|---|---|---|---|
| % calc.: | 66.76 | 9.08 | 2.68 | |
| % found: | 65.45 | 9.40 | 2.50 | 0.56 $H_2O$ |

TLC: Carrier: silica gel plates 60 $F_{254}$ Merck

Eluent: AcOEt: AcOH=4:1

Detector: AcOH: Conc. $H_2SO_4$: p-anisaldehyde $R_f$=0.47

The $^1$H-NMR, $^{13}$C-NMR, IR and MS spectra are consistent with the indicated structure.

B) (3β,5β,7α,12α)-3-[[4-[(2,5-dioxo-1-pyrrolidinyl)oxy]-1,4-dioxobutyl]amino]-7,12-dihydroxy-cholan-24-oic acid methyl ester A solution of compound A) in anhydrous THF and anhydrous acetonitrile was added to N-hydroxysuccinimide and subsequently to dicyclohexylIcarbodiimide: dicyclohexylurea precipitated and was filtered off. The solution was evaporated under reduced pressure to obtain the desired product.

The $^1$H-NMR, $^{13}$C-NMR, IR and MS spectra are consistent with the indicated structure.

C) [3β(S),5β,7α,12α]-7,12-dihydroxy-3-[[4-[[5-[bis[2-[bis(carboxymethyl)amino]ethyl]amino]-5-carboxypentyl]amino]-1,4-dioxobutyl]amino]-cholan-24-oic acid A solution of compound B) in DMF was added to a solution of $N^2$-bis[2-[bis(carboxymethyl)amino]ethyl]-L-lysine (prepared according to the procedure described in Example 11) in DMF and triethylamine. After 24 h, the reaction mixture was added to a LiOH monohydrate aqueous solution, then the solvent was evaporated and the residue was dissolved in 1N HCl and eluted through an Amberlite® XAD-16 polystyrene resin, to obtain the desired product.

The $^1$H-NMR, $^{13}$C-NMR, IR and MS spectra are consistent with the indicated structure.

D) Title compound

According to the procedure described in EXAMPLE 1, compound C) was reacted with $GdCl_3.6H_2O$ in $H_2O$, maintaining a pH of 6.5 by addition of 1N meglumine. The desired product was obtained.

The $^1$H-NMR, $^{13}$C-NMR, IR and MS spectra are consistent with the indicated structure.

EXAMPLE 13

[[(3β,5β,7α,12α)-7,12-dihydroxy-3-[[4-[[2-[[4-[4,12-bis(carboxy)-5,8,11-tris(carboxymethyl)-2-oxa-5,8,11-triazadodecyl]phenyl]amino]-2-oxoethyl]amino]-1,4-dioxobutyl]amino]-cholan-24-oate(6⁻)]gadolinate(3⁻)] hydrogen compound with 1-deoxy-1-(methylamino)-D-glucitol (1:3)

A) (3β,5β,7α,12α)-7,12-dihydroxy-3-[[4-[[2-[[4-[4,12-bis(carboxy)-5,8,11-tris(carboxymethyl)-2-oxa-5,8,11-triazadodecyl]phenyl]amino]-2-oxoethyl]amino]-1,4-dioxobutyl]amino]-cholan-24-oic acid A solution of 4-[(1,1-dimethylethoxy)carbonyl]-5,8,11-tris[2-(1,1-dimethylethoxy)-2-oxoethyl]-1-[4-[[[[(1,1-dimethylethoxy)carbonyl]amino]acetyl]amino]phenyl]-2-oxa-5,8,11-triazatridecan-13-oic acid 1,1-dimethylethyl ester (prepared according to the procedure described in EXAMPLE 1) in anisole and $CH_2Cl_2$ was treated with trifluoroacetic acid. After 3 days the reaction mixture was evaporated under reduced pressure, the residue was taken up into $CH_2Cl_2$ and evaporated again, repeating said procedure 2 more times. The residue was then suspended in $H_2O$, neutralized at 0° C. with 25% $NH_4OH$ (w/w) and extracted with ethyl ether. The aqueous phase was evaporated under reduced pressure to obtain a residue that was purified by flash chromatography. The resulting solid was dissolved in DMF and triethylamine and said solution was added to the succinimido derivative of (3β,5β,7α,12α)-3-[[4-[(2,5-dioxo-1-pyrrolidinyl)oxy]-1,4-dioxobutyl]amino]-7,12-dihydroxy-cholan-24-oic acid methyl ester (prepared according to the procedure described in Example 12). After 24h the reaction mixture was added to a LiOH monohydrate aqueous solution, then the solvent was evaporated and the residue was dissolved in 1N HCl and eluted through an Amberlite® XAD-16 polystyrene resin, to obtain the desired product.

The $^1$H-NMR, $^{13}$C-NMR, IR and MS spectra are consistent with the indicated structure.

B) Title compound

According to the procedure described in EXAMPLE 1, compound A) was reacted with $GdCl_3.6H_2O$ in $H_2O$, maintaining a pH of 6.5 by addition of 1N meglumine. The desired product was obtained.

The IR and MS spectra are consistent with the indicated structure.

EXAMPLE 14

[[(3β,5β,7α,12α)-3-[[6-[[[bis[2-[bis(carboxymethyl)amino]ethyl]amino]acetyl]amino]-1-oxohexyl]amino]-7,12-dihydroxy-cholan-24-oate(5$^-$)]gadolinate(2$^-$)] hydrogen compound with 1-deoxy-1-(methylamino)-D-glucitol (1:2)

A) N-[bis[2-[bis[[2-(1,1-dimethylethoxy)-2-oxoethyl]amino]ethyl]glycine 1 g of glycine (marketed product) (0.0133 mol) was dissolved in 100 ml of $H_2O$/EtOH (25/75) and a solution of NaOH 1N (8.8 mL, 8.8 mmol) was added until pH=10 was reached. Then a solution of 10 g of N-(2-bromoethyl)-N-[2-(1,1-dimethylethoxy)-2-oxoethyl]glycine 1,1 dimethylethyl ester (prepared according to Williams, M. A., et al., J. Org. Chem., 1993, 58, 1151) (0.0284 mmol) in t0 ml of 95% EtOH was added. After keeping the reaction at room temperature for 18 h., the mixture was evaporated to dryness. The residue was purified by flash chromatography obtaining 6 g of the desired product (0.010 mol).

Yield 73%

TLC: Silica gel plates 60 $F_{254}$ (E. Merck art. 5719)

Eluent: 1:9=MeOH: AcOH

Detection: 0.5% $KMnO_4$ in 0.1N NaOH $R_f$=0.20

The $^1$H-NMR, $^{13}$C-NMR, IR and MS spectra are consistent with the structure.

B) (3β,5β,7α,12α)-3-[[[6-[(phenylmethoxy)carbonyl]amino]1-oxohexyl]amino]-7,12-dihydroxy-cholan-24-oic acid methyl ester A solution of 3.46 g of N-Cbz-6-aminohexanoic acid (commercially available from Lancaster) (0.0130 mol) in 70 ml of THF and 1.8 ml of TEA (1.31 g, 0.0130 mol) was added, very quickly, to 1.77 g of isobutyl chloroformate (marketed product) (1.7 mL, 0.0130 mol) keeping the temperature at 0°–3° C. After 15 min. 5 g of (3β,5β,7α,12α)-3-amino-7,12-dihydroxy-cholan-24-oic acid methyl ester (prepared according to Example 5) (0.119 mol) in 30 ml of THF were added. After 30 min. from the end of dropping the temperature was kept at room temperature and the reaction mixture was filtered through a sintered glass filter and evaporated under reduced pressure. The solid was dissolved in $CH_2Cl_2$ and washed with $H_2O$ and brine. The phases were separated and the organic one was evaporated. The residue was dissolved in $CH_2Cl_2$ and washed with a saturated solution $NaHCO_3$ and $H_2O$. The organic layers were combined, dried and evaporated under reduced pressure to give a solid, that was crystallized by AcOEt, obtaining the desired product (4.7 g, 0.0070 mol).

Yield: 60%

HPLC: 98.5 % (area %)

Stationary phase: Column E. Merck Lichrosorb Select B; 5 μm; 250×4 mm

| Mobile phase: Gradient elution A = 0.01 M aqueous solution in $KH_2PO_4$ and 0.017 M in $H_3PO_4$ B = $CH_3CN$ | | |
|---|---|---|
| min | % A | % B |
| 0 | 95 | 5 |
| 30 | 20 | 80 |
| 45 | 20 | 80 |

Flow rate: 1 ml min$^{-1}$

Temperature: 45° C.

Detector (UV): 210 nm

| Elemental analysis | C | H | N | |
|---|---|---|---|---|
| % calc.: | 70.03 | 9.04 | 4.19 | |
| % found: | 69.82 | 9.08 | 4.18 | $H_2O$ 0.24 |

TLC: Silica gel plates 60 $F_{254}$ (E. Merck art. 5719)

Eluent: AcOEt: i-PrOH=95:5 (v/v)

Detection: AcOH: Conc. $H_2SO_4$: p-anisaldehyde=100:2:1 (v/v/v) $R_f$=0.41

The $^1$H-NMR, $^{13}$C-NMR, IR and MS spectra are consistent with the structure.

C) (3β,5β,7α,12α)-3-[(6-amino-1-oxohexyl)amino]-7,12-dihydroxy-cholan-24-oic acid methyl ester 4 g of compound B) (0.00598 mol) were dissolved in 50 ml of EtOH abs. and 800 mg of Pd/C were added. The hydrogenation was performed at room temperature and atmospheric pressure. When the reaction had terminated, the mixture was filtered and evaporated to dryness. The residue was purified by flash chromatography obtaining the desired product (2.7 g, 0.005 mol).

Yield: 84.4%

HPLC: 95% (area %)

Stationary phase: Column E. Merck Lichrosorb Select B; 5 μm; 250×4 mm

| Mobile phase: Gradient elution A = aqueous solution 0.01 M in $KH_2PO_4$ and 0.017 M in $H_3PO_4$ B = $CH_3CN$ | | |
|---|---|---|
| min | % A | % B |
| 0 | 95 | 5 |
| 30 | 20 | 80 |
| 45 | 20 | 80 |

Flow rate: 1 ml min$^{-1}$

Temperature: 45° C.
Detector (UV): 210 nm
TLC: Silica gel plates 60 $F_{254}$ (E. Merck art. 5719)
Eluent: MeOH: TEA=95:5 (v/v)
Detection: AcOH: Conc. $H_2SO_4$: p-anisaldehyde=100:2:1 (v/v/v) $R_f$=0.33

The $^1$H-NMR, $^{13}$C-NMR, IR and MS spectra are consistent with the structure.

D) (3β,5β,7α,12α)-3-[[6-[[[Bis[2-[bis(carboxymethyl)amino]ethyl]amino]acetyl]amino]-1-oxohexyl]amino]-7,12-dihydroxy-cholan-24-oic acid Equimolecular amounts of compound A) and of compound C) were reacted at room temperature with benzotriazol-1-yloxy-tris(dimethylamino)phosphonium hexafluorophosphate (BOP, marketed product) in DMF and in the presence of a N,N-diisopropylethylamine excess. When the reaction was over, the reaction mixture was evaporated under vacuum and the residue taken up into EtOAc. The solution was washed with a $NH_4Cl$ saturated solution and with $H_2O$ to neutral pH, then evaporated. The residue was hydrolysed first with 1M NaOH in MeOH/$H_2O$ then with $CF_3COOH$ in $CH_2Cl_2$, to give the desired product that was purified and salted off by elution on an Amberlite® XAD-16 resin using a MeOH/$H_2O$ gradient.

The $^1$H-NMR, $^{13}$C-NMR, IR and MS spectra are consistent with the indicated structure.

E) Title compound

According to the procedure described in EXAMPLE 1, compound A) was reacted with $GdCl_3.6H_2O$ in $H_2O$, maintaining a pH of 6.5 by addition of 1N meglumine. The desired product was obtained, that was salted off by elution with a MeOH/$H_2O$ gradient on an Amberlyte XAD-16 resin.

The IR and MS spectra are consistent with the indicated structure.

In the same way the gadolinium complexes of the following ligands were prepared:
(3β,5β,7α,12α)-3-[[[[[bis[2-[bis(carboxymethyl)amino]ethyl]amino]acetyl]amino]acetyl]amino]-7,12-dihydroxycholan-24-oic acid (COMPOUND 26);
$N^6$-[[bis[2-[bis(carboxymethyl)amino]ethyl]amino]acetyl]-$N^2$-[(3α,5β,7α,12α)-3,7,12-trihydroxy-24-oxocholan-24-yl]-L-lysine (COMPOUND 27);

EXAMPLE 15

[[$N^6$-[(4S)[4-[Bis[2-[bis(carboxymethyl)amino]ethyl]amino]-4-carboxy]-1-oxobutyl]-$N^2$-[(3α,5β,7α,12α)-3,7,12-trihydroxy-24-oxocholan-24-yl]-L-lysinate($6^-$)]gadolinate($3^-$)] hydrogen compound with 1-deoxy-1-(methylamino)-D-glucitol (1:3)

A) N,N-Bis[2-[bis[2-(1,1-dimethylethoxy)-2-oxoethyl]amino]ethyl]-L-glutamic 1-(1,1-dimethylethyl) ester 5-(phenylmethyl)ester 132.01 g of 1-(1,1-dimethylethyl) ester 5-(phenylmethyl) ester L-glutamic acid (prepared according to Helv. Chim. Acta, 199, 1864, 1958) (0.45 mol) were dissolved in 200 ml of $H_2O$ and 1 L of EtOH and added to 320.2 g of N-(2-bromoethyl)-N-[2-(1,1-dimethylethoxy)-2-oxoethyl]glycine 1,1 dimethylethyl ester (prepared according to Williams, M., A. et al., J. Org. Chem., 58, 1151. 1993) (0.909 mol) maintaining a pH of 8 by addition of 10N NaOH. After 50h at 5° C., temperature was brought to 20° C. for a further 80h and to 50° C. for 5 h. The mixture was adjusted to pH 7 with conc. HCl, evaporated and extracted with hexane; the organic phase was concentrated and the residue was purified by flash chromatography to obtain the desired product (75.2 g, 0.09 mol).

Yield: 20%
TLC: Silica gel plates 60 $F_{254}$ (E. Merck art. 5719)
Eluent: hexane: AcOEt=2:1 (v/v)
Detection: 0.5% $KMnO_4$ in 0.1N NaOH $R_f$=0.76

The $^1$H-NMR, $^{13}$C-NMR, IR and MS spectra are consistent with the structure.

B) N,N-Bis[2-[bis[2-(1,1-dimethylethoxy)-2-oxoethyl]amino]ethyl]-L-glutamic acid 1-(1,1-dimethylethyl) ester 15.05 g of compound A) (18 mmol) dissolved in 100 ml of EtOH were added to 4 g of 5% wet Pd/C and the mixture was hydrogenated under a $H_2$ pressure of 111.36 kPa. When the reaction was over, the mixture was filtered, concentrated to a residue and purified by flash chromatography obtaining the desired product (11.01 g, 14.76 mmol).

Yield: 82%
TLC: Silica gel plates 60 $F_{254}$ (E. Merck art. 5719)
Eluent: AcOEt
Detection: 0.5% $KMnO_4$ in 0.1N NaOH $R_f$=0.85

The $^1$H-NMR, $^{13}$C-NMR, IR and MS spectra are consistent with the structure.

C) $N^6$-[(4S)[4-[Bis[2-[bis(carboxymethyl)amino]ethyl]amino]-4-carboxy]-1-oxobutyl]-$N^2$-[(3α,5β,7α,12α)-3,7,12-trihydroxy-24-oxocholan-24-yl]-L-lysine Equimolecular amounts of compound B) and $N^2$-[(3α,5β,7α,12α)-3,7,12-trihydroxy-24-oxocholan-24-yl]-L-lysine methyl ester monohydrochloride (prepared as described in EXAMPLE 8) were reacted at room temperature with BOP in DMF and in the presence of a N,N-diisopropylethylamine excess. When the reaction was over, the reaction mixture was evaporated under vacuum and the residue taken up with EtOAc. The solution was washed with a $NH_4Cl$ saturated solution and with $H_2O$ to a neutral pH, then evaporated. The residue was hydrolysed first with 1M NaOH in MeOH/$H_2O$, then with $CF_3COOH$ in $CH_2Cl_2$ to give the desired product that was purified and salted off by elution on an Amberlite® XAD-16 resin using a MeOH/$H_2O$ gradient.

The $^1$H-NMR, $^{13}$C-NMR, IR and MS were consistent with the structure.

D) Title compound

According to the procedure described in EXAMPLE 1, compound B) was reacted with $GdCl_3.6H_2O$ in $H_2O$, maintaining at pH 6.5 by addition of 1N meglumine. The resulting product was salted off by elution with a MeOH/$H_2O$ gradient on an Amberlite® XAD-16 resin.

The IR and MS spectra are consistent with the structure.

In the same way the gadolinium complex of the following ligand was prepared:
[3β(S),5β,7α,12α]-3-[4-carboxy-4-[bis[2-[bis(carboxymethyl)amino]ethyl]amino]-1-oxobutyl]amino]-7,12-dihydroxy-cholan-24-oic acid (COMPOUND 29);

EXAMPLE 16

[[10-[2-[[2-[[(3β,5β,7α,12α)-7,12-dihydroxy-24-oxo-24-[(2-sulfoethyl)amino]cholan-3-yl]amino]-2-oxoethyl]amino]-2-oxoethyl]-1,4,7,10-tetraazacyclododecane-1,4,7-triacetoate($4^-$)]gadolinate($1^-$)] hydrogen compound with 1-deoxy-1-(methylamino)-D-glucitol (1:1)

A) 1,4,7,10-Tetraazacyclododecane-1,4,7-triacetic acid tris(1,1-dimethylethyl)ester monohydrochloride A stirred solution of 90 g of 10-formyl-1,4,7,10-tetraazacyclododecane-triacetic acid tris(1,1-dimethylethyl) ester (prepared according to EP-A-292689) (0.166 mol) in 1

L of anhydrous EtOH was added to 12.24 g of hydroxylamine hydrochloride (0.1826 mol) and refluxed under argon atmosphere for 18 hours. At the end of this period, the reaction mixture was cooled and ethanol was removed under reduced pressure. To the resulting solid, $CH_2Cl_2$ was added and the suspension was transferred to a separatory funnel. After washing with water and brine, the organic phase was separated, dried and concentrated under reduced pressure to obtain a residue. The solid was recrystallized twice from a $CH_2Cl_2$/hexane mixture and dried under in a vacuum oven at 35° C. for 18 hours to obtain 57 g of the desired product (0.103 mol).

Yield 62.3%

| Elemental analysis | C | H | N | Cl | |
|---|---|---|---|---|---|
| % calc.: | 55.21 | 9.25 | 9.84 | 7.49 | |
| % found: | 55.40 | 9.43 | 9.84 | 7.48 | $H_2O$ 1.41 |

TLC: Silica gel plates 60 $F_{254}$ (E. Merck art. 5719)

Eluent: 95:5=MeOH: AcOH

Detection: 0.5% $KMnO_4$ in 0.1N NaOH $R_f$=0.67

The $^1$H-NMR, $^{13}$C-NMR, IR and MS spectra are consistent with the structure.

B) (3β,5β,7α,12α)-3-[[[[(1,1-dimethylethoxy)carbonyl]amino]acetyl]amino]-7,12-dihydroxy-cholan-24-oic acid methyl ester To a solution of N-(t-butoxycarbonyl)glycine (marketed product) (14.7 g; 84.0 mmol) and $Et_3N$ (8.50 g; 11.6 ml; 84.0 mmol) in THF (400 ml), at 0° C. and under nitrogen, was added dropwise isobutyl chloroformate (11.5 g; 10.9 ml; 84.0 mmol). After 15 min a solution of (3β,5β,7α,12α)-3-amino-7,12-dihydroxy-cholan-24-oic acid methyl ester (prepared according to Example 5) (29.5 g; 70.0 mmol) in THF (100 ml) was added dropwise to the reaction mixture at 0° C. After 20 min the reaction mixture was allowed to rise to room temperature and stirred overnight. The suspension was filtered through a sintered funnel and the filtrate was evaporated under reduced pressure to give a residue that was dissolved in $Et_2O$ and washed with a saturated aqueous solution of $NaHCO_3$ and $H_2O$. The organic phase was separated, dried and then evaporated under reduced pressure. The solid residue was purified by flash chromatography to give the desired product as a white solid (25.3 g; 43.7 mmol).

Yield: 62% m.p.: 110°–114° C.

K.F.: 0.75%

HPLC: 97 % (area %)

Stationary phase: Column E. Merck Lichrosorb Select B; 5 μm; 250×4 mm

| Mobile phase: Gradient elution A = aqueous solution 0.01 M in $KH_2PO_4$ and 0.017 M in $H_3PO_4$ B = $CH_3CN$ | | |
|---|---|---|
| min | % A | % B |
| 0 | 95 | 5 |
| 30 | 20 | 80 |
| 45 | 20 | 80 |

Flow rate: 1 ml $min^{-1}$

Temperature: 45° C.

Detector (UV): 210 nm

| Elemental analysis | C | H | N |
|---|---|---|---|
| % calc.: | 66.40 | 9.40 | 4.84 |
| % found: | 64.97 | 9.07 | 4.60 |

TLC: Silica gel plates 60 $F_{254}$ (E. Merck art. 5719)

Eluent: EtOAc: i-PrOH=9:1 (v/v)

Detection: AcOH: Conc. $H_2SO_4$: p-anisaldehyde=100:2:1 (v/v/v) $R_f$=0.43

The $^1$H-NMR, $^{13}$C-NMR, IR and MS spectra are consistent with the structure.

C) (3β,5β,7α,12α)-3-[[[[(1,1-dimethylethoxy)carbonyl]amino]acetyl]amino]-7,12-dihydroxy-cholan-24-oic acid To a solution of compound B) (24.5 g; 41.1 mmol) in MeOH/$H_2O$ (2:1, v/v; 160 ml) at room temperature, was added dropwise 1N NaOH (49.7 ml; 49.7 mmol) in 2 hours. After 48 h the reaction mixture was filtered through a sintered glass filter and evaporated under reduced pressure. The residue was treated with 0.5N HCl/EtOAc (1:2, 240 ml) and pH of the resulting mixture was adjusted to 2 with 2N HCl (10 ml) under vigorous stirring. After separation the aqueous phase was saturated with NaCl and extracted with EtOAc. The organic layers were combined, dried and evaporated under reduced pressure obtaining the desired product (22.2 g, 39.3 mmol).

Yield: 96% m.p.: 150°–155° C.

K.F.: 0.75%

Acidic titre (0.1N NaOH): 95%

HPLC: 96 % (area %)

Stationary phase: Column E. Merck Lichrosorb Select B; 5 μm; 250×4 mm

| Mobile phase: Gradient elution A = aqueous solution 0.01 M in $KH_2PO_4$ and 0.017 M in $H_3PO_4$ B = $CH_3CN$ | | |
|---|---|---|
| min | % A | % B |
| 0 | 95 | 5 |
| 30 | 20 | 80 |
| 45 | 20 | 80 |

Flow rate: 1 ml $min^{-1}$

Temperature: 45° C.

Detector (UV): 210 nm

| Elemental analysis | C | H | N |
|---|---|---|---|
| % calc.: | 65.92 | 9.28 | 4.96 |
| % found: | 65.41 | 9.98 | 4.60 |

TLC: Silica gel plates 60 $F_{254}$ (E. Merck art. 5719)

Eluent: EtOAc: i-PrOH: AcOH=90:15:1 (v/v)

Detection: AcOH: Conc. $H_2SO_4$: p-anisaldehyde=100:2:1 (v/v/v) $R_f$=0.47

The $^1$H-NMR, $^{13}$C-NMR, IR and MS spectra are consistent with the structure.

D) 2-[[(3β,5β,7α,12α)-3-[[[[(1,1-dimethylethoxy)carbonyl]amino]acetyl]amino]-7,12-dihydroxy-24-oxocholan-24-yl]amino]ethanesulfonic acid Taurine (2-aminoethanesulfonic acid) (marketed product) (5.40 g; 43.1 mmol) and Et$_3$N (5.16 g; 7.07 ml; 51.0 mmol) were added to a solution of compound C) (22.1 g; 39.1 mmol) and (2-ethoxy-1-ethoxycarbonyl-1,2-dihydroquinoline, EEDQ) (marketed product) (12.6 g; 51.0 mmol) in DMF (100 ml) under nitrogen. The resulting suspension was heated at 90° C. for 70 min. obtaining a clear solution which was then cooled to 25° C. After 30 min the reaction mixture was poured slowly into cold Et$_2$O (0° C., 900 ml): a resinous product was formed. The suspension was kept at 4° C. overnight. The mixture was decanted and the resinous substance was washed with Et$_2$O, treated with CH$_2$Cl$_2$ and filtered to remove unreacted taurine. The filtrate was poured into cold Et$_2$O (0° C.) the precipitate was filtered through a sintered glass filter and immediately dissolved in 0.4N NaOH in MeOH (100 ml). After diluting the solution with Et$_2$O, the suspension was kept at 4° C. for several hours and then filtered through a sintered glass filter. The solid was washed thoroughly with Et$_2$O and dried under reduced pressure to give the desired product (24.7 g; 35.6 mmol).

Yield: 91% m.p.: 150°–155° C.

TLC: Silica gel plates 60 F$_{254}$ (E. Merck art. 5719)

Eluent: CHCl$_3$: MeOH: AcOH=90:30:4 (v/v/v)

Detection: AcOH: Conc. H$_2$SO$_4$: p-anisaldehyde=100: 2:1 (v/v/v) R$_f$=0.16

The $^1$H-NMR, $^{13}$C-NMR, IR and MS spectra are consistent with the structure.

E) 2-[[(3β,5β,7α,12α)-3-[(aminoacetyl)amino]-7,12-dihydroxy-24-oxocholan-24-yl]amino] ethanesulfonic acid sodium salt 22.4 g of compound D) (32.3 mmol) were suspended in 1M methanolic HCl (160 mmol, 160 ml) at room temperature. During the reaction time, the suspension became thicker and after 1 day the reaction mixture was filtered through a sintered glass filter. The collected solid was washed thoroughly with Et$_2$O/MeOH (1:1 v/v) and dried under reduced pressure obtaining the desired product (13.0 g; 20.6 mmol).

Yield: 64% m.p.: 200° C.

HPLC: 94% (area %)

Stationary phase: Column E. Merck Lichrosorb Select B; 5 μm; 250×4 mm

| Mobile phase: Gradient elution A = aqueous solution 0.01 M in KH$_2$PO$_4$ and 0.017 M in H$_3$PO$_4$ B = CH$_3$CN | | |
|---|---|---|
| min | % A | % B |
| 0 | 95 | 5 |
| 30 | 20 | 80 |
| 45 | 20 | 80 |

Flow rate: 1 ml min$^{-1}$

Temperature: 45° C.

Detector (UV): 210 nm

TLC: Silica gel plates 60 F$_{254}$ (E. Merck art. 5719)

Eluent: MeOH: AcOH=95:5 (v/v)

Detection: AcOH: Conc. H$_2$SO$_4$: p-anisaldehyde=100: 2:1 (v/v/v) R$_f$=0.67

The $^1$H-NMR, $^{13}$C-NMR, IR and MS spectra are consistent with the structure.

F) 10-[2-[[2-[[(3β,5β,7α,12α)-7,12-dihydroxy-24-oxo-24-[(2-sulfoethyl)amino]cholan-3-yl]amino]-2-oxoethyl] amino]-2-oxoethyl]-1,4,7,10-tetraazacyclododecane-1,4,7-triacetic acid A solution of compound A) and triethylamine in DMF at 5° C. was added drop by drop to isobutyl chloroformate and subsequently to a solution of compound E) in DMF. When the reaction was over solvent was evaporated under vacuum, the residue was dissolved with CH$_2$Cl$_2$ and trifluoroacetic acid was dropped therein at 0° C. When the addition was completed the mixture was left to react at room temperature. When the reaction was over the reaction mixture was evaporated under reduced pressure. The residue was taken up with CH$_2$Cl$_2$ and evaporated again repeating such a procedure 2 more times. The residue was purified and salted off by elution on an Amberlite® XAD-16 resin using a MeOH/H$_2$O gradient to obtain the desired product.

The $^1$H-NMR, $^{13}$C-NMR, IR and MS spectra are consistent with the structure.

G) Title compound

According to the procedure described in EXAMPLE 1, compound F) was reacted with GdCl$_3$.6H$_2$O in H$_2$O, maintaining a pH of 6.5 by addition of 1N meglumine. The desired product was obtained that was salted off by elution with a MeOH/H$_2$O gradient on an Amberlyte XAD-16 resin.

The IR and MS spectra are consistent with the structure.

In the same way, the gadolinium complexes of the following ligands were prepared:

(3β,5β,7α,12α)-3-[[[[[4,7,10-tris(Carboxymethyl)-1,4,7,10-tetraazacyclododecyl]acetyl]amino]acetyl]amino]-7,12-dihydroxy-cholan-24-oic acid (COMPOUND 31);

N$^2$-[(3α,5β,7α,12α)-3,7,12-trihydroxy-24-oxocholan-24-yl]-N$^6$-[[4,7,10-tris(carboxymethyl)-1,4,7,10-tetraazacyclododecyl]acetyl]-L-lysine (COMPOUND 32);

(3β,5β,7α,12α)-3-[[6-[[[4,7,10-tris(carboxymethyl)-1,4,7,10-tetraazacyclododecyl]acetyl]amino]-1-oxohexyl] amino]-7,12-dihydroxy-cholan-24-oic acid (COMPOUND 33).

EXAMPLE 17

[[(3α,5β,7α,12α)-3-[[3-[4,7,10-tris(carboxymethyl)-1,4,7,10-tetraazacyclododecyl]-2-hydroxypropyl]oxy]-7,12-dihydroxy-cholane-24-oate(4$^-$)]gadolinate(1$^-$)] hydrogen compound with 1-deoxy-1-(methylamino)-D-glucitol (1:1)

A) (3α,5β,7α,12α)-3-(2,3-epoxypropyl)oxy-7,12-dihydroxy-cholan-24-oic acid 1,1-dimethylethyl ester A mixture of 50% NaOH (10 ml), epichlorohydrin (6 ml) and tetrabutylammonium hydrogen sulfate (0.3 g) kept at 0° C. was added drop by drop to a solution of (3α,5β,7α,12α)-3,7,12-trihydroxy-cholan-24-oic acid 1,1-dimethylethyl ester (prepared according to the procedure described by R. P. Bonar-Law et al., J. Chem. Soc. Perkin Trans. I, 1990, 2245) (0.0045 mol) in CH$_2$Cl$_2$ (10 ml). When the addition was completed the mixture was left to react at room temperature by 24 h. The organic phase was separated, washed with H$_2$O to neutral, dried over Na$_2$SO$_4$ and evaporated. The residue was purified by flash chromatography to obtain 0.86 g of desired product (0.0017 mol).

Yield: 37%

TLC: Carrier: silica gel plates 60 F$_{254}$ Merck

Eluent: n-hexane: AcOEt=1:1 (v/v)

Detection: AcOH: Conc. H$_2$SO$_4$: p-anisaldehyde=100:2:1 R$_f$=0.3

The $^1$H-NMR, $^{13}$C-NMR, IR and MS spectra are consistent with the structure.

B) (3α,5β,7α,12α)-3-[[3-[4,7,10-tris[2-(1,1-dimethylethoxy)-2-oxoethyl]-1,4,7,10- tetraazacyclododecyl]-2-hydroxypropyl]oxy]-7,12-dihydroxy-cholan-24-oic acid (1,1-dimethylethyl)ester A solution containing compound A) (0.001 mol), 1,4,7,10-tetraazacyclododecane-1,4,7-triacetic acid tris(1,1-dimethylethyl)ester monohydrochloride (prepared according to Example 16) (0.001 mol) and triethylamine (1.5 ml) in EtOH (30 ml) was refluxed for 4 h. The reaction mixture was evaporated and the 15 residue was purified by flash chromatography to obtain 0.3 g of desired product (0.0003 mol).

Yield: 27%

TLC: Carrier: silica gel plates 60 $F_{254}$ Merck

Eluent: $CH_2Cl_2$: MeOH=9:1 (v/v)

Detector: AcOH: Conc. $H_2SO_4$: p-anisaldehyde=100:2:1 $R_f$=0.34

The $^1$H-NMR, $^{13}$C-NMR, IR and MS spectra are consistent with the structure.

C) (3α,5β,7α,12α)-3-[[3-[4,7,10-tris(carboxymethyl)-1,4,7,10-tetraazacyclododecyl]-2-hydroxypropyl]oxy]-7,12-dihydroxy-cholan-24-oic acid A solution of compound B) in $CH_2Cl_2$ at 0° C. was added drop by drop to trifluoroacetic acid. When the addition was completed the mixture was left to react at room temperature. When the reaction was over the reaction mixture was evaporated under reduced pressure. The residue was taken up with $CH_2Cl_2$ and evaporated again repeating such a procedure 2 more times. The residue was purified and salted off by elution on an Amberlite® XAD-16 resin using a MeOH/$H_2O$ gradient to obtain the desired product.

The $^1$H-NMR, $^{13}$C-NMR, IR and MS spectra are consistent with the structure.

D) Title compound

According to the procedure described in EXAMPLE 1, compound C) was reacted with $GdCl_3.6H_2O$ in $H_2O$, maintaining a pH of 6.5 by addition of 1N meglumine. The resulting product was salted off by elution with a MeOH/$H_2O$ gradient on an Amberlite® XAD-16 resin.

The IR and MS spectra are consistent with the structure.

EXAMPLE 18

[[(3β,5β,7α,12α)-3-[[5-[4,7,10-tris(carboxymethyl)-1,4,7,10-tetraazacyclododecyl]-4-hydroxy-1-oxopentyl]amino]-7,12-dihydroxy-cholan-24-oate(4⁻)]gadolinate(1⁻)] hydrogen compound with 1-deoxy-1-(methylamino)-D-glucitol (1:1)

A) (3β,5β,7α,12α)-3-(1-oxopent-4-enyl)amino-7,12-dihydroxy-cholan-24-oic acid methyl ester A solution of 4-pentenoic acid (marketed product) and triethylamine in THF was added drop by drop, under nitrogen and at 5° C., to isobutyl chloroformate and subsequently with a solution of (3β,5β,7α,12α)-3-amino-7,12-dihydroxy-cholan-24-oic acid methyl ester (prepared according to the procedure described in EXAMPLE 5) in THF. When the reaction was over, solvent was evaporated and the residue was taken up with $H_2O$ and AcOEt. The organic phase was separated, washed with $H_2O$, dried over $Na_2SO_4$ and evaporated under reduced pressure. The residue was purified by flash chromatography to obtain the desired product.

The $^1$H-NMR, $^{13}$C-NMR, IR and MS spectra are consistent with the structure.

B) (3β,5β,7α,12α)-3-(4,5-epoxy-1-oxopentyl)amino-7,12-dihydroxy-cholan-24-oic acid methyl ester A solution of magnesium monoperphthalate in $H_2O$ was dropped into a solution of compound A) in $CHCl_3$ containing methyltrioctylammonium chloride and kept at 50° C. The pH of the reaction mixture was maintained from 4.5 to 5 by addition of 5% NaOH. When the reaction was over the organic phase was separated and the aqueous phase was extracted with $CHCl_3$. The organic phases were combined, washed with $H_2O$, dried over $Na_2SO_4$ and evaporated after checking for the absence of peroxides. The residue was purified by flash chromatography to obtain the desired product.

The $^1$H-NMR, $^{13}$C-NMR, IR and MS spectra were consistent with the structure.

C) (3β,5β,7α,12α)-3-[[5-[4,7,10-tris[2-(1,1-dimethylethoxy)-2-oxoethyl]-1,4,7,10-tetraazacyclododecyl]-4-hydroxy-1-oxopentyl]amino]-7,12-dihydroxycholan-24-oic acid A solution containing B), 1,4,7,10-tetraazacyclododecane-1,4,7-triacetic acid tris(1,1-dimethylethyl)ester monohydrochloride (prepared according to Example 16) and triethylamine in EtOH was refluxed for 4 h. The reaction mixture was evaporated and the residue was purified by flash chromatography to obtain the desired product.

The $^1$H-NMR, $^{13}$C-NMR, IR and MS spectra were consistent with the structure.

D) (3β,5β,7α,12α)-3-[[5-[4,7,10-tris(carboxymethyl)-1,4,7,10-tetraazacyclododecyl]-4-hydroxy-1-oxopentyl]amino]-7,12-dihydroxy-cholan-24-oic acid A solution of compound C) in $CH_2Cl_2$ at 0° C. was added drop by drop to trifluoroacetic acid. When the addition was completed the mixture was left to react at room temperature. When the reaction was over the reaction mixture was evaporated under reduced pressure. The residue was taken up with $CH_2Cl_2$ and evaporated again, repeating such a procedure 2 more times. The residue was purified and salted off by elution on an Amberlite® XAD-16 resin using a MeOH/$H_2O$ gradient to obtain the desired product.

The $^1$H-NMR, $^{13}$C-NMR, IR and MS spectra were consistent with the structure.

E) Title compound

According to the procedure described in EXAMPLE 1, compound D) was reacted with $GdCl_3.6H_2O$ in $H_2O$, maintaining a pH of 6.5 by addition of 1N meglumine. The resulting desired product was salted off by elution with a MeOH/$H_2O$ gradient on an Amberlyte XAD-16 resin.

The IR and MS spectra were consistent with the structure.

EXAMPLE 19

The relaxivities r1 and r2 ($mM^{-1}.s^{-1}$) of the 4-carboxy-5,8,11-tris(carboxymethyl)-1-[4-[[[[(3α,5β,7α,12α)-3,7,12-trihydroxy-24-oxocholan-24-yl]amino]acetyl]amino]phenyl]-2-oxa-5,8,11-triazatridecan-13-oic acid gadolinium complex (Compound 1F) were evaluated in SERONORM-HUMAN™ serum (NYCOMED), in a magnetic filed of a 20 MHz frequency, at a temperature of 39° C., (MINISPEC PC-120 device), using the following sequences: Inversion Recovery; CPMG; and compared with those of Gd-DTPA/Dimeg (Magnevist®), Gd-DOTA/meg (Dotarem®), Gd-BOPTA/Dimeg and $GdCl_3$ [percent ratios being calculated with respect to $GdCl_3$] obtained under the same experimental conditions. The results are reported in Table 1.

TABLE 1

| Compounds | $r_1$ (mM$^{-1}$.s$^{-1}$) | A.100 | $r_2$ (mM$^{-1}$.s$^{-1}$) | B.100 |
|---|---|---|---|---|
| Compound 1F | 19.23 | 183.8 | 22.02 | 182.1 |
| gompound 4F | 12.02 | 114.9 | 13.74 | 113.6 |
| Magnevist ® | 4.96 | 47.42 | 5.43 | 44.91 |
| Dotarem ® | 4.34 | 41.49 | 5.02 | 41.52 |
| Gd-BOPTA | 9.31 | 89.00 | 11.19 | 92.55 |
| GdCl$_3$ | 10.46 | 100 | 12.09 | 100 |

We claim:

1. A compound of general formula (I)

A-L-B         (I)

wherein

A is the residue of a bile acid, said residue being the group of a bile acid obtainable by bioconversion from cholesterol, said bile acid being a member selected from the group consisting of cholic, deoxycholic, chenodeoxycholic, ursodeoxycholic, and lithocholic or said residue A is the conjugation product thereof with taurine or glycine;

L is a ligand between at least one of the C-3, C-7, C-12 and C-24 positions of the residue of said bile acid and B; and L has the formula II

 (II)

in which m is an integer varying from 1 to 10, and when m has a value above 1, Y have different meanings, Y corresponds to the following succession of groups,

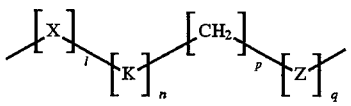

wherein n, l and q are 0 or 1, p varies between 0 and 10,

X is an O atom, a S atom, or a —NR group, in which R is a H atom, or a (C$_1$–C$_5$) alkyl group, K is an unsubstituted or substituted benzene ring or a —CHR$_1$ group, wherein R$_1$ is a hydrogen atom, a —COOH group, or a —SO$_3$H group, Z is an O atom, a S atom, or one of —CO— or —CS— groups, B is the residue of a chelating agent of a bivalent or trivalent metal ion having an atomic number varying from 20 to 31, 39, 42, 43, 44, 49, or from 57 to 83 with the proviso that at least one of l, n, q, p is different from O and when X and Z are both O or S atoms, q or n is equal to 1, and complex chelates of said compound of formula (I) with ions of metal elements having atomic number ranging from 20 to 31, 39, from 42 to 44, 49 and from 57 to 83 and salts thereof with a) a physiologically acceptable organic base which is a primary, secondary, or a tertiary amine or a basic amino acid, b) with an inorganic base whose cations are sodium, potassium, magnesium, calcium or mixtures thereof, or c) with a physiologically acceptable anion of an organic acid which is the acetate, the succinate, the citrate, the fumarate, the maleate, the oxalate, or with an anion of an inorganic halohydric acid.

2. A compound according to claim 1 wherein said residue B is unconjugated or conjugated by a second chain L of formula (II), to another residue A.

3. A compound according to claim 1, wherein B is a member selected from the group consisting of polyaminocarboxylic acids and ester or amide derivatives thereof EDTA; DTPA; EOB-DTPA; BOPTA; DTPA-BMA; DOTA; DOTMA; DO3A; HPDO3A; and MCTA.

4. A compound according to claim 1 wherein B is a member selected from the group consisting of a) one of the acids DPDP or EDTP;

b) a polyaminophosphonic acid and derivatives thereof or a polyaminophosphinic acid and derivatives thereof 1,4,7,10-tetraazacyclododecane-1,4,7,10-tetrakis [methylene(methylphosphinic) acid and 1,4,7,10-tetraazacyclododecane-1,4,7,10-tetrakis[methylene (methylphosphonic)] acid; and c) a macrocyclic chelant which is a texafirine, a porphyrine or a phthalocyanine.

5. A compound according to claim 1, wherein said ligand L has the formula (III),

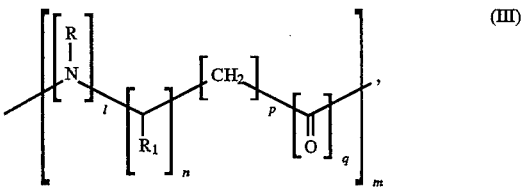 (III)

6. A compound according to claim 1, wherein said ligand L has the formula (IV),

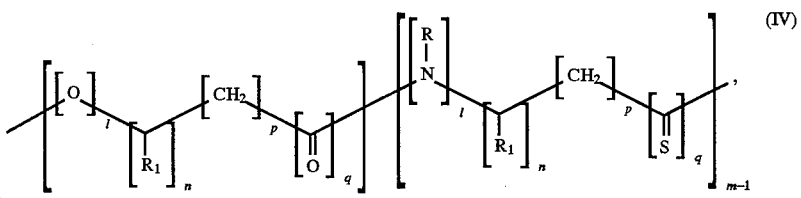 (IV)

7. A compound according to claim 1, wherein said ligand L has the formula (V),

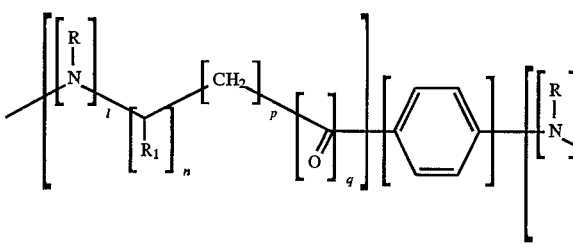
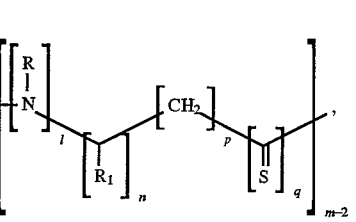

(V)

8. A compound according to claim 1, wherein said ligand has the formula (VI),

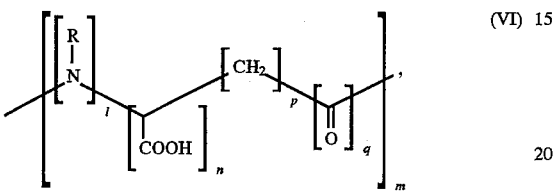

(VI)

9. A compound according to claim 1, wherein the bivalent or trivalent metal ion complexed by said chelant residue B is a member selected from the group consisting of $Fe^{2+}$, $Fe^{3+}$, $Gd^{3+}$, $Eu^{3+}$, $Dy^{3+}$, $La^{3+}$, $Yb^{3+}$, and $Mn^{2+}$.

10. A compound according to claim 1, wherein the bivalent or trivalent metal ion complexed by said chelant residue B is radioisotope $51_{Cr}$, $67_{Ga}$, $68_{Ga}$, $111_{In}$, $99m_{Tc}$, $140_{La}$, $175Yb$, $153_{Sm}$, $166_{Ho}$, $90_Y$, $149_{Pm}$, $177_{Lu}$, $47_{Sc}$, $142_{Pr}$, $159_{Gd}$ or $212_{Bi}$.

11. A compound according to claim 1, wherein said physiologically acceptable organic base is a member selected from the group consisting of ethanolamine, diethanolamine, morpholine, glucamine, N,N-dimethylglucamine, N-methylglucamine, lysine, arginine and ornithine.

12. The compound according to claim 1, wherein said physiologically acceptable anion of said inorganic acid is a chloride, a bromide or an iodide.

13. The compound according to claim 1, wherein A is the residue of cholic acid or of a derivative thereof and B is the residue of DTPA or of a derivative thereof.

14. The compound according to claim 1, wherein A is the residue of cholic acid or of a derivative thereof and B is the residue of BOPTA or of a derivative thereof.

15. The compound according to claim 1, wherein A is the residue of cholic acid or of a derivative thereof and B is the residue of DOTA or of a derivative thereof.

16. The compound according to claim 1, which is a member selected from the group consisting of:

Comp. 1 [[4-carboxy-5,8,11-tris(carboxymethyl)-1-[4-[[[(3α,5β,7α,12α)-3,7,12-trihydroxy-24-oxocholan-24-yl]amino]acetyl]amino]phenyl]-2-oxa-5,8,11-triazatridecan-13-oic acid;

Comp. 2 [[4-carboxy-5,8,11-tris(carboxymethyl)-1-[4-[[(3α,5β,7α,12α)-3,7,12-trihydroxy-24-oxocholan-24-yl]amino]phenyl]-2-oxa-5,8,11-triazatridecan-13-oic acid;

Comp. 3 [[3,6,9-tris(carboxymethyl)-10-(phenylmethoxy)methyl-11-oxo-14-[[(3α,5β,7α,12α)-3,7,12-trihydroxy-24-oxocholan-24-yl]amino]-3,6,9,12-tetraazatetradecanoic acid;

Comp. 4 [[10-[2-oxo-2-[[3-[[2-[[(3α,5β,7α,12α)-3,7,12-trihydroxy-24-oxocholan-24-yl]amino]ethyl]amino]propyl]amino]ethyl]-1,4,7,10-tetraazacyclododecan-1,4,7-triacetic acid;

Comp. 5 [[(3β,5β,7α,12α)-3-[[13-carboxy-6,9,12-tris(carboxymethyl)-1,4-dioxo-5-[(phenylmethoxy)methyl]-3,6,9,12-tetraazatridecyl]amino]-7,12-dihydroxy-cholan-24-oic acid;

Comp. 6 [[(3β,5β,7α,12α)-3-[[17-carboxy-10,13,16-tris(carboxymethyl)-8-oxo-9-[(phenylmethoxy)methyl]-3,7,10,13,16-pentaazaheptadecyl]oxy]-7,12-dihydroxy-cholan-24-oic acid;

Comp. 7 [[-(3β,5β,7α,12α)-7,12-dihydroxy-3-[2-[[[[4-[4,12-bis(carboxy)-5,8,11-tris(carboxymethyl)-2-oxa-5,8,11-triazadodecyl]phenyl]amino]thioxomethyl]amino]ethoxy]-cholan-24-oic acid;

Comp. 8 (3β,5β,7α,12α)-7,12-dihydroxy-3-[[[[3-[[[4,7,10-tris(carboxymethyl)-1,4,7,10-tetraazacyclodec-1-yl]acetyl]amino]propyl]amino]acetyl]amino]-cholan-24-oic acid;

Comp. 9 [[3,6,9-tris(carboxymethyl)-10-[(phenylmethoxy)methyl]-11-oxo-17-[[(3α,5β,7α,12α)-3,7,12-trihydroxy-24-oxocholan-24-yl]amino]-3,6,9,12-tetraazaoctadecanedioic acid;

Comp. 10 [[(3β,5β,7α,12α)-3-[[13-carboxy-6,9,12-tris(carboxymethyl)-1,4-dioxo-3,6,9,12-tetraazatridecyl]amino]-7,12-dihydroxy-cholan-24-oic acid;

Comp. 11 [(3β,5β,7α,12α)-(3'β,5'β,7'α,12'α)-3,3'-[[6,9,12-tris(carboxymethyl)-1,4,14,17-tetraoxo-3,6,9,12,15-pentaazaheptadecan-1,17-diyl]bisimino]bis[7,12-dihydroxycholan-24-oic acid;

Comp. 12 [[[3β(S),5β,7α,12α]-7,12-dihydroxy-3-[[4-[[[5-[bis[2-[bis(carboxymethyl)amino]ethyl]amino]-5-carboxypentyl]amino]thioxomethyl]amino]benzoyl]amino]-cholan-24-oic acid;

Comp. 13 [[[3β(S),5β,7α,12α]-7,12-dihydroxy-3-[[4-[[5-[bis[2-[bis(carboxymethyl)amino]ethyl]amino]-5-carboxypentyl]amino]-1,4-dioxobutyl]amino]cholan-24-oic acid;

Comp. 14 [[(3β,5β,7α,12α)-7,12-dihydroxy-3-[[4-[[2-[[4-[4,12-bis(carboxy)-5,8,11-tris(carboxymethyl)-2-oxa-5,8,11-triazadodecyl]phenyl]amino]-2-oxoethyl]amino]-1,4-dioxobutyl]amino]-cholan-24-oic acid;

Comp. 15 3,6,9-tris(carboxymethyl)-14-[[(3β,5β,7α,12α)-7,12-dihydroxy-24-oxo-24-[(2-sulfoethyl)amino]-cholan-3-yl]amino]-11,14-dioxo-3,6,9,12-tetraazatetradecanoic acid;

Comp. 16 N-[(3β,5β,7α,12α)-3-[[13-carboxy-6,9,12-tris(carboxymethyl)-1,4-dioxo-5-[(phenylmethoxy)methyl[- 3,6,9,12-tetraazatridecyl]amino]-7,12-dihydroxy-24-oxocholan-24-yl]glycine Comp. 17 (3β,5β,7α)-3-[[13-carboxy-6,9,12-tris(carboxymethyl)-1,4-dioxo-5-[(phenylmethoxy)methyl]-3,6,9,12-tetraazatridecyl]amino]-7-hydroxy-cholan-24-oic acid;

Comp. 18 (3β,5β,12α)-3-[[13-carboxy-6,9,12-tris(carboxymethyl)-1,4-dioxo-5-[(phenylmethoxy)methyl]-3,6,9,12-tetraazatridecyl]amino]-12-hydroxy-cholan-24-oic acid;

Comp. 19 (3β,5β)-3-[[13-carboxy-6,9,12-tris(carboxymethyl)-1,4-dioxo-5-[(phenylmethoxy)methyl]-3,6,9,12-tetraazatridecyl]amino]-cholan-24-oic acid;

Comp. 20 (3β,5β,7α,12α)-3-[[17-carboxy-10,13,16-tris (carboxymethyl)-1,8-dioxo-9-[(phenylmethoxy) methyl]-7,10,13,16-tetraazaheptadecyl]amino]-7,12-dihydroxy-cholan-24-oic acid;

Comp. 21 (3β,5β,7α,12α)-7,12-dihydroxy-3-[[3-[[[4,7, 10-tris(carboxymethyl)-1,4,7,10-tetraazacyclododec-1-yl]acetyl]amino]propyl]amino]-cholan-24-oic acid;

Comp. 22 3,6,9-tris(carboxymethyl)-14-[[(3β,5β,7α,12α) -7,12-dihydroxy-24-oxo-24-[(2-sulfoethyl)amino]-cholan-3-yl]amino]-11,14-dioxo-3,6,9,12-tetraazatetradecanoic acid;

Comp. 23 [(3β,5β,7α,12α)-3-[[17-carboxy-10,13,16-tris (carboxymethyl)-1,8-dioxo-7,10,13,16-tetraazaheptadecyl]amino]-7,12-dihydroxy-cholan-24-oic acid;

Comp. 24 (17S)-3,6,9-tris(carboxymethyl)-11-oxo-17-[[( 3β,5β,7α,12α)-3,7,12-trihydroxy-24-oxocholan-24-yl] amino]-3,6,9,12-tetraazaoctadecanedioic acid;

Comp. 25 [[(3β,5β,7α,12α)-3-[[6-[[[bis[2-[bis (carboxymethyl)amino]ethyl]amino]acetyl]amino]-1-oxohexyl]amino]-7,12-dihydroxy-cholan-24-oic acid;

Comp. 26 (3β,5β,7α,12α)-3-[[[[[bis[2-[bis (carboxymethyl)amino]ethyl]amino]acetyl]amino] acetyl]amino]-7,12-dihydroxy-cholan-24-oic acid;

Comp. 27 N⁶-[[bis[2-[bis(carboxymethyl)amino]ethyl] amino]acetyl]-N²-[(3α,5β,7α,12α)-3,7,12-trihydroxy-24-oxocholan-24-yl]-L-lysine Comp. 28 [[N⁶-[(4S)[4-[bis[2-[bis(carboxymethyl) amino]ethyl]amino]-4-carboxy-1-oxobutyl]-N²-[(3α, 5β,7α,12α)-3,7,12-trihydroxy-24-oxocholan-24-yl]-L-lysine Comp. 29 [3β(S),5β,7α,12α]-3-[4-carboxy-4-[bis[2-[bis (carboxymethyl)amino]ethyl]amino]-1-oxobutyl] amino]-7,12-dihydroxy-cholan-24-oic acid;

Comp. 30 [[10-[2-[[2-[[(3β,5β,7α,12α)-7,12-dihydroxy-24-oxo-24-[(2-sulfoethyl)amino]cholan-3-yl]amino]-2-oxoethyl]amino]-2-oxoethyl]-1,4,7,10-tetraazacyclododecane-1,4,7-triacetic acid;

Comp. 31 (3β,5β,7α,12α)-3-[[[[[4,7,10-tris (carboxymethyl)-1,4,7,10-tetraazacyclododecyl] acetyl]amino]acetyl]amino]-7,12-dihydroxy-cholan-24-oic acid;

Comp. 32 N²-[(3α,5β,7α,12α)-3,7,12-trihydroxy-24-oxocholan-24-yl]-N⁶-[[4,7,10-tris(carboxymethyl)-1,4,7,10-tetraazacyclododecyl]acetyl]-L-lysine Comp. 33 (3β,5β,7α,12α)-3-[[6-[[[4,7,10-tris (carboxymethyl)-1,4,7,10-tetraazacyclododecyl] acetyl]amino]-1-oxohexyl]amino]-7,12-dihydroxycholan-24-oic acid;

Comp. 34 [[(3α,5β,7α,12α)-3-[[3-[4,7,10-tris (carboxymethyl)-1,4,7,10-tetraazacyclododecyl]-2-hydroxypropyl]oxy]-7,12-dihydroxy-cholan-24-oic acid;

Comp. 35 [[(3β,5β,7α,12α)-3-[[5-[4,7,10-tris (carboxymethyl)-1,4,7,10-tetraazacyclododecyl]-4-hydroxy-1-oxopentyl]amino]-7,12-dihydroxy-cholan-24-oic acid.

17. A contrast diagnostic pharmaceutical composition for the gastrointestinal tract imaging of organs, tissues and both organs and tissues of human and animal bodies comprising at least one of said complex chelates according to claim 1 or a salt thereof.

18. The pharmaceutical composition according to claim 17, for use in nuclear magnetic resonance.

19. The method of obtaining an image of at least one of an organ and tissue of human and animal body which consists of carrying out nuclear magnetic resonance to obtain a diagnostic formulation by administration orally or parenterally of one of the complex chelates of a compound of formula (I)

A-L-B  (I), wherein

A is the residue of a bile acid, said residue being the group of a bile acid obtainable by bioconversion from cholesterol, said bile acid being a member selected from the group consisting of cholic, deoxycholic, chenodeoxycholic, ursodeoxycholic and lithocholic, or said residue A is the conjugation product thereof with taurine or glycine;

L is a ligand between at least one of the C-3, C-7, C-12 and C-24 positions of the residue of said bile acid and B; and L has formula (II)

  (II)

in which m is an integer varying from 1 to 10, and when m has a value above 1, Y have different meanings, Y corresponds to the following succession of groups,

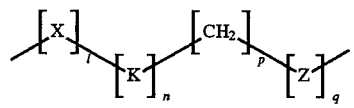

wherein n, l and q are 0 or 1, p varies between 0 and 10,

X is an O atom, a S atom, or a —NR group, in which

R is a H atom, or a (C₁-C₅) alkyl group,

K is an unsubstituted or substituted benzene ring or a —CHR₁ group, wherein

R₁ is a hydrogen atom, a —COOH group, or a —SO₃H group,

Z is an O atom, a S atom, or one of —CO— or —CS— groups,

B is the residue of a chelating agent of a bivalent or trivalent metal ion having an atomic number varying from 20 to 31, 39, 42, 43, 44, 49, or from 57 to 83 with the proviso that at least one of l, n, q, p is different from 0 and when X and Z are both O or S atoms, q or n is equal to 1, and complex chelates of said compound of formula (I) with ions of metal elements having atomic number ranging from 20 to 31, 39, from 42 to 44, 49 and from 57 to 83 and salts thereof with a) a physiologically acceptable organic base which is a primary, secondary, or a tertiary amine or a basic amino acid, b) with an inorganic base whose cations are sodium, potassium, magnesium, calcium or mixtures thereof, or c) with a physiologically acceptable anion of an organic acid which is the acetate, the succinate, the citrate, the fumarate, the maleate, the oxalate, or with an anion of the inorganic halohydric acid.

20. The method according to claim 19 wherein the organ is the liver and an image of the heptatobiliary system is obtained.

* * * * *